(12) United States Patent
Farah et al.

(10) Patent No.: US 10,851,069 B2
(45) Date of Patent: Dec. 1, 2020

(54) COMPOSITIONS OF CRYSTALLIZED HYDROPHOBIC COMPOUNDS AND METHODS OF MAKING AND USING SAME

(71) Applicant: Massachusetts Institute of Technology, Cambridge, MA (US)

(72) Inventors: Shady Farah, Quincy, MA (US); Joshua C. Doloff, Quincy, MA (US); Robert S. Langer, Newton, MA (US); Daniel G. Anderson, Framingham, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/091,330

(22) PCT Filed: Apr. 4, 2017

(86) PCT No.: PCT/US2017/026009
§ 371 (c)(1),
(2) Date: Oct. 4, 2018

(87) PCT Pub. No.: WO2017/176804
PCT Pub. Date: Oct. 12, 2017

(65) Prior Publication Data
US 2019/0210976 A1 Jul. 11, 2019

Related U.S. Application Data

(60) Provisional application No. 62/318,208, filed on Apr. 4, 2016, provisional application No. 62/317,831, filed on Apr. 4, 2016.

(51) Int. Cl.
| | |
|---|---|
| C07D 239/49 | (2006.01) |
| A61K 31/505 | (2006.01) |
| A61P 29/00 | (2006.01) |
| A61K 31/404 | (2006.01) |
| A61K 31/416 | (2006.01) |
| A61K 31/4439 | (2006.01) |
| A61K 31/444 | (2006.01) |
| A61K 31/4709 | (2006.01) |
| A61K 31/496 | (2006.01) |
| A61K 31/5025 | (2006.01) |
| A61K 31/519 | (2006.01) |
| A61K 31/5377 | (2006.01) |
| A61K 31/551 | (2006.01) |
| A61K 31/553 | (2006.01) |
| A61K 9/00 | (2006.01) |

(52) U.S. Cl.
CPC .......... *C07D 239/49* (2013.01); *A61K 9/0024* (2013.01); *A61K 31/404* (2013.01); *A61K 31/416* (2013.01); *A61K 31/444* (2013.01); *A61K 31/4439* (2013.01); *A61K 31/4709* (2013.01); *A61K 31/496* (2013.01); *A61K 31/5025* (2013.01); *A61K 31/519* (2013.01); *A61K 31/5377* (2013.01); *A61K 31/551* (2013.01); *A61K 31/553* (2013.01); *A61P 29/00* (2018.01); *C07B 2200/13* (2013.01)

(58) Field of Classification Search
CPC ...... C07D 239/49; A61K 31/505; A61P 29/00
USPC .......................................... 544/325; 514/275
See application file for complete search history.

(56) References Cited

U.S. PATENT DOCUMENTS

| | | | |
|---|---|---|---|
| 7,491,731 B2 * | 2/2009 | Emerson ............ | C07K 14/7153 514/275 |
| 2004/0002145 A1 | 1/2004 | Shewchuk et al. | |
| 2010/0256148 A1 | 10/2010 | Manthey | |
| 2015/0196566 A1 | 7/2015 | Hadd et al. | |
| 2016/0030360 A1 | 2/2016 | Vegas et al. | |
| 2019/0083495 A1 | 3/2019 | Doloff et al. | |

FOREIGN PATENT DOCUMENTS

| | | |
|---|---|---|
| WO | WO 2014/132072 A1 | 9/2014 |
| WO | WO 2014/138888 A1 | 9/2014 |
| WO | WO 2015/028454 A2 | 3/2015 |
| WO | WO 2017/176792 A1 | 10/2017 |

OTHER PUBLICATIONS

Kzhyshkowska et al. Journal of Leukocyte Biology, 98, 953-962, Dec. 2015.*
Rolfe et al. 'The Fibrotic Response to Implanted Materials: Implications for Tissue Engineering' in 'Regenerative Medicine and Tissue Engineering-Cells and Biometerials', edited by Daniel Eberli, pp. 551-568, and Title page, 2011 an.*
Braga et al., Frontiers in Immunology, vol. 6, Article 602, pp. 1-8, 2015.*
Freshney et al., Culture of Animal Cells, A Manual of Basic Technique, Alan R. Liss, Inc., 1983, New York, p. 4.*
Dermeret al., Bio/Technology, 1994, 12:320.*
Khadka et al. Asian Journal of Pharmaceutical Sciences 9, 304-316, 2014.*
Patel et al. Asian Journal of Pharmaceutics-October-December, pp. 216-220.*
Notification of Transmittal of the International Search Report and Written Opinion for International Application No. PCT/US2017/026009, entitled: "Compositions of Crystallized Hydrophobic Compounds and Methods of Making and Using Same," dated Aug. 7, 2017.

(Continued)

*Primary Examiner* — Venkataraman Balasubramanian
(74) *Attorney, Agent, or Firm* — Hamilton, Brook, Smith & Reynolds, P.C.

(57) ABSTRACT

The present invention provides, in certain embodiments, compositions comprising a uniform population of free, single crystals of a hydrophobic compound. Methods of administering, and processes for preparing, compositions comprising a uniform population of free, single crystals of a hydrophobic compound are also provided.

20 Claims, 36 Drawing Sheets

Specification includes a Sequence Listing.

(56) References Cited

OTHER PUBLICATIONS

Kzhyshkowska, J., et al., "Macrophage responses to implants: prospects for personalized medicine", Journal of Leukocyte Biology, 98: 953-962 (Dec. 2015).

International Search Report and Written Opinion for Int'l Application No. PCT/US2017/026009, entitled: Compositions of Crystallized Hydrophobic Compounds and Methods of Making and Using Same, dated Aug. 7, 2017.

Affara, N.I., et al., "B cells regulate macrophage phenotype and response to chemotherapy in squamous carcinomas," Cancer Cell, 25(6): 809-821 (2014).

Albert, Daniel H., et al., "Preclinical activity of ABT-869, a multitargeted receptor tyrosine kinase inhibitor", Mol. Cancer Ther., 5(4): 995-1006 (2006).

Anderson, J.M. et al., "Foreign body reaction to biomaterials," Semin Immunol, 20(2): 86-100 (2008).

Attur, M.G. et al., "Differential anti-inflammatory effects of immunosuppressive drugs: cyclosporin, rapamycin and FK-506 on inducible nitric oxide synthase, nitric oxide, cyclooxygenase-2 and PGE 2 production," Inflammation Research, 49(1): 20-26 (2000).

Bendell, J., et al., A Phase 1 Study of ARRY-382, an Oral Inhibitor of Colony stimulating Factor-1 Receptor (CSF1R), in Patients with Advanced of Metastatic Cancers; EORTC-NCI-AACR Symposium on Molecular Targets and Cancer Therapeutics, Nov. 1, 2013, from the Internet: https://www.arraybiopharma.com/product-pipeline/arry-382/.

Bernard-Gauthier, Vadim et al., "5-(4-((4-[$^{18}$F]fluorobenzyl)oxy)-3-methoxybenzyl)pyrimidine-2,4-diamine: A selective dual inhibitor for potential PET imaging of TRK/CSF-1R" Bioorganic & Medicinal Chemistry Letters, 24: 4784-4790 (2014).

Bhaumik, S. et al., "Differential modulation of nitric oxide production by curcumin in host macrophages and NK cells," FEBS Lett, 483(1): 78-82 (2000).

Bratlie, K.M., et al., "Rapid biocompatibility analysis of materials via in vivo fluorescence imaging of mouse models," PloS one, 5(4): e10032 (2010).

Bryers, J.D. et al., "Engineering biomaterials to integrate and heal: the biocompatibility paradigm shifts," Biotechnol Bioeng, 109(8): 1898-1911 (2012).

Burns, Christopher J., et al., "Discovery of 2-($\alpha$-methylbenzylamino) pyrazines as potent Type II inhibitors of FMS", Bioorganic & Medicinal Chemistry Letters, 19: 1206-1209 (2009).

Butowski, Nicholas, et al., "Orally administered colony stimulating factor 1 receptor inhibitor PLX3397 in recurrent glioblastoma: An Ivy Foundation Early Phase Clinical Trials Consortium phase II study," Neuro-Oncology, 18(4): 557-564 (2015).

Carlsen, H.S., et al., "Monocyte-like and mature macrophages produce CXCL13 (B cellattracting chemokine 1) in inflammatory lesions with lymphoid neogenesis," Blood, 104(10): 3021-3027 (2004).

Cobelli, N. et al., "Mediators of the inflammatory response to joint replacement devices," Nature Reviews Rheumatology, 7(10): 600-608 (2011).

Conway, J.G., et al., "Inhibition of colony-stimulating-factor-1 signaling in vivo with the orally bioavailable cFMS kinase inhibitor GW2580," Proceedings of the National Academy of Sciences of the United States of America, 102(44): 16078-16083 (2005).

Dang, T.T. et al., "Enhanced function of immuno-isolated islets in diabetes therapy by cocncapsulation with an anti-inflammatory drug," Biomatcrials, 34(23): 5792-5801 (2013).

De Vos, P. et al., "Alginate-based microcapsules for immunoisolation of pancreatic islets," Biomaterials, 27(32): 5603-5617 (2006).

Denton, M.D. et al., "Immunosuppressive strategies in transplantation," Lancet, 353(9158): 1083-1091 (1999).

Diel, I.J., et al., "Adverse effects of bisphosphonates: current issues," The journal of supportive oncology, 5(10): 475-482 (2007).

Doloff, et al., "Colony stimulating factor-1 receptor is a central component of the foreign body response to biomaterial implants in rodents and non-human primates," Nature Materials, Advance Online Publication, Published online—Mar. 20, 2017.

Farra, R., et al. "First-in-human testing of a wirelessly controlled drug delivery microchip," Sci Transl Med, 4(122): 122ra121 (2012).

Fattahi, P. et al., "A review of organic and inorganic biomaterials for neural interfaces," Advanced materials, 26(12): 1846-1885 (2014).

Gennaro, et al., Remington's Pharmaceutical Sciences (18th ed., Mack Publishing Company, 1990 (Part 8: Pharmaceutical Preparations and their Manufacture).

Gordon, S., "Alternative activation of macrophages," Nat Rev Immunol, 3(1): 23-35 (2003).

Grainger, D.W., "All charged up about implanted biomaterials," Nat Biotechnol, 31(6): 507-509 (2013).

Guo, Jun et al., "Inhibition of phosphorylation of the colony-stimulating factor-1 receptor (c-Fms) tyrosine kinase in transfected cells by ABT-869 and other tyrosine kinase inhibitors", Mol. Cancer Ther., 5(4): 1007-1013 (2006).

Halloran, P.F., "Immunosuppressive drugs for kidney transplantation," N Engl J Med, 351(26): 2715-2729 (2004).

Harding, J.L. and M.M. Reynolds, "Combating medical device fouling," Trends in biotechnology, 32(3): 140-146 (2014).

Huang, Hui, et al., "Pyrido[2,3-d]pyrimidin-5-ones: A Novel Class of Antiinflammatory Macrophage Colony-Stimulating Factor-1 Receptor Inhibitors", J. Med. Chem., 52: 1081-1099 (2009).

Hubbell, J.A. and R. Langer, "Translating materials design to the clinic," Nature materials, 12(11): 963-966 (2013).

Illig, Carl R., et al., "Optimization of a Potent Class of Arylamide Colony-Stimulating Factor-1 Receptor Inhibitors Leading to Anti-inflammatory Clinical Candidate 4-Cyano-N-[2-(1-cyclohexen-1-yl)-4-[1-[(dimethylamino)-acetyl]-4-piperidinyl]phenyl]-1H-imidazole-2-carboxamide (JNJ-28312141)," J. Med. Chem., 54: 7860-7883 (2011).

International Preliminary Report on Patentability for Int'l Application No. PCT/US2017/026009, entitled: Compositions of Crystallized Hydrophobic Compounds and Methods of Making and Using Same, dated Oct. 9, 2018.

Ito, M., et al., "NOD/SCID/gamma(c)(null) mouse: an excellent recipient mouse model for engraftment of human cells," Blood, 100(9): 3175-3182 (2002).

Jacobs-Tulleneers-Thevissen, D. et al., "Sustained function of alginate-encapsulated human islet cell implants in the peritoneal cavity of mice leading to a pilot study in a type 1 diabetic patient," Diabetologia, 56(7): 1605-1614 (2013).

Jhunjhunwala, S., et al., "Neutrophil Responses to Sterile Implant Materials," PloS one, 10(9): e0137550 (2015).

Jung, Myung-Ho, et al., "Design, synthesis, and antiproliferative activity of new 1H-pyrrolo[3,2-c]pyridine derivatives against melanoma cell lines. Part 2" Bioorganic & Medicinal Chemistry Letters, 22: 4362-4367 (2012).

Kearney, C.J. and D.J. Mooney, "Macroscale delivery systems for molecular and cellular payloads," Nature Materials, 12(11): 1004-1017 (2013).

Khan, W. et al., "Implantable Medical Devices," Focal Controlled Drug Delivery. Springer US, pp. 33-59 (2014).

Kim, G.Y. et al., "Curcumin inhibits immunostimulatory function of dendritic cells: MAPKs and translocation of NF-kappa B as potential targets," J. Immunol., 174(12): 8116-8124 (2005).

Kim, W. et al., "Dietary curcumin and limonin suppress CD4+ T-cell proliferation and interleukin-2 production in mice," J. Nutr, 139(5): 1042-1048 (2009).

King, A. et al., "The effect of host factors and capsule composition on the cellular overgrowth on implanted alginate capsules," Journal of Biomedical Materials Research, 57(3): 374-383 (2001).

Kurtz, S. et al., "Projections of primary and revision hip and knee arthroplasty in the United States from 2005 to 2030," The Journal of bone and joint surgery American vol. 2007, 89(4): 780-785 (2007).

Kyriakides, T.R. et al., "The CC chemokine ligand, CCL2/MCP1, participates in macrophage fusion and foreign body giant cell formation," Am. J. Pathol., 165(6): 2157-2166 (2004).

Langer, R., "Perspectives and challenges in tissue engineering and regenerative medicine," Advanced Materials, 21(32-33): 3235-3236 (2009).

(56) References Cited

OTHER PUBLICATIONS

Laskin, D.L., et al., "Macrophages and tissue injury: agents of defense or destruction?" Annual review of pharmacology and toxicology. 51: 267-288 (2011).
Lee, K.Y. and D.J. Mooney, "Alginate: properties and biomedical applications," Progress in Polymer Science, 37(1): 106-126 (2012).
MacDonald, K.P., et al., "An antibody against the colony-stimulating factor 1 receptor depletes the resident subset of monocytes and tissue- and tumor-associated macrophages but does not inhibit inflammation," Blood, 116(19): 3955-3963 (2010).
Manoury, B. et al., "TIMP-1 is a key factor of fibrogenic response to bleomycin in mouse lung," International Journal of Immunopathology and Pharmacology, 19(3): 471-487 (2006).
Medical Devices and the Public's Health: The FDA 510(k) Clearance Process at 35 Years. 2011: 1-298.
Morch, Y.A. et al., "Effect of $Ca^{2+}$, $Ba^{2+}$, and $Sr^{2+}$ on alginate microbeads," Biomacromolecules, 7(5): 1471-1480 (2006).
Nichols, S.P. et al., "Biocompatible materials for continuous glucose monitoring devices," Chemical Reviews, 113(4): 2528-2549 (2013).
Paredes-Juarez, G.A., et al., "The role of pathogen-associated molecular patterns in inflammatory responses against alginate based microcapsules," J. Control Release, 172(3): 983-992 (2013).
Patch, Raymond J., et al., "Potent 2'-aminoanilide inhibitors of cFMS as potential anti-inflammatory agents",Bioorganic & Medicinal Chemistry Letters, 17: 6070-6074 (2007).
Perez-Cambrodi, R.J. et al., "The posterior chamber phakic refractive lens (PRL): A review," Eye, 27(1): 14-21 (2013).
Pyonteck, S.M., et al., "CSF-1R inhibition alters macrophage polarization and blocks glioma progression," Nat. Med., 19(10): 1264-1272 (2013).
Rhen, T. and J.A. Cidlowski, "Antiinflammatory action of glucocorticoids-new mechanisms for old drugs," New England Journal of Medicine, 353(16): 1711 (2005).
Robitaille, R. et al., "Inflammatory response to peritoneal implantation of alginate-poly-L-lysine microcapsules," Biomaterials, 26(19): 4119-4127 (2005).
Rodriguez, A. et al., "Quantitative in vivo cytokine analysis at synthetic biomaterial implant sites," Journal of Biomedical Materials Research, Part A, 89(1): 152-159 (2009).
Rosen, M.R. et al., "The road to biological pacing," Nat. Rev. Cardiol., 8(11): 656-666 (2011).
Scott, David A., et al., "3-Amido-4-anilinocinnolines as a novel class of CSF-1R inhibitor", Bioorganic & Medicinal Chemistry Letters, 21: 1382-1384 (2011).
Scott, David A., et al., "Pyridyl and thiazolyl bisamide CSF-1R inhibitors for the treatment of cancer", Bioorganic & Medicinal Chemistry Letters, 18: 4794-4797 (2008).
Scott, David A., et al., Bioorganic & Medicinal "Identification of 3-amido-4-anilinoquinolines as potent and selective inhibitors of CSF-1R kinase", Chemistry Letters, 19: 697-700 (2009).
Shi, C. and E.G. Pamer, "Monocyte recruitment during infection and inflammation," Nat. Rev. Immunol., 11(11): 762-774 (2011).
Sun, Li, et al., "Synthesis and Biological Evaluations of 3-Substituted Indolin-2-ones: A Novel Class of Tyrosine Kinase Inhibitors That Exhibit Selectivity toward Particular Receptor Tyrosine Kinases", J. Med. Chem., 41: 2588-2603 (1998).
Sussman, E.M. et al., "Porous implants modulate healing and induce shifts in local macrophage polarization in the foreign body reaction," Annals of Biomedical Engineering, 42(7): 1508-1516 (2014).
Tuch, B.E. et al., "Safety and viability of microencapsulated human islets transplanted into diabetic humans," Diabetes Care, 32(10): 1887-1889 (2009).
Vegas, A.J. et al., "Combinatorial hydrogel library enables identification of materials that mitigate the foreign body response in primates," Nat. Biotechnol., 34(3): 345-352 (2016).
Veiseh, O. et al., "Size- and shape-dependent foreign body immune response to materials implanted in rodents and non-human primates," Nature Materials, 14(6): 643-651 (2015).
Vuga, L.J., et al., "C-X-C motif chemokine 13 (CXCL13) is a prognostic biomarker of idiopathic pulmonary fibrosis," American Journal of Respiratory and Critical Care, 189(8): 966-974 (2014).
Wall, Mark J., et al., "Synthesis and evaluation of novel 3,4,6-substituted 2-quinolones as FMS kinase inhibitors", Bioorganic & Medicinal Chemistry Letters, 18: 2097-2102 (2008).
Ward, Kenneth W., "A Review of the Foreign-body Response to Subcutaneouslyimplanted Devices: The Role of Macrophages and Cytokines in Biofouling and Fibrosis," J. Diabetes Sci. Technol. Online, 2: 768-777 (2008).
Weir, G.C., "Islet encapsulation: advances and obstacles," Diabetologia, 56(7): 1458-1461 (2013).
Williams, D.F., "On the mechanisms of biocompatibility," Biomaterials, 29(20): 2941-2953 (2008).
Wong, W. et al., "2005 immunosuppressive strategies in kidney transplantation: which role for the calcineurin inhibitors?" Transplantation, 80(3): 289-296 (2005).
Wood, K.J., et al., "Regulatory immune cells in transplantation," Nat. Rev. Immunol., 12(6): 417-430 (2012).
Wynn, T.A. and T.R. Ramalingam, "Mechanisms of fibrosis: therapeutic translation for fibrotic disease," Nature Medicine, 18(7): 1028-1040 (2012).
Zhang, Chao, et al., "Design and pharmacology of a highly specific dual FMS and KIT kinase inhibitor," PNAS, 110(14): 5689-5694 (2013).
Final Office Action for U.S. Appl. No. 16/081,654, "Methods of Preventing or Reducing a Fibrotic Response Using CSF1R Inhibitors", dated Jan. 7, 2020.
International Preliminary Report on Patentability for Int'l Application No. PCT/US2017/025991, titled: Methods of Preventing or Reducing a Fibrotic Response Using CSF1R Inhibitors, dated Oct. 18, 2018.
International Search Report and Written Opinion for Int'l Application No. PCT/US2017/025991, titled: Methods of Preventing or Reducing a Fibrotic Response Using CSF1R Inhibitors, dated Jun. 21, 2017.
Non-Final Office Action for U.S. Appl. No. 16/081,654, "Methods of Preventing or Reducing a Fibrotic Response Using CSF1R Inhibitors", dated Jun. 25, 2019.

\* cited by examiner

Crystalline Curcumin Loaded Capsules (20-30μm Crystals size)
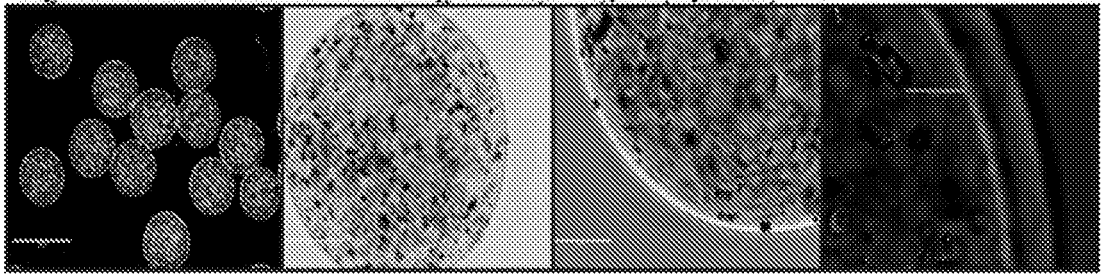
Amorphous Curcumin Loaded Capsules
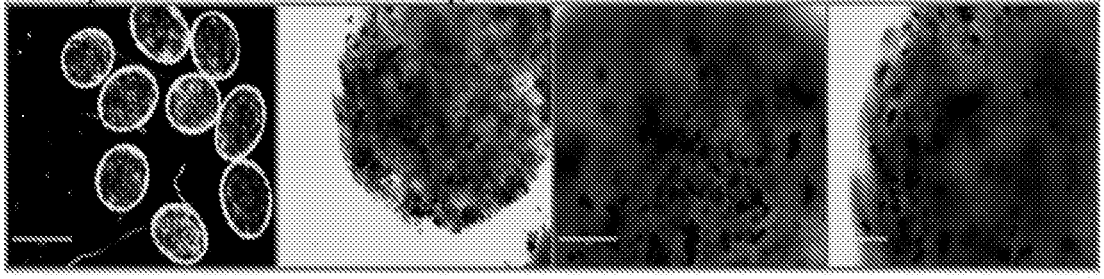
Crystalline-Amorphous Curcumin Loaded Capsules
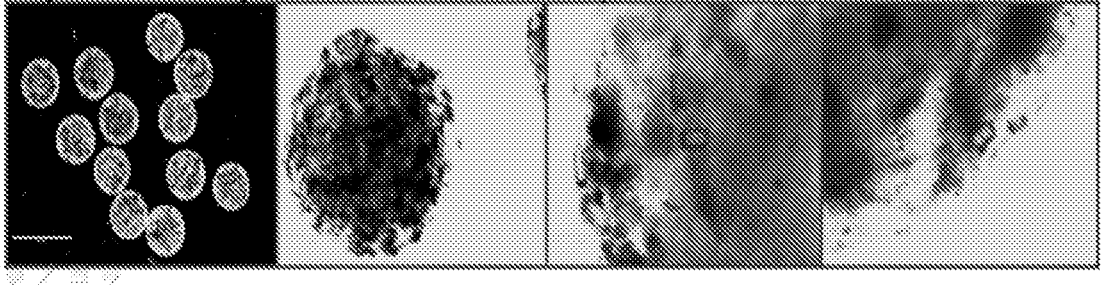
FIG. 4

*** - One-way ANOVA with p<0.0001

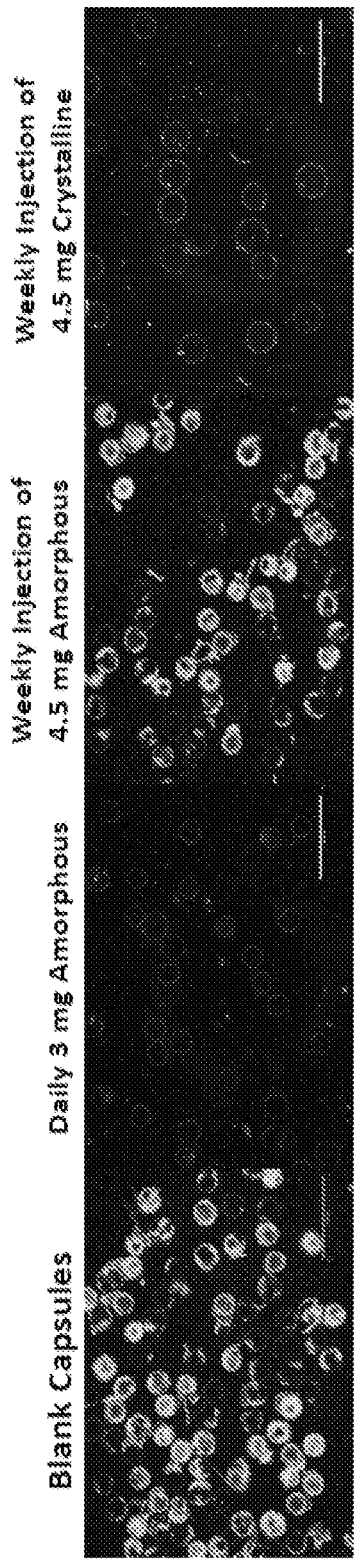
FIG. 17A
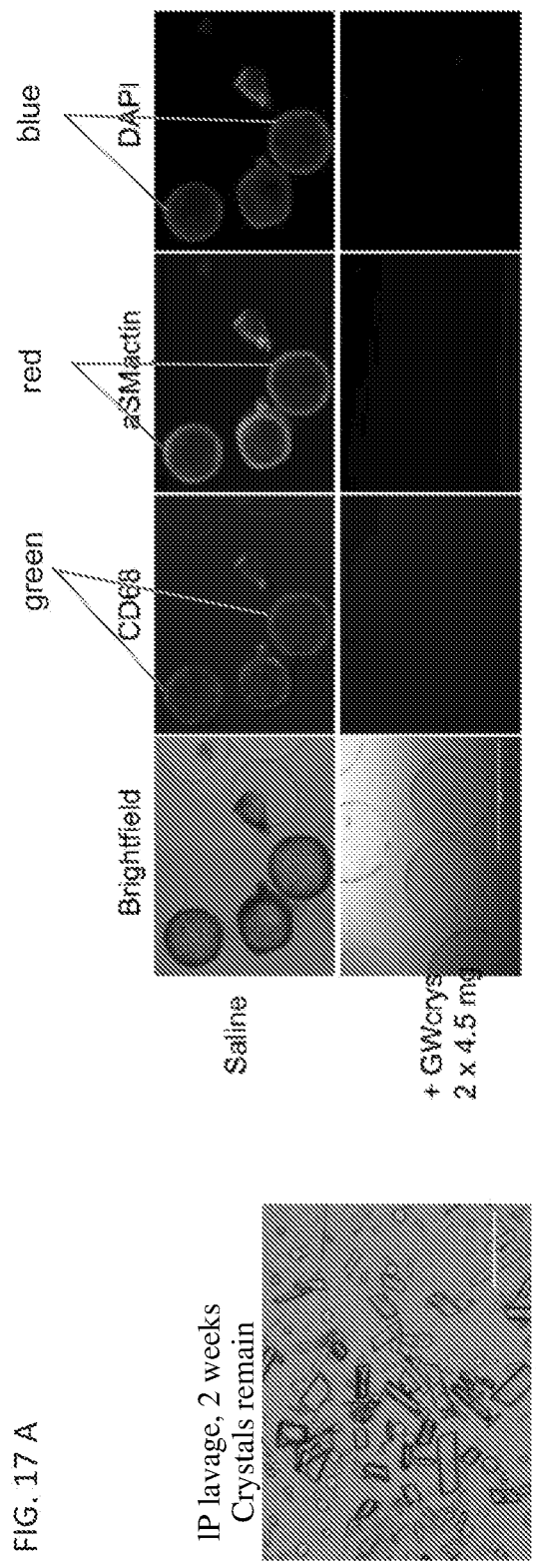
FIG. 17C
IP lavage, 2 weeks
Crystals remain
FIG. 17B

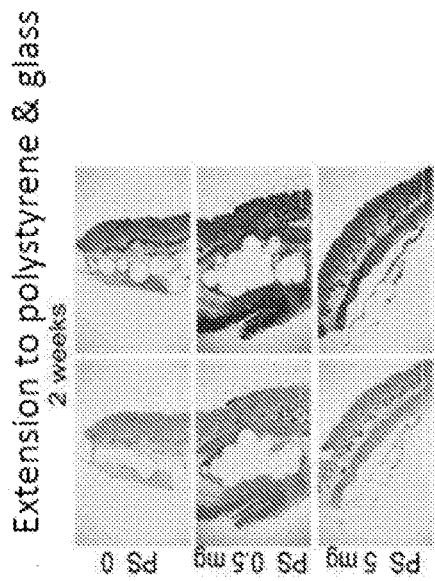
FIG. 17D
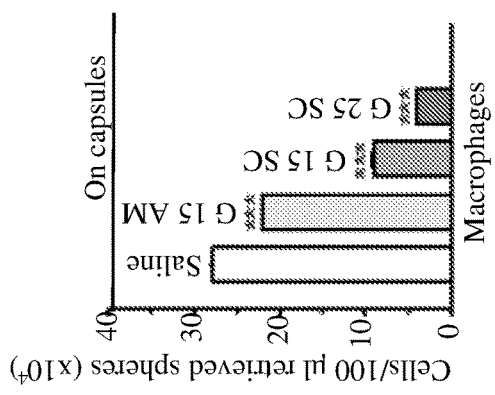
FIG. 17F
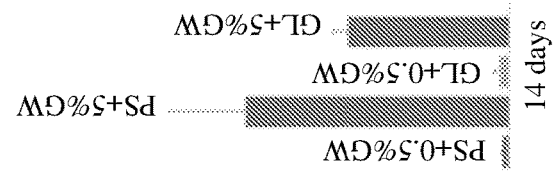
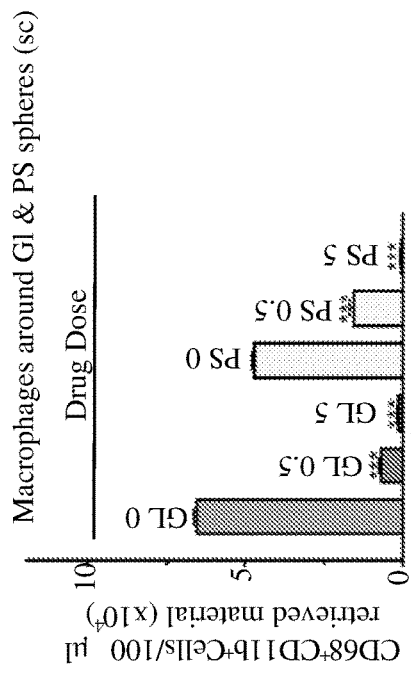
FIG. 17E
FIG. 17G

Method I Twinning

Crystals Projection

Method II

Method II: Crystalline Lattice
non-hydrogen atom volume: 16.7 A^3

Crystallization Techniques
Method I - Solvent   Method II - Solvent/Anti
Evaporation          solvent mixture Method III
Crystal Size:
30 μm 100μm 500 μm 1000 μm

| Empirical formula: | C₂₀H₂₂N₄O₃ |
|---|---|
| a: | 5.449 Å |
| b: | 9.686 Å |
| c: | 17.653 Å |
| α (alpha): | 77.11 ° |
| β (beta): | 87.58 ° |
| γ (gamma): | 84.08 ° |
| Volume: | 903.21 Å³ |
| Space group: | P-1 |
| Calculated density: | 1.347 g/cm³ |
| Color: | yellow |
| Z: | 2 |
| Temperature: | -173.0 °C |
| Formula weight: | 366.420 g/mole |
| R(F): | 0.0412 |
| Rw(F): | 0.1146 |
| non-hydrogen atom volume: | 16.7 A^3 |

Amorphous GW2580
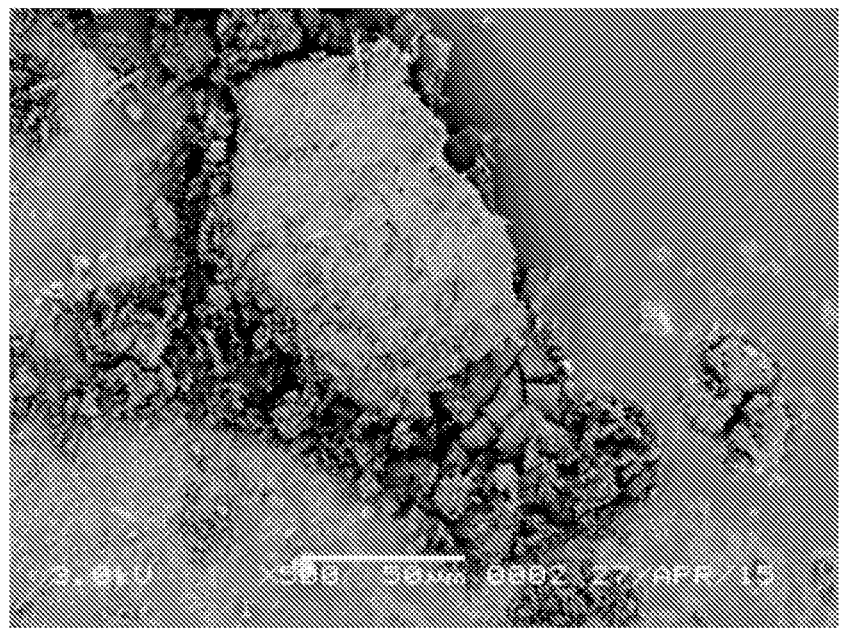
Crystalline GW2580
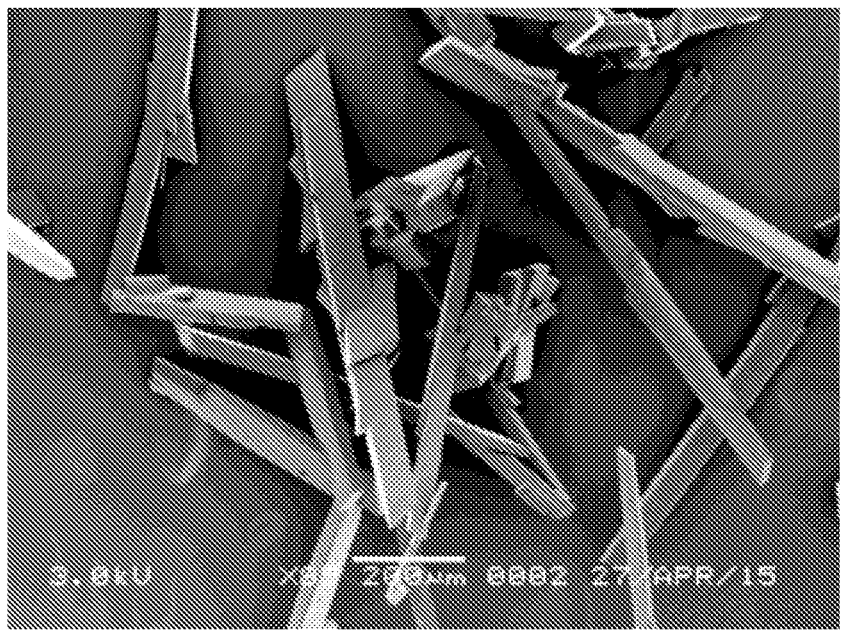
FIG. 20B

PXRD simulated
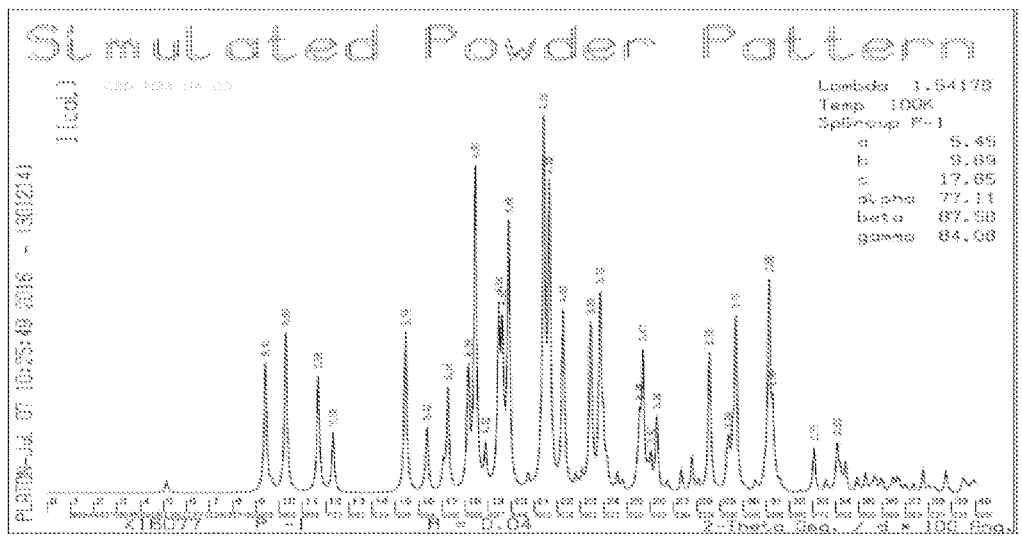
Found: Single polymorph verified
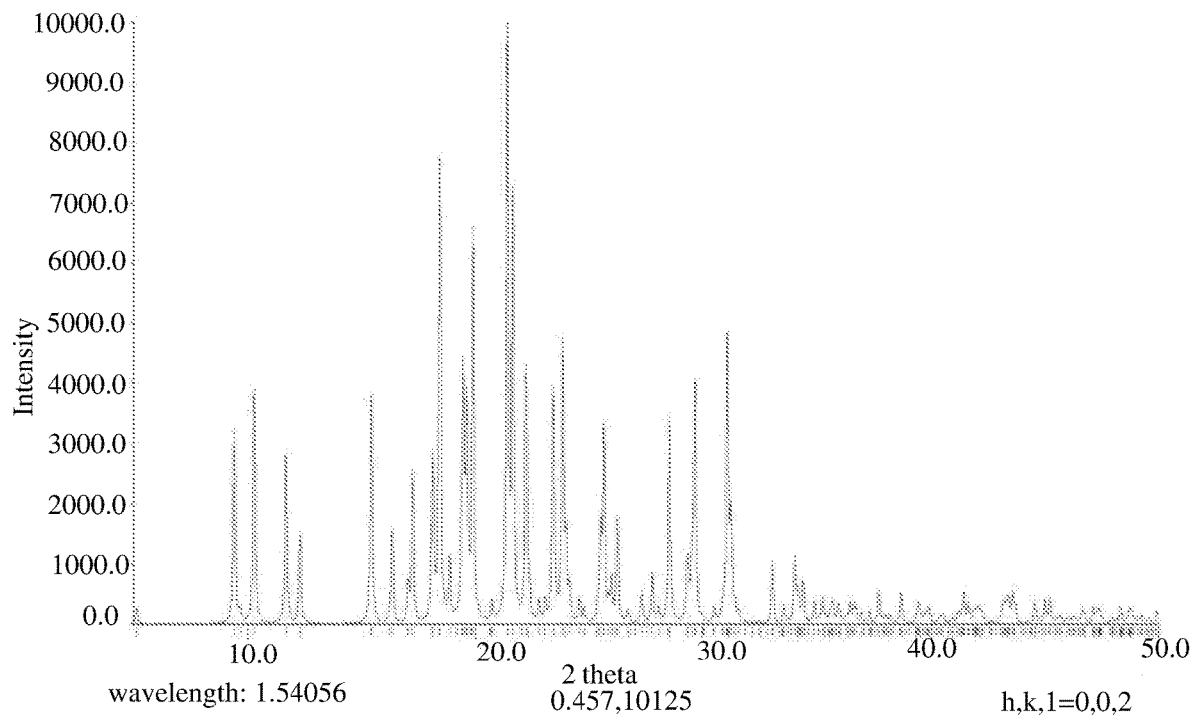
FIG. 20C

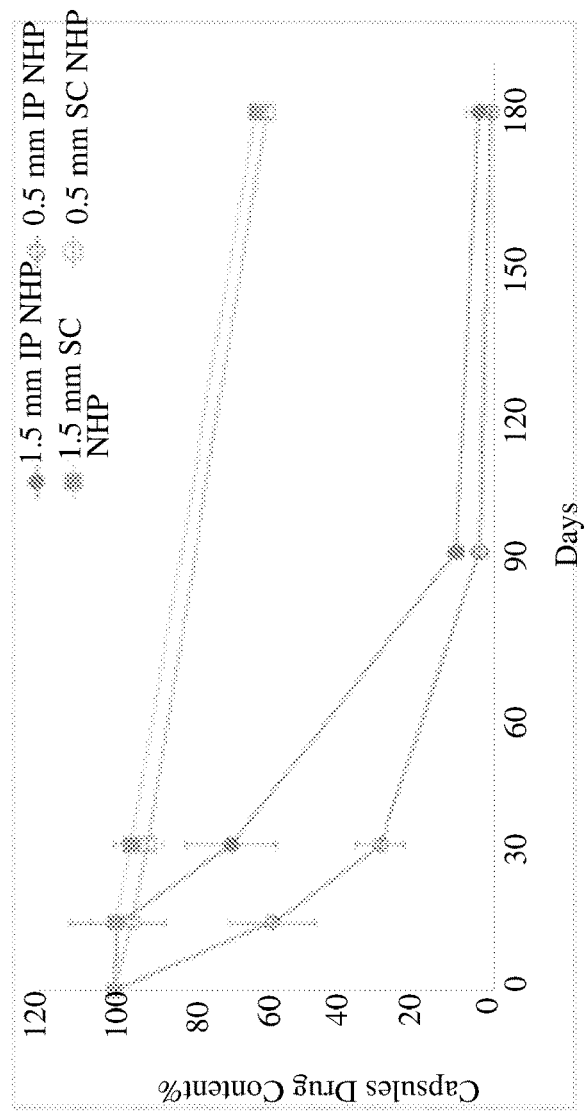
FIG. 23A
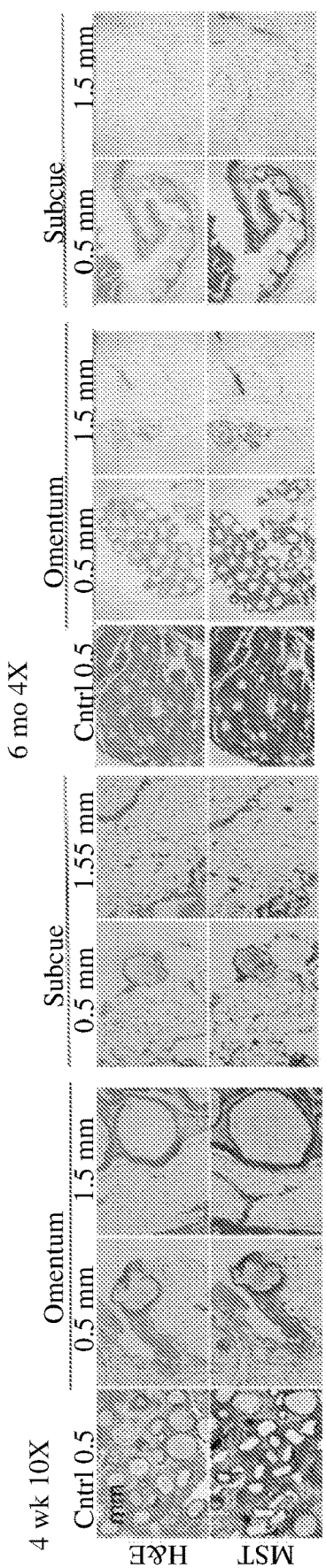
FIG. 23B
FIG. 23C

** - One-way ANOVA with p<0.001
*** - One-way ANOVA with p<0.0001

SEQUENCE LISTING

<160> NUMBER OF SEQ ID NOS: 8

<210> SEQ ID NO 1
<211> LENGTH: 20
<212> TYPE: DNA
<213> ORGANISM: Artificial
<220> FEATURE:
<223> OTHER INFORMATION: oligonucleotide primer

<400> SEQUENCE: 1
gaaatccacc aaagctcacg                                       20

<210> SEQ ID NO 2
<211> LENGTH: 18
<212> TYPE: DNA
<213> ORGANISM: Artificial
<220> FEATURE:
<223> OTHER INFORMATION: oligonucleotide primer

<400> SEQUENCE: 2
cgggttccgc tgtgtaag                                         18

<210> SEQ ID NO 3
<211> LENGTH: 19
<212> TYPE: DNA
<213> ORGANISM: Artificial
<220> FEATURE:
<223> OTHER INFORMATION: oligonucleotide primer

<400> SEQUENCE: 3
ctctcgtgcc atgtgaacc                                        19

<210> SEQ ID NO 4
<211> LENGTH: 22
<212> TYPE: DNA
<213> ORGANISM: Artificial
<220> FEATURE:
<223> OTHER INFORMATION: oligonucleotide primer

<400> SEQUENCE: 4
ttctctaaat tggtcccagg aa                                    22

<210> SEQ ID NO 5
<211> LENGTH: 22
<212> TYPE: DNA
<213> ORGANISM: Artificial
<220> FEATURE:
<223> OTHER INFORMATION: oligonucleotide primer

<400> SEQUENCE: 5
gcttctttgc agctccttcg tt                                    22

<210> SEQ ID NO 6
<211> LENGTH: 20
<212> TYPE: DNA
<213> ORGANISM: Artificial
<220> FEATURE:
<223> OTHER INFORMATION: oligonucleotide primer

<400> SEQUENCE: 6
cggagccgtt gtcgacgacc                                       20

<210> SEQ ID NO 7
<211> LENGTH: 22
<212> TYPE: DNA
<213> ORGANISM: Artificial

```
<220> FEATURE:
<223> OTHER INFORMATION: oligonucleotide primer

<400> SEQUENCE: 7
accttcttgc agctcctccg tc                                              22

<210> SEQ ID NO 8
<211> LENGTH: 20
<212> TYPE: DNA
<213> ORGANISM: Artificial
<220> FEATURE:
<223> OTHER INFORMATION: oligonucleotide primer

<400> SEQUENCE: 8
cggagccgtt gtcgacgacg                                                 20
```

COMPOSITIONS OF CRYSTALLIZED HYDROPHOBIC COMPOUNDS AND METHODS OF MAKING AND USING SAME

RELATED APPLICATIONS

This application is the U.S. National Stage of International Application No. PCT/US2017/026009, filed on Apr. 4, 2017, published in English, which claims the benefit of U.S. Provisional Application No. 62/318,208, filed on Apr. 4, 2016, and claims the benefit of U.S. Provisional Application No. 62/317,831, filed on Apr. 4, 2016. The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:
  a) File name: 00502293002_Seq_Listing.txt; created Oct. 4, 2018, 2 KB in size.

BACKGROUND

Crystallization is a complex thermodynamic and kinetic process. Key elements include, for example, the level of supersaturation, incubation time, solvent conditions, the type and intensity of mixing, the concentration and size of seeds, and temperature. Certain properties of crystals such as morphology, size distribution, and polymorphism create diversity in crystalline populations and make them suitable for certain applications. Crystals of organic compounds have important applications in many fields, such as pharmaceuticals, semiconductors, nutraceuticals, diagnostics, agriculture, textiles and cosmetics. In these fields, preparing an agent in a crystalline form can impart desirable properties such as chemical stability, controlled release kinetics, localized delivery and reproducibility, among others.

Although techniques exist for preparing crystals of hydrophobic compounds, some methods do not control the critical parameters of morphology, size distribution, and polymorphism. As a result, the crystals of hydrophobic compounds produced by these methods are either polydisperse, exhibit polymorphism or are unstable. Such crystals are not suitable for certain specialized applications, for instance, controlled drug delivery applications. Other methods produce crystals of inconsistent sizes, which is undesirable for many applications.

Crystals of hydrophobic compounds are often used as therapeutic agents. For such therapeutic applications, crystallization processes must be carried out under strict environmental control to meet stringent physical and chemical specifications. Formulations with crystalline carpet/coatings, crystalline slurries and quasi-crystalline materials are known in the art. However, these crystalline carpet/coatings or slurries are not generally reliable for certain sustained release applications.

Accordingly, there is a need for compositions of crystallized hydrophobic compounds wherein critical parameters of crystal size distribution and polymorphism are controlled. There is also a need for methods and processes for preparing and using such compositions.

SUMMARY OF THE INVENTION

The present invention is based, in part, on the discovery that compositions comprising a uniform population of free single crystals have certain advantageous properties that are applicable to diverse technologies, and on the development of improved processes for preparing such uniform populations of free single crystals.

Thus, in one embodiment, the invention provides a composition comprising a uniform population of free, single crystals of a hydrophobic compound that have a characteristic dimension of at least about 1 micrometer. In one embodiment, the invention provides a composition consisting essentially of a uniform population of free, single crystals of a hydrophobic compound that have a characteristic dimension of at least about 1 micrometer. In one embodiment, each free single crystal in the composition of the crystallized hydrophobic compound, exhibits the same polymorph.

The invention provides, in additional embodiments, methods of delivering to a subject in need thereof a uniform population of free single crystals of a hydrophobic compound. The methods generally comprise the steps of administering to the subject a composition comprising an effective amount of a uniform population of free single crystals of a first hydrophobic compound, wherein each free, single crystal in the population has a characteristic dimension of greater than about 1 micrometer. In a particular embodiment, the method of the invention includes administering the uniform population of free single crystals of a hydrophobic compound to a human subject to treat or to prevent an inflammatory condition, such as fibrosis.

In another embodiment, the invention describes a method for providing a sustained release of a hydrophobic compound in a subject in need thereof, comprising administering to the subject a composition comprising a uniform population of free, single crystals of a first hydrophobic compound, wherein each free, single crystal in the population has a characteristic dimension of greater than about 1 micrometer.

In yet another embodiment, the present invention provides a uniform population of free, single crystals of a hydrophobic compound, produced according to a process that comprises (a) providing a solution consisting essentially of the hydrophobic compound in a solvent, (b) forming a mixture by adding to the solution an anti-solvent in an amount sufficient to induce formation of the free, single crystals and not exceeding the amount of anti-solvent that causes the compound to precipitate from the solvent, and (c) harvesting the free, single crystals.

The invention further provides, in another embodiment, a process for preparing a uniform population of free, single crystals of a hydrophobic compound, which process comprises (a) providing a solution consisting essentially of the hydrophobic compound in a solvent, (b) forming a mixture by adding to the solution an anti-solvent in an amount sufficient to induce formation of the free, single crystals and not exceeding the amount of anti-solvent that causes the compound to precipitate from the solvent, and (c) harvesting the free, single crystals.

In one embodiment, the invention provides a composition comprising a polymorph of a hydrophobic compound that is characterized by a powder x-ray diffraction pattern substantially in accordance with FIG. 20 C. In this embodiment, the polymorph is characterized by at least five major powder x-ray diffraction peaks at 2θ angles selected from 18.42°, 19.46°, 19.88°, 21.4°, 21.64°, 22.22°, 23.82°, 29.64° and 31.08°.

In yet another embodiment, the present invention provides a method of preparing a polymorph of a hydrophobic compound, the method comprises (a) providing a solution consisting essentially of the hydrophobic compound in a solvent, (b) forming a mixture by adding to the solution an anti-solvent in an amount sufficient to induce formation of the free, single crystals and not exceeding the amount of anti-solvent that causes the compound to precipitate from the solvent, and (c) harvesting the free, single crystal polymorph.

The compositions, methods and processes described herein provide uniform populations of free single crystals of hydrophobic compounds that have certain advantageous properties, including, but not limited to, increased chemical stability, homogeneity and adaptability for use in various technologies.

BRIEF DESCRIPTION OF THE DRAWINGS

U.S. Provisional Application No. 62/318,208 ('208 application) contains color drawings which correspond to drawings in the instant application. With regard to indications of color within the instant description of the figures provided herein, reference is made to those corresponding drawings and associated descriptions of the '208 application.

FIG. 4. A representative macroscale example of broad-spectrum anti-inflammatory curcumin encapsulated in alginate microspheres: crystalline (top), amorphous (middle), or a hybrid of both crystalline and amorphous formulations (bottom). Left to right: increasing order of magnification.

FIG. 17A. Long-term drug depot effect possible with naked (non-encapsulated) drug crystals. GW2580 was used in this study. Saline or naked crystals of formulated GW2580 were injected intraperitoneally after 500 μm alginate spheres were implanted IP in C57BL/6 mice. As opposed to dirty control capsules (left), where saline was injected, only daily amorphous drug (3 mg/day for a total of 45 mg over 2 weeks) or a much smaller weight amount of drug crystals (4.5 mg, once per week, for 9 mg total) were able to prevent fibrosis and keep capsules clean. Weekly amorphous drug was not effective, suggesting that the fine powder, capable of achieving a burst release, did not provide a similar reservoir for persistent drug release and extended anti-macrophagic/anti-fibrotic inhibition activity.

FIG. 17B. DIC imaging of IP lavage liquid rinsed from mice 2 weeks after material implantation, and 1 week since the last naked crystal injection. Many large crystals remained within the IP space one week beyond delivery, indicating a long-term drug release reservoir even with non-encapsulated naked crystalline drug.

FIG. 17C. Fluorescence microscopy showing fibrotic overgrowth or lack thereof on alginate spheres retrieved from C57BL/6 mice treated with saline (control) or naked GW2580 drug crystals (Blue, DAPI nuclear stain; Green, Macrophage CD68; and Red, Fibrosis marker α-smooth muscle actin). Brightfield images of the same fields of view also shown.

FIG. 17D. Quantitative FACS analysis performed on cells dissociated directly off of alginate spheres. Naked drug crystals reduce macrophage presence (left).

FIG. 17E. H&E and Masson's Trichrome stained histological sections of excised SC tissue 2 weeks post-implant showing reduced fibrosis of implanted 500 μm polystyrene (PS) spheres co-injected with naked crystalline drug GW2580 (0.5 or 5 mg total/SC site), as compared to saline (no drug) controls (Scale bar=1000 μm; 4×).

FIG. 17F. FACS analysis performed on cells dissociated from SC-implanted polystyrene (PS) and glass (GL) spheres, retrieved after 2 weeks post-implantation. Naked crystalline GW2580 significantly reduced macrophage presence in all cases. Data: mean±SEM, n=5. Statistical analysis: one-way ANOVA with Bonferroni multiple comparison correction *: $p<0.05$; : $p<0.001$, and *: $p<0.0001$; ns=not significantly different. Experiments repeated at least 2 times.

FIG. 17G. Drug extraction analysis from implantation site nearby tissue in the experiment reported in FIG. 17E and FIG. 17F. Analysis proves crystalline formulation drug long release ability in the naked form.

FIG. 20B. Scanning-electron microscope (SEM) images confirm of the GW2580 amorphous material and the uniform crystals.

FIG. 20C. Powder X-ray diffraction (PXRD) polymorph profiles (left image: simulated vs. right image: measured) of GW2580 crystals prepared by the method of the invention using a solvent:antisolvent mixture (Method II). The data confirm the presence of a single polymorph. Experiments were repeated 2 times.

FIG. 23A. Drug extraction analysis (HPLC) of alginate spheres encapsulating crystalline CSF1R inhibitor GW2580 shown in FIG. 12 revealed a significant quantity of drug left inside the retrieved capsules (1.5 mm capsules: SC-■ profile & IP-● profile, 0.5 mm capsules: SC-□ profile & IP-○ profile).

FIG. 23B. H&E and Masson's Trichrome stained histological sections of excised intraperitoneal omentum or subcutaneous (subcue) tissue 4 weeks post-implant showing reduced fibrosis in various crystalline drug groups, as compared to blank (no drug) control spheres (Scale bar=1000 µm (4×) or 400 µm (10×), respectively).

FIG. 23C. H&E and Masson's Trichrome stained histological sections of excised intraperitoneal omentum or subcutaneous (subcue) tissue 6 months post-implant showing reduced fibrosis in various crystalline drug groups, as compared to blank (no drug) control spheres (Scale bar=1000 µm (4×) or 400 µm (10×), respectively).

DETAILED DESCRIPTION OF THE INVENTION

Figure 1:
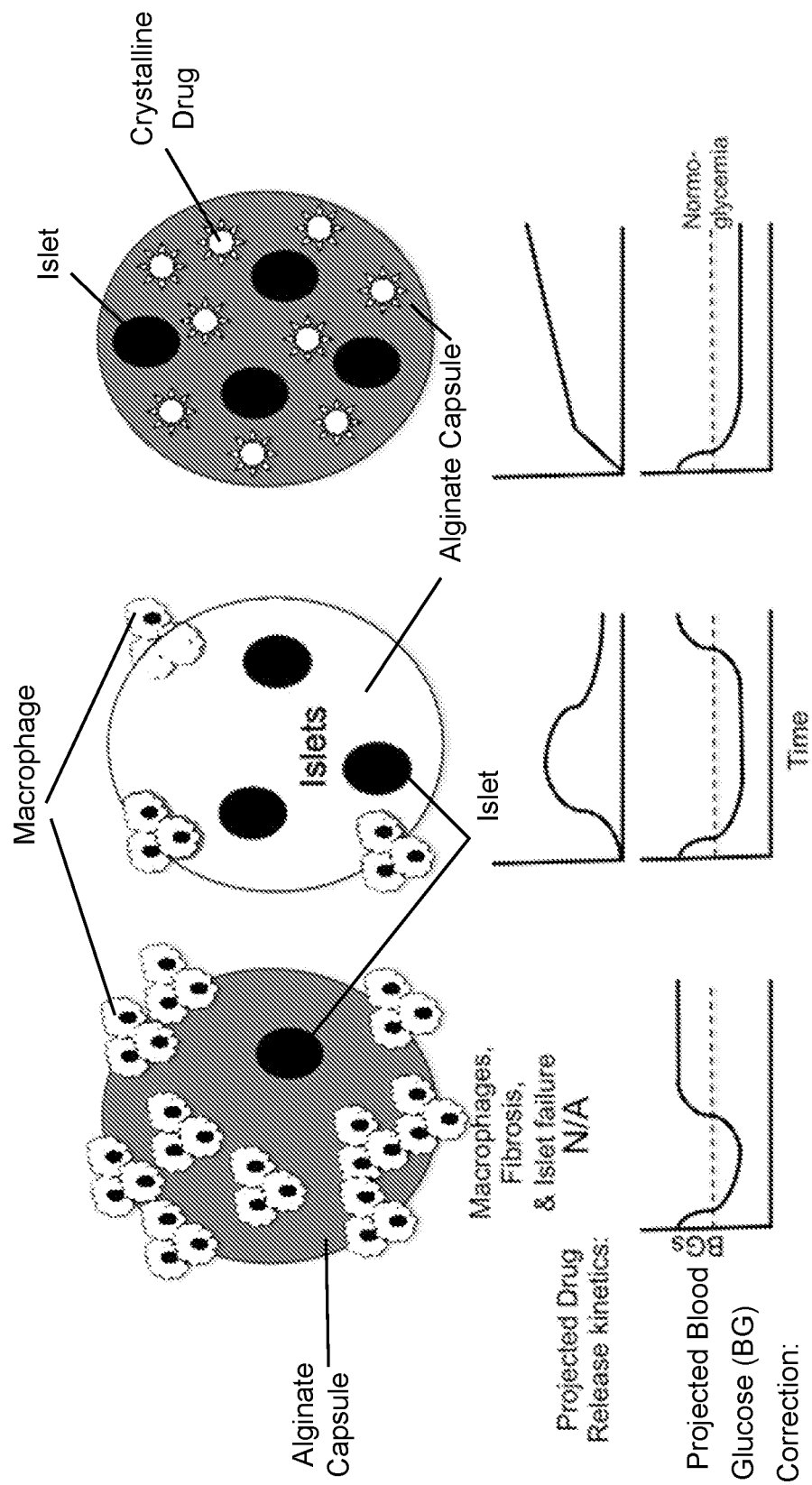
FIG. 1A is a model schematic showing varying fibrotic response and host rejection of implanted devices (e.g., alginate capsules bearing encapsulated islets for diabetes therapy) with no co-encapsulated drug.
FIG. 1B is a model schematic showing varying fibrotic response and host rejection of implanted alginate capsules bearing encapsulated islets with liquid-dispersed or amorphous (fine powder) drug.
FIG. 1C is a model schematic showing varying fibrotic responses and host rejection of implanted alginate capsules bearing encapsulated islets with crystalline drug, capable of slower, yet elongated drug release kinetics.

Compositions Comprising Uniform Populations of Free, Single Crystals

A description of example embodiments of the invention follows below; additional description of the methods of treating inflammatory conditions (e.g., fibrosis) is found in International Application No. PCT/US2017/025991, entitled "METHODS OF PREVENTING OR REDUCING A FIBROTIC RESPONSE USING CSF1R INHIBITORS", filed concurrently with the instant application on Apr. 4, 2017, the contents of which are incorporated herein by reference in entirety.

The present invention, in certain embodiments, provides a composition comprising a uniform population of free, single crystals of a hydrophobic compound, wherein each free, single crystal in the population has a characteristic dimension of at least about 1 micrometer. As used herein, "population" means any finite number of two or more crystals. In one embodiment the population contains a finite number of free, single crystals that is subject to statistical analysis.

The expression "uniform population" refers to a population of crystals wherein the characteristic dimension of each crystal in the population is within 25% (e.g., within about 1%, about 2%, about 5%, about 10%, about 15%, about 20%, about 24%) of the median characteristic dimension of the crystals within the population.

"Characteristic dimension," as used herein, refers to a dimension of a crystal that can be measured, for example, by known methods used in the art, including, e.g., microscopy. For spherical crystals, the characteristic dimension is the diameter of the crystal. For non-spherical crystal morphologies, the characteristic dimension of a single crystal can be any dimension selected from the crystal's length, width and height, randomly assigned X, Y, and Z, respectively, including the following options (X=Y=Z), (≠Y≠Z), (X=Y, X≠Z), (X=Z, X≠Y), (X≠Z, Y=Z)). In accordance with the invention, at least one characteristic dimension (e.g., diameter, length, width, height) of a crystal must be at least about 1 µm.

The expression "free, single crystal," as used herein, refers to a crystalline material that is not attached to any surface, in which the crystal lattice of the entire sample is continuous and unbroken and lacks grain boundaries.

The terms "crystal," "crystals," "crystalline," and "crystallized," or phrase "crystalline form," refer to matter whose constituent atoms, molecules or ions are arranged in a substantially uniform, repeating three-dimensional pattern. The pattern can be detected according to known methods used in the chemical arts, including, for example, visual identification of crystals and identification through X-ray diffraction (e.g., Powder X-Ray Diffraction (PXRD) and Single-crystal X-Ray Diffraction (SXRD)).

The crystals in the compositions of the invention can be of varying size and shape. For example, crystals in a uniform population can be any shape, including, but not limited to, spheres, cubes, rods, and hexagons. Crystals in a uniform population can all have the same shape, including, but not limited to, spheres, cubes, rods, and hexagons. In some embodiments, the crystals in a uniform population exhibit the same polymorph (also referred to in the art as "isomorph"). The term "polymorph", as used herein, refers to crystals exhibiting "polymorphism", a property of a substance to exist in different crystalline forms (e.g., momoclinic, hexagonal, rhombohedral, cubic). It is known in the art that polymorphic crystals differ in their physical properties and crystals of the same compound that exhibit the same polymorph (e.g., isomorphous crystals) typically have similar physical properties (e.g., dissociation kinetics).

In one embodiment, the uniform population comprises free single crystals, wherein all or a substantial majority (e.g., at least about 90%) of crystals in the population exhibit a single polymorph. In a different embodiment, the uniform population comprises free single crystals, wherein all (e.g., about 100%, about 99%, about 95%, about 90%, about 85%, about 80%, about 75%) of crystals in the population exhibit a single polymorph. In another embodiment, the uniform population comprises free single crystals that exhibit different crystalline forms (or polymorphs).

Figure 6:
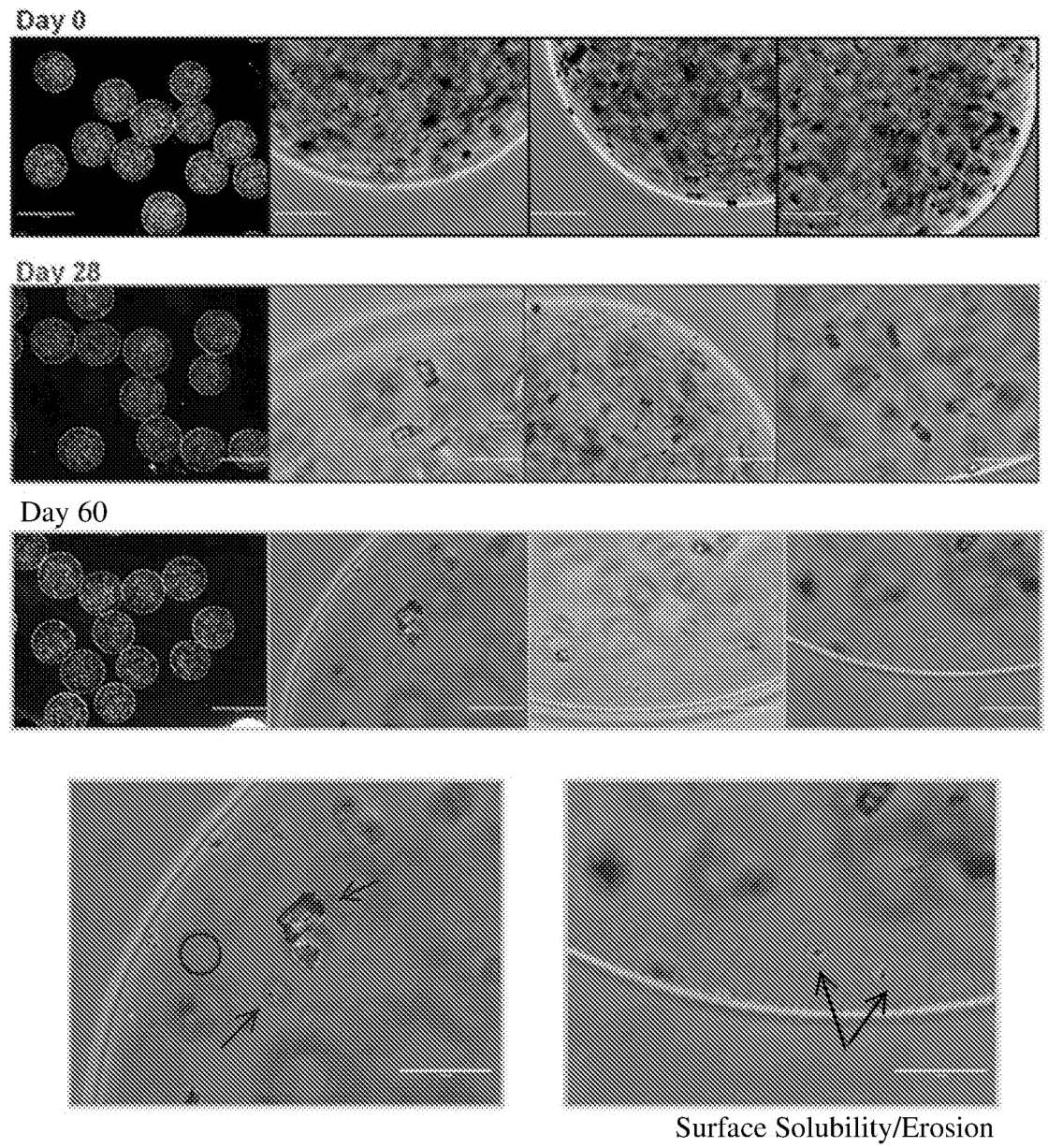
FIG. 6. Representative microscope images showing slow surface erosion and long-term release (over at least 2 months) of crystalline curcumin loaded into alginate spheres. Smaller crystals leave behind empty spaces within the 3D alginate (circle and arrows), whereas larger crystals remain longer exhibiting surface release/erosion.

In a particular embodiment, the invention provides a composition comprising at least two (e.g., 2, 3, 4, 5, etc.) uniform populations of free single crystals of a hydrophobic compound, wherein each population has a different characteristic dimension for a given crystal dimension. For instance, FIG. 6 shows representative microscopic images of a composition comprising at least two different uniform populations of free single crystals of the same hydrophobic compound, curcumin, where the population of smaller crystals has a higher dissolution rate than the population of larger crystals.

In a further embodiment, the invention provides a composition comprising at least two different hydrophobic compounds, each provided as a uniform population of free single crystals, wherein the two or more populations have substantially identical median characteristic dimensions (e.g., within about 10% of the median characteristic dimension of one another). In a particular embodiment of the invention, the two or more populations have substantially identical characteristic dimensions and exhibit the same polymorph. In yet another embodiment, the two or more populations have different characteristic dimensions. In a further embodiment, the two or more populations have different characteristic dimensions but exhibit the same polymorph. In another embodiment, the two or more populations have different characteristic dimensions and exhibit different polymorphs.

Crystals can be of any size, including, but not limited to the sizes described hereinafter. For example, the crystals can have at least one dimension in the range of at least about 1 µm to about 1 cm (e.g., about 5, about 10, about 50, about 100, or about 500 µm, at least about 1, about 5, about 50, about 100, or about 500 mm). Crystals in a uniform population can all have the same size, including, but not limited to, having at least one dimension in the range of about 1 µm to about 1 cm (e.g., at least about 5, 10, 50, 100, or 500 µm, at least about 1, 5, 50, 100, or 500 mm). In some embodiments, crystals in a uniform population can all have the same size, including, but not limited to, having three equal dimensions (i.e., X=Y=Z) in the range of about 1 µm to about 1 cm (e.g., at least about 5, 10, 50, 100, or 500 µm, at least about 1, 5, 50, 100, or 500 mm). In certain embodiments, the crystals have a characteristic dimensions that is at least about 1 cm (e.g., at least about 1.5 cm, at least about 2 cm, at least about 3 cm).

Crystal sizes can be determined using any method known in the art, including, but not limited to, conventional microscopy, Scanning Electron Microscopy (SEM), Transmission Electron Microscopy (TEM), X-ray diffraction (XRD), Raman spectroscopy, photon correlation spectroscopy, Differential Scanning calorimetry (DSC), and Dynamic Light Scattering (DLS).

"Hydrophobic compound", as used herein, refers to an organic compound characterized by solubility in an aqueous medium of greater than or equal to 30 parts of solvent required per part of solute according to United States Pharmacopeia (USP) and British Pharmacopeia (BP) solubility criteria (Table 1).

TABLE 1

USP and BP solubility criteria.

| Descriptive term | Part of solvent required per part of solute |
|---|---|
| Very soluble | Less than 1 |
| Freely soluble | From 1 to 10 |
| Soluble | From 10 to 30 |
| Sparingly soluble | From 30 to 100 |
| Slightly soluble | From 100 to 1000 |
| Very slightly soluble | From 1000 to 10,000 |
| Practically insoluble | 10,000 and over |

In some embodiments, the hydrophobic compound of the current invention has a molecular weight in the range from about 200 to about 600 Daltons.

Hydrophobic compounds that are suitable for use in the compositions of the present invention include, but are not limited to, inorganic, organic and organometallic compounds. In particular embodiments, the hydrophobic compounds are organic compounds, including biologically-active and non-active organic compounds. Such compounds include, but are not limited to, nutraceuticals, pesticides, herbicides, fragrances, anticoagulants, dyes, cosmetics, catalysts, flavors, foods, fuels, emulsions and the like.

Biologically-active hydrophobic compounds, as used herein, are compounds which have a desired effect (e.g., therapeutic or pharmacologic) on a desired biological target (e.g., live cell, tissue or a protein). The desired effect on a desired biological target can be observed in vitro (e.g., fixed cell), in vivo (e.g., in a subject in need thereof) or ex-vivo (e.g., live cell such as islet cells). Biologically-active hydrophobic compounds include, without limitation, for example, anti-inflammatory; antihemorrhagic; antiproliferative; antineutropenic; antiangiogenic; anti-osteoporotic; antianalgesic; antiparasitic; anti-arthritic; anti-asthmatic; anti-atherosclerotic; antibacterial; antihistamine; anticoagulant; anticonvulsant; antifungal; anti-infective; antimicrobial; antimigraine; antimitotic; antirheumatic; antiviral; appetite suppressant; fibrinolytic; immunomodulatory; immunoregulatory; immunostimulatory; cytotoxic; and immunosuppressant compounds, as well as imaging agents (e.g., fluorescent agents); and immunizing agent s (e.g., vaccines). Hydrophobic compounds also include anti-cancer agents, e.g., paclitaxel, doxirubicin.

In particular embodiments, biologically active hydrophobic compounds include agents targeting one or more of the following biological molecules: Tumor Necrosis Factor alpha (TNFα), Tumor Growth Factor beta (TGFβ) and Colony-Stimulating Factor 1 Receptor (CSF1R).

In one embodiment, the hydrophobic compound targeting CSF1R is 5-[[3-Methoxy-4-[(4-methoxyphenyl)methoxy]phenyl]methyl]-2,4-pyrimidinediamine (also referred to as GW2580 or GW) having the chemical formula:

(I)

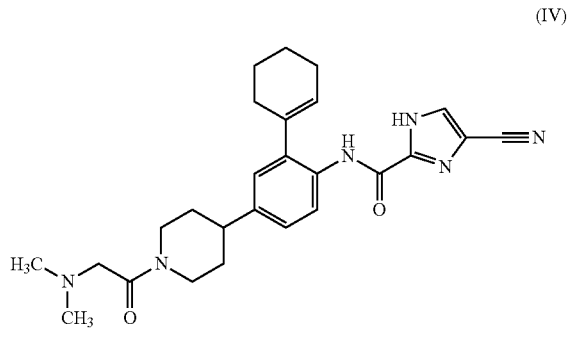

or a salt thereof.

In another embodiment, the hydrophobic compound targeting CSF1R is N-[4-[(6,7-Dimethoxy-4-quinolinyl)oxy]-2-methoxyphenyl]-N'-[1-(2-thiazolyl)ethyl]urea (also referred to as Ki20227) having the chemical formula:

(II)

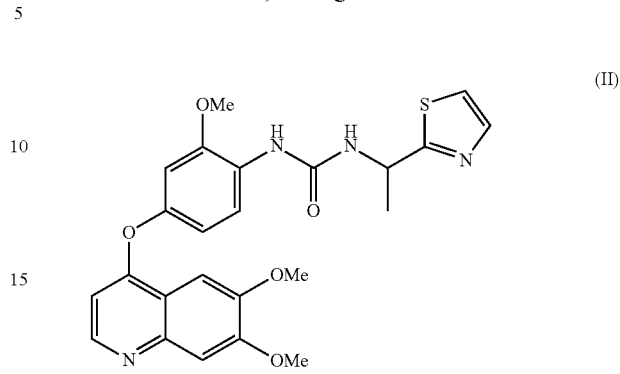

or a salt thereof.

In another embodiment, the hydrophobic compound targeting CSF1R is 4-(3,4-Dimethylanilino)-7-(4-(methylsulfonyl)phenyl)quinoline-3-carboxamide (also referred to as cFMS receptor inhibitor III) having the chemical formula:

(III)

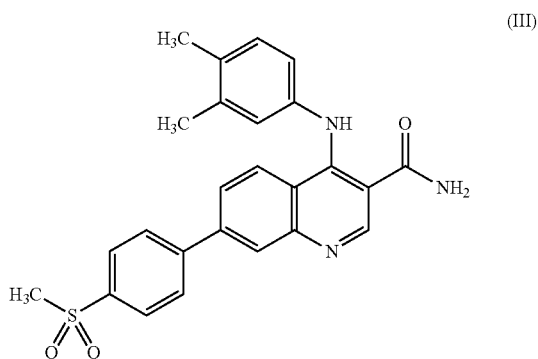 [SMILES: Cc1ccc(Nc2c(C(N)=O)cnc3cc(-c4ccc(S(C)(=O)=O)cc4)ccc23)cc1C]

or a salt thereof.

In another embodiment, the hydrophobic compound targeting CSF1R is 4-cyano-N-(5-(1-(2-(dimethylamino)acetyl)piperidin-4-yl)-2',3',4',5'-tetrahydro-[1,1'-biphenyl]-2-yl)-1H-imidazole-2-carboxamide (also referred to as JNJ-28312141) having the chemical formula:

(IV)

or a salt thereof.

In another embodiment, the hydrophobic compound targeting TNFα is N4-(4-phenoxyphenethyl)quinazoline-4,6-diamine (also referred to as QNZ) having the chemical formula:

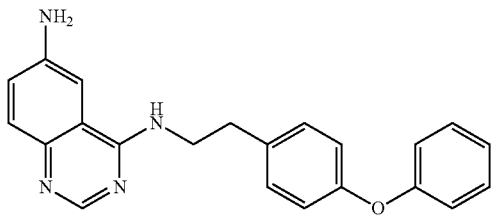

(V)

or a salt thereof.

In yet another embodiment, the hydrophobic compound targeting TNFα is 3-(4-Amino-1-oxoisoindolin-2-yl)piperidine-2,6-dione (also referred to as Lenalidomide or CC-5013) having the chemical formula:

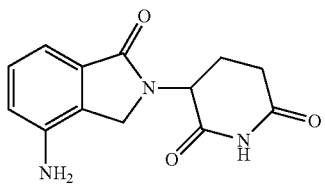

(VI)

or a salt thereof.

In one embodiment, the hydrophobic compound targeting TNFα is 6,7-dimethyl-3-[[methyl[2-[methyl[[1-[3-(trifluoromethyl)phenyl]-1H-indol-3-yl]methyl]amino]ethyl]amino]methyl]-4H-1-benzopyran-4-one (also referred to as SPD-304) having the chemical formula:

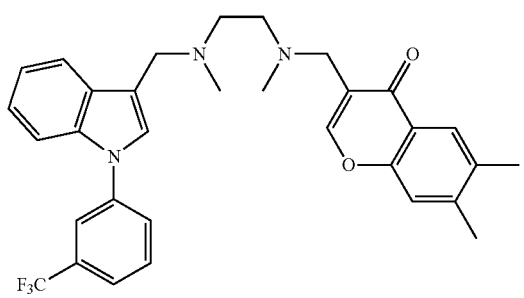

(VII)

or a salt thereof.

In one embodiment the hydrophobic compound targeting TGFβ is 4-(2-(6-methylpyridin-2-yl)-5,6-dihydro-4H-pyrrolo[1,2-b]pyrazol-3-yl)quinoline-6-carboxamide (also referred to as Ly215799) having the chemical formula:

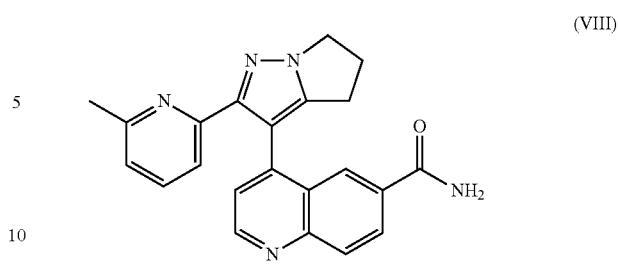

(VIII)

or a salt thereof.

In one embodiment the hydrophobic compound is (1E, 6E)-1,7-bis (4-hydroxy-3-methoxyphenyl)-1,6-heptadiene-3,5-dione (also referred to as Curcumin) having the chemical formula:

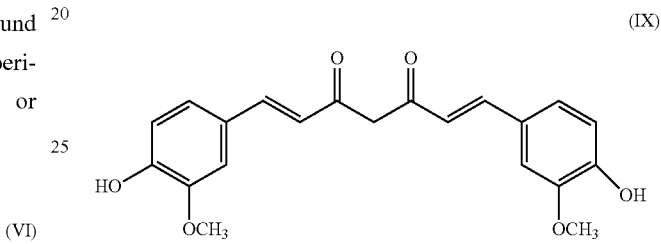

(IX)

or a salt thereof.

In a further embodiment the hydrophobic compound is (9-fluoro-11β,17,21-trihydroxy-16α-methylpregna-1,4-diene-3,20-dione (also referred to as Dexamethasone) having the chemical formula:

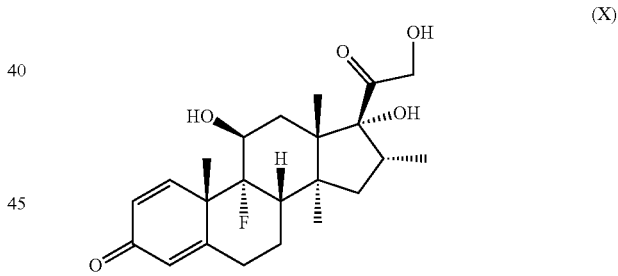

(X)

or a salt thereof.

Hydrophobic compounds of the present invention (e.g., compounds of formulae I-X) may be in free form or in the form of physiologically, non-toxic salts thereof. These salts may be obtained by reacting the respective compounds with physiologically acceptable acids and bases. Examples of such salts include but are not limited to hydrochloride, hydrobromide, hydroiodide, hydrofluoride. nitrate, sulfate, bisulfate, pyrosulfate, sulfite, bisulfate, phosphate, acid phosphate, monohydrogenphosphate, dihydrogenphosphate, metaphosphate, pyrophosphate, isonicotinate, acetate, trifluoroacetate, propionate, caprylate, isobutyrate, lactate, salicylate, citrate, tartrate, oxalate, malonate, suberate, sebacate, mandelate, chlorobenzoate, methylbenzoate, dinitrobenzoate, phthalate, phenylacetate, malate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminium, calcium, lithium, magnesium, potassium, sodium, zinc, and diethanolamine, N,N'-dibenzylethylenediamine, chloroprocaine, choline, dicyclohexylamine, ethylenediamine, N-methylglucamine, and procaine salts.

In some embodiments, the hydrophobic compound is poorly soluble in aqueous solutions. As used herein "poorly soluble" refers to low aqueous solubility of a compound such that one part of solute of the compound required greater than or equal to 30 parts of solvent to dissolve the solute. As used herein, the terms "poorly soluble in aqueous solutions" and "hydrophobic" are used interchangeably.

As is known in the art, hydrophobic compounds with the same chemical composition but different physical forms (e.g., crystalline v. non-crystalline/amorphous) can exhibit different properties, including rate of solubilization and chemical stability. Generally, crystalline forms of the hydrophobic compounds have improved chemical stability compared to amorphous or powder forms.

Accordingly, the present invention also encompasses compositions comprising a mixture of a uniform population of free single crystals of a hydrophobic compound and an amorphous form of the hydrophobic compound. The terms "amorphous" and "powder" or phrase "amorphous form" and the like, refer to any noncrystalline material in which the atoms and molecules are not organized in a uniform and repetitive pattern. One particular embodiment of the invention is provided in FIG. 4, where both amorphous and crystalline forms of the anti-inflammatory compound curcumin are provided in the same composition. As demonstrated in FIG. 5, the release profile of the crystalline form of curcumin is different than that of the corresponding amorphous form.

In general, a crystalline form is typically released more gradually than the amorphous form, and in a more linear manner. Such compositions with mixtures of amorphous forms and uniform populations of free, single crystals have applications in pharmaceutical formulations where controlled and/or extended release of the pharmaceutical agent is desired.

In certain embodiments, the invention provides a composition comprising a mixture of a uniform population of free single crystals of a hydrophobic compound and an amorphous form of the same hydrophobic compound. In one embodiment, the amount of hydrophobic compound in the crystalline form is higher than the amount of its amorphous form. For instance FIG. 5 describes a composition comprising a mixture of both crystalline and amorphous forms of curcumin such that the ratio between the two forms is 3:1 respectively. In certain embodiments, the invention provides a composition comprising a mixture of both crystalline and amorphous forms of curcumin such that the ratio between the two forms is 1:1 respectively. In another embodiment, the amount of hydrophobic compound in the crystalline form is lower than the amount of its amorphous form.

In a particular embodiment, the composition comprises a mixture of a uniform population of free single crystals and an amorphous form of a hydrophobic compound such that the amount of hydrophobic compound in the crystalline form is no greater than about 90% by weight (including about 10%, about 20%, about 30%, about 40%, about 50%, about 60%, about 70%, about 85%, about 90% by weight in crystalline form). Since physical and chemical stability of the hydrophobic compound generally tends to improve with increasing amounts of crystalline form of the compound, in some embodiments, the amount of crystalline form of the compound is at least about 90% by weight (including about 10%, about 20%, about 30%, about 40%, about 50%, about 60%, about 70%, about 85%, about 90%). The amount of hydrophobic compound that is crystalline in a particular composition may be determined by any conventional technique known in the art, for instance, by Powder X-Ray Diffraction (PXRD) and Single-crystal X-Ray Diffraction (SXRD).

In some embodiments, each free, single crystal in a uniform population is encapsulated. The term "encapsulate" is generally used to describe the enclosure of one material (e.g., compound, crystal) by a different material (e.g., an inert material). A material, as used herein, without being subject to limitation, can be an inert (e.g., non-reactive) or a reactive (e.g., chemical compound such as compounds with Formulae I-X). Non-limiting examples of materials used for encapsulation of crystals include ceramics, glass, metal, poly lactic-co-glycolic acid (PLGA) co-polymer, polymer (e.g., biocompatible polymer) and alginate hydrogels.

In one embodiment, the invention provides a composition comprising a uniform population of free, single crystals of a hydrophobic compound encapsulated in a polymer (e.g., biocompatible polymer). In a particular embodiment, the polymer is a biocompatible polymer (e.g., alginate hydrogel). In other embodiments, the uniform population of free, single crystals is encapsulated in a biocompatible polymer together with at least one additional biological material (e.g., live cells or tissues). A biological material, as used herein, without being subject to limitation, can be a population of cells, including a whole cell (e.g., islet cell) or a part of a cell (e.g., an organelle of a cell such as mitochondria) or combinations thereof. A biological material, as used herein, without being subject to limitation, can be a tissue, including a tissue obtained from the subject (e.g., pancreatic tissue) or an engineered tissue or combinations thereof.

A first polymorph embodiment of the present invention is a polymorph of a compound represented by chemical formula (I) or a salt thereof:

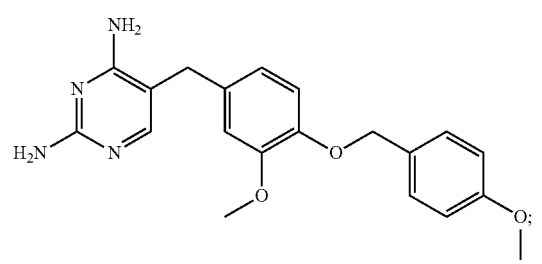

(I)

characterized by at least five major powder x-ray diffraction peaks at 2θ angles selected from 18.42°, 19.46°, 19.88°, 21.4°, 21.64°, 22.22°, 23.82°, 29.64° and 31.08°. In an aspect of this embodiment, the polymorph is characterized by at least eight powder x-ray diffraction peaks at 2θ angles selected from powder x-ray diffraction peaks at 2θ angles of 18.42°, 19.46°, 19.88°, 21.4°, 21.64°, 22.22°, 23.82°, 29.64°, 31.08°, 9.4°, 10.28°, 15.44°, 19.6°, 23.4°, 25.66°, and 28.52°. In a further aspect, the polymorph is characterized by at least twelve powder x-ray diffraction peaks at 2θ angles selected from powder x-ray diffraction peaks at 2θ angles of 18.42°, 19.46°, 19.88°, 21.4°, 21.64°, 22.22°, 23.82°, 29.64°, 31.08°, 9.4°, 10.28°, 15.44°, 19.6°, 23.4°, 25.66°, 28.52°, 11.68°, 17.24°, 18.12°, and 31.22°. In yet a further aspect, the polymorph is characterized by at least twenty powder x-ray diffraction peaks at 2θ angles selected from powder x-ray diffraction peaks at 2θ angles of 18.42°, 19.46°, 19.88°, 21.4°, 21.64°, 22.22°, 23.82°, 29.64°, 31.08°, 9.4°, 10.28°, 15.44°, 19.6°, 23.4°, 25.66°, 28.52°, 11.68°, 17.24°, 18.12°, 31.22°, 12.32°, 16.34°, 18.86°, 25.52°, 26°, 26.24°, 29.34°, 33.04°, and 34.04°. In yet a further aspect, the polymorph is characterized by powder x-ray diffraction peaks at 2θ angles selected from powder x-ray diffraction peaks at 2θ angles of 18.42°, 19.46°, 19.88°, 21.4°, 21.64°, 22.22°, 23.82°, 29.64°, 31.08°, 9.4°, 10.28°, 15.44°, 19.6°, 23.4°, 25.66°, and 28.52°. In yet a further aspect, the polymorph is characterized by x-ray diffraction peaks at 2θ angles selected from powder x-ray diffraction peaks at 2θ angles of 18.42°, 19.46°, 19.88°, 21.4°, 21.64°, 22.22°, 23.82°, 29.64°, 31.08°, 9.4°, 10.28°, 15.44°, 19.6°, 23.4°, 25.66°, 28.52°, 11.68°, 17.24°, 18.12°, and 31.22°. In yet a further aspect, the polymorph is characterized by powder x-ray diffraction peaks at 2θ angles selected from powder x-ray diffraction peaks at 2θ angles of 18.42°, 19.46°, 19.88°, 21.4°, 21.64°, 22.22°, 23.82°, 29.64°, 31.08°, 9.4°, 10.28°, 15.44°, 19.6°, 23.4°, 25.66°, 28.52°, 11.68°, 17.24°, 18.12°, 31.22°, 12.32°, 16.34°, 18.86°, 25.52°, 26°, 26.24°, 29.34°, 33.04°, and 34.04°.

In a second polymorph embodiment, the polymorph of the first polymorph embodiment or any aspect of the first embodiment, is characterized by a powder x-ray diffraction (PXRD) pattern substantially in accordance with FIG. 20 C.

In yet another embodiment, the polymorph of the first or second polymorph embodiment or any aspect of the first embodiment, is characterized by a unit cell with dimensions (a is 5.449 Å, b is 9.686 Å, c is 17.653 Å) and angles (alpha is 77.11°, beta is 87.58°, and gamma is 84.08°).

A third polymorph embodiment is a polymorph formed by any of the processes (e.g., method II) described herein.

In a specific aspect of the third polymorph embodiment, the polymorph is of a compound, represented by chemical formula (I):

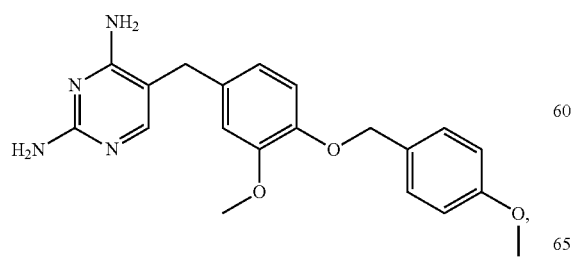

represented by chemical formula (II):

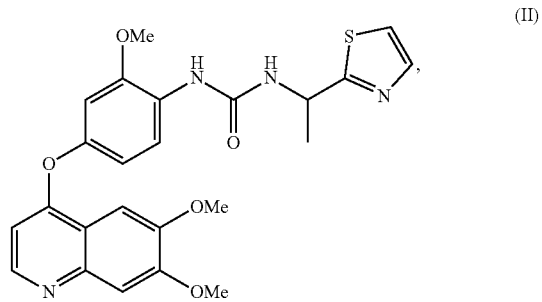 [SMILES: COc1cc(Oc2ccnc3cc(OC)c(OC)cc23)ccc1NC(=O)NC(C)c1nccs1]

represented by chemical formula (III):

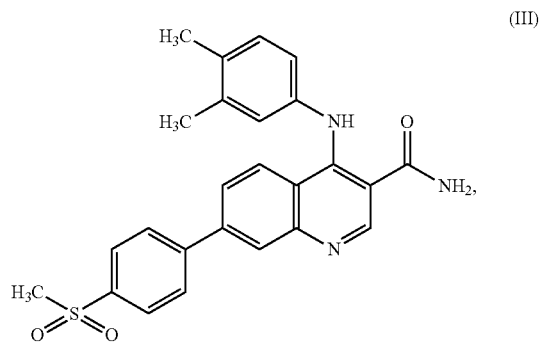 [SMILES: Cc1ccc(Nc2c(C(N)=O)cnc3cc(-c4ccc(S(C)(=O)=O)cc4)ccc23)cc1C]

represented by chemical formula (IV):

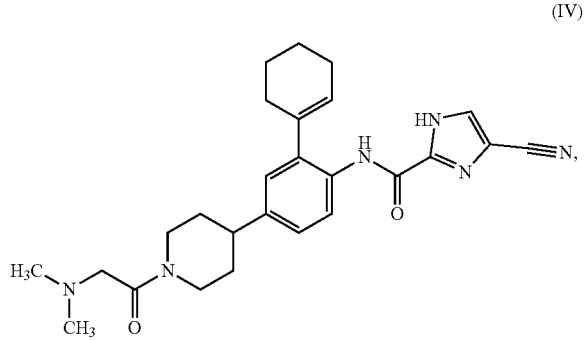 [SMILES: CN(C)CC(=O)N1CCC(c2ccc(NC(=O)c3nc(C#N)c[nH]3)c(C3=CCCCC3)c2)CC1]

represented by chemical formula (V):

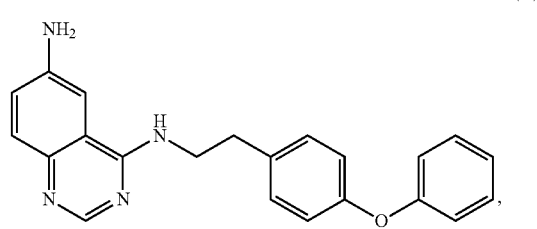

represented by chemical formula (VI):

(VI)
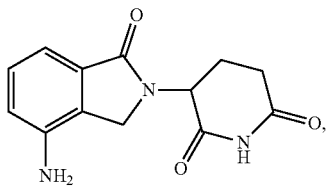

represented by chemical formula (VII):

(VII)
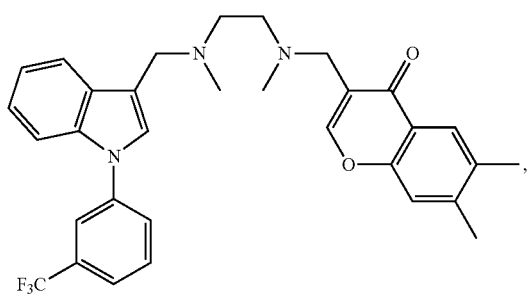

represented by chemical formula (VIII):

(VIII)
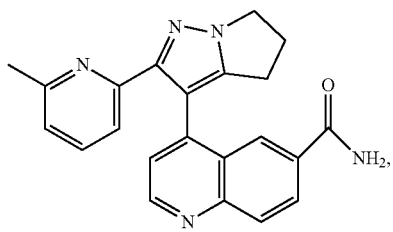

represented by chemical formula (IX): or (IX)
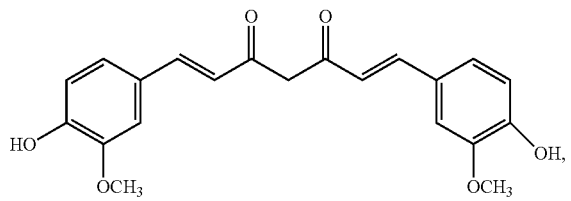

represented by chemical formula (X):

(X)
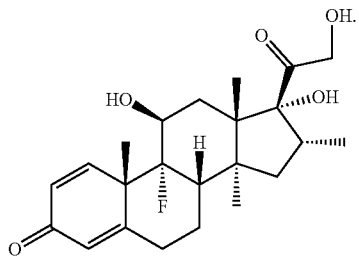

A further embodiment is a pharmaceutical composition comprising a polymorph of any of the above recited polymorph embodiments; and a pharmaceutically acceptable carrier or excipient.

Yet a further embodiment is a method of treating or preventing an inflammatory condition in a subject in need thereof, comprising administering to the subject an effective amount (e.g., a therapeutically effective amount) of a polymorph of any one of the above recited polymorph embodiments, or a pharmaceutical composition of the preceding embodiment. In a preferred aspect, the inflammatory condition is fibrosis.

It is well known and understood to those skilled in the art that the apparatus employed, humidity, temperature, orientation of the powder crystals, and other parameters involved in obtaining a powder X-ray diffraction (PXRD) pattern may cause some variability in the appearance, intensities, and positions of the lines in the diffraction pattern. A powder X-ray diffraction pattern that is "substantially in accordance" with a figure (showing an PXRD pattern) provided herein (FIG. 20C) is a PXRD pattern that would be considered by one skilled in the art to represent the same polymorph that provided the PXRD pattern of the figure provided herein. Thus, a PXRD pattern that is substantially in accordance may be identical to that provided herein, or more likely it may be somewhat different. Such a PXRD pattern may not necessarily show each of the lines of the diffraction patterns presented herein, and/or may show a slight change in appearance, intensity, or a shift in position of said lines resulting from differences in the conditions involved in obtaining the data. A person skilled in the art is capable of determining if a sample of a crystalline compound is the same polymorph, or a different polymorph, from the polymorph disclosed herein by comparison of their PXRD patterns. Similarly, a person skilled in the art is capable of determining if a given diffraction angle (expressed in ° 2θ) obtained from a PXRD pattern is at about the same position value presented herein. It is to be understood that any 2θ angle specified herein, with the exception of any 2θ angles given in the Example sections or in the Figures, means the specified value±0.2°. For example, if a described embodiment or claim specifies a 2θ angle of 21.64°, this is to be understood to mean 21.64°±0.2°, that is a 2θ angle from 21.44° to 21.84°.

As used herein, "major powder x-ray diffraction peak" refers to a peak in a powder x-ray diffraction pattern with a relative intensity greater than 40%. Relative intensity is calculated as the ratio of the peak intensity of the peak of interest versus the peak intensity of the largest peak within the 2-theta range shown in FIG. 20C (right panel).

As known in the art, a polymorph can be characterized by dimensions (a, b, and c) and angles (alpha, beta and gamma) of its unit cell, the smallest volume element that by repetition in three dimensions describes the polymorph crystal structure. It is to be understood that any unit cell angle specified herein, with the exception of any unit cell angles given in the Example sections or in the Figures, means the specified value±0.1°. Also, it is to be understood that any unit cell dimension specified herein, with the exception of any unit cell dimension given in the Example sections or in the Figures (e.g., FIG. 20A), means the specified value±0.01.

Compositions of the invention comprising a uniform population of free, single crystals of a hydrophobic compound can be used for various applications, for instance, as a pharmaceutical formulation for sustained-release of a therapeutic agent (see, e.g., the Examples and FIGS. 3-12 of this application). "Sustained-release" of a therapeutic agent means that the therapeutic agent is released from the composition at a controlled rate so that therapeutically beneficial blood levels or beneficial levels of the therapeutic agent at the site of administration (e.g., implantation site), are maintained over an extended period of time, e.g., 1 to 24 hours; 8 to 24 hours; 12 to 24 hours, 1-2 days, 2-4 days, 4-10 days, 10-100 days 100-300 days, 300-600 days and any intermediate period. The terms "sustained release" and "controlled release" are used interchangeably. Alternatively, the compositions of the present invention, can be used for various non-pharmaceutical sustained-release applications including, but not limited to, nutraceuticals, insecticides, herbicides, flavoring compounds, dyes, catalysts and others. As used herein "delayed release" of an agent (e.g., therapeutic agent) means that the agent is released from the composition only after an initial period of delay such that the levels of the therapeutic agent is almost undetectable when measured locally (e.g., at the point of administration, implantation site) or systemically (e.g., blood levels of the therapeutic agent) during the delay period. The delay period can range from few minutes, few hours to few (e.g., 1 to 60 minutes, 1 to 24 hours; 8 to 24 hours; 12 to 24 hours, 1-2 days, 2-4 days, 4-10 days, 10-100 days 100-300 days, 300-600 days and any intermediate period.)

In certain embodiments, the compositions of the invention described herein are formulated for therapeutic (e.g., pharmaceutical) use with one or more pharmaceutically-acceptable carriers or excipients. The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient. Generally, pharmaceutically-acceptable carriers or excipients may be present in amounts having no substantial effect on the stability and release rate profiles of the hydrophobic compound(s) in the composition. Suitable excipients/carriers are well known in the art, including those described in Gennaro et al., Remington's Pharmaceutical Sciences (18th ed., Mack Publishing Company, 1990, see especially Part 8: Pharmaceutical Preparations and their Manufacture), which is incorporated herein by reference in its entirety. The compositions of the invention formulated for therapeutic use may be used as is, or may be used as a pharmaceutically acceptable salt thereof. The term "pharmaceutically acceptable salt" means either an acid addition salt or a basic addition salt which is compatible with the treatment of patients/subjects.

In some embodiments, exemplary inorganic acids which form suitable salts include, but are not limited thereto, hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms. Other non-pharmaceutically acceptable salts e.g. oxalates may be used for example with compounds of Formulae I-X for laboratory use, or for subsequent conversion to a pharmaceutically acceptable acid addition salt.

The compositions of the invention can be in a solid form or liquid form. Typically, they are in dosage unit form, such as tablet, powder, sachet, bead, pellet, osmotic dosage form, etc., but they may as well be in a liquid, cream or aerosol form for use in various applications, i.e., parenteral, oral, buccal, ophthalmic, nasal, dermal, rectal, and pulmonary routes. In one embodiment, the compositions provided in the present invention are encapsulated. Non limiting examples of materials used for encapsulation of the composition of the current invention include materials composed of ceramic, glass, metal, poly lactic-co-glycolic acid (PLGA) co-polymer, polymer (e.g., polystyrene beads) and alginate hydrogels. In a particular embodiment, the compositions provided in the present invention are encapsulated in a biocompatible polymer (e.g., alginate hydrogel).

The compositions of the present invention can be formulated for different modes of administration, including, but not limited to, parenteral, oral, buccal, ophthalmic, nasal, dermal, rectal, and pulmonary routes. In one embodiment, the compositions are in an oral delivery form, such as a tablet, capsule or osmotic dosage form. In another embodiment, the compositions are in a form suitable for administration by injection. In another embodiment, the compositions are in a form suitable for administration by implantation.

Methods of Administration

The present invention also provides, in various embodiments, methods for delivering to a subject (e.g., a subject in need thereof) a uniform population of free single crystals of a hydrophobic compound. The method comprises administering to the subject a composition of the invention described herein. In a particular embodiment, the composition comprises an effective amount of a uniform population of free single crystals of a hydrophobic compound, wherein each free, single crystal in the population has a characteristic dimension of greater than about 1 micrometer.

The composition can be administered to the subject as a prophylactic or therapeutic composition (e.g., to prevent or treat a disease or condition) or, alternatively, as a non-therapeutic composition (e.g., a nutraceutical or cosmetic composition).

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical, medical, electrical, electrochemical, mechanical and electromechanical arts.

As used herein, "subject" refers to a mammal (e.g., human, non-human primate, cow, sheep, goat, horse, dog, cat, rabbits, guinea pig, rat, mouse). As used herein, "non-human animal" refers to a mammal that is not human (e.g., non-human primate, cow, sheep, goat, horse, dog, cat, rabbits, guinea pig, rat, mouse). As used herein, the "subject" can also refer to tissue (e.g., tissue obtained from a human, a non-human primate, a cow, a sheep, a goat, a horse, a dog, a cat, a rabbits, a guinea pig, a rat, a mouse or an engineered tissue prepared in a laboratory). Non-limiting examples of engineered tissue include iPS (induced pluripotent stem cells that differentiate into therapeutic cells types (e.g., islets), 3D printed tissues from primary cells or cell lines, genetically engineered cells/tissues to deliver factors or influence microenvironment, organoids grown in suspension from primary tissues, and cells/tissues integrated with synthetic components (e.g., nanowires). In a particular embodiment, the subject is a human. A "subject in need thereof" refers to a subject (e.g., patient) who has, or is at risk for developing, a disease or condition that can be treated (e.g., improved, ameliorated, prevented) by the hydrophobic compound to be administered.

As used herein, the terms "treat," "treating," or "treatment," mean to counteract a medical condition (e.g., localized inflammation) to the extent that the medical condition is improved according to a clinically-acceptable standard (e.g., reduction or elimination of the localized inflammation).

In certain embodiments, an effective amount of a uniform population of free single crystals of a hydrophobic compound is administered to a subject in need thereof. As defined herein, an "effective amount" refers to an amount of hydrophobic compound (e.g., administered as a uniform population of free single crystals of the hydrophobic compound) that, when administered to a subject, is sufficient to achieve a desired therapeutic effect in the subject under the conditions of administration, such as an amount sufficient to inhibit (e.g., prevent, reduce, eliminate) an immune response (e.g., an inflammatory response) in the subject. As defined herein, an "therapeutically effective amount" refers to the lowest amount of the hydrophobic compound described herein (e.g., administered as a uniform population of free single crystals of the hydrophobic compound) that, when administered to a subject, is sufficient to achieve a desired therapeutic effect in the subject under the conditions of administration, such as an amount sufficient to inhibit (e.g., prevent, reduce, eliminate) an immune response (e.g., an inflammatory response such as fibrosis) in the subject.

In a particular embodiment, the invention provides a method for delivering to the subject compositions comprising a uniform population of free single crystals of hydrophobic compounds by administering to the subject a composition comprising uniform population of free single crystals of hydrophobic compounds that are biologically or pharmaceutically active along with a stabilizer. Such compositions comprise a high percentage of the biologically active hydrophobic compound by weight and decreased amounts of the stabilizer, thereby reducing any toxicities associated with the use of the stabilizers and thus enhancing the therapeutic efficacy of the hydrophobic compound. Suitable stabilizers include, but are not limited to, surfactants, which are molecules that can reduce the surface tension of a liquid. Surfactants can be cationic, anionic, non-ionic, and zwitterionic.

In one embodiment, the invention provides a method for delivering to a subject in need thereof, a composition comprising administering an effective amount of a uniform population of free single crystals of hydrophobic compounds, wherein the subject in need thereof is a human who has or is at a risk of developing an inflammatory condition. In a particular embodiment, the inflammatory condition is fibrosis. Suitable hydrophobic compounds for administration to a subject having fibrosis include, for example, hydrophobic compounds targeting CSF1R, such as GW2580, Ki20227, JNJ-28312141 and cFMS receptor inhibitor III.

In particular embodiments, the compositions comprising a uniform population of free single crystals of a hydrophobic compound are administered by injection. In another embodiment, the compositions comprising a uniform population of free single crystals of a hydrophobic compound are administered by implantation. For example, compositions described herein can be injected, surface deposited, and/or released from a drug depot that is inside an implanted biomaterial or medical device.

Other possible routes of administering a composition of the present invention, include, but are not limited to parenteral, oral, buccal, ophthalmic, nasal, dermal, rectal, pulmonary routes and/or local delivery to an affected tissue. A person skilled in the art will recognize that any one of the described routes of administration is contemplated by the method of delivering to a subject disclosed in the present invention.

In one embodiment, the method comprises of delivering a hydrophobic compound in combination with an immunosuppressant to a subject, wherein the immunosuppressant is provided in an amount effective to 1) allow for reduction of the necessary dose of hydrophobic compound that has to be delivered while maintaining the same immune suppression, and 2) further increase the specificity of the hydrophobic compound's action, by delivering and releasing the compound at the interface between the implanted material/device and the host immune response, eliminating the need for systemic (global) circulation, and 3) significantly extend release rate of the hydrophobic compound, thereby avoiding repeat injection schemes, for which compliance is difficult to maintain.

The present invention also provides a method for sustaining (e.g., controlling, extending, limiting) the release of a hydrophobic compound in a subject (e.g., a subject in need thereof). The method comprises administering to the subject a composition of the invention described herein. In a particular embodiment, the composition comprises an effective amount of a uniform population of free single crystals of a hydrophobic compound, wherein each free, single crystal in the population has a characteristic dimension of greater than about 1 micrometer.

As is known in the art, a hydrophobic compound in crystalline form is generally more stable than the compound in its amorphous form.

It is known in the art that dissolution rate of a crystal, a parameter indicating the stability of a crystal in a particular environment, is limited to the surface area of the crystal. Therefore, it is also possible to control the release kinetics of the material by manipulating crystal composition, crystalline degree, crystal size and morphology (e.g., polymorphism), etc.

Therefore, crystalline forms of the hydrophobic compound are particularly useful for slow, controlled, extended and/or long-term sustained release of a hydrophobic compound, while amorphous materials are useful for fast/burst release of a hydrophobic compound. Thus, without wishing to be bound by theory, it is believed that, by controlling the amount of the material in crystalline and amorphous form of the hydrophobic compound in a composition, it is possible to control the release kinetics of the compound administered to a subject.

Thus, in one embodiment, the invention provides a method for sustaining (e.g., controlling, extending, limiting) the release of a hydrophobic compound by administering to a subject in need thereof a composition comprising at least two different uniform populations of free single crystals of a single hydrophobic compound, each having crystals of different characteristic sizes. For instance, FIG. 4 shows representative microscopic images of a composition comprising at least two different uniform populations of free single crystals of the hydrophobic compound with anti-inflammatory property, curcumin, where the population of smaller crystals release curcumin in the crystal at faster rate than the population of larger crystals. In another embodiment of the method, the composition that is administered to the subject in need thereof comprises at least one uniform population of free single crystals of at least two different hydrophobic compounds. In other embodiments of the invention, the method for extending the release of hydrophobic compounds by administering to a subject in need thereof can comprise a composition that is a mixture of at least two uniform populations of free single crystals of at least two different hydrophobic compounds, each having crystals of different characteristic sizes such that the population of smaller crystals release the hydrophobic compound in the crystal at faster rate than the population of larger crystals. In certain embodiments of the invention, the method for extending the release of a hydrophobic compound by administering to a subject in need thereof can comprise a composition that is a mixture of a uniform population of free single crystals and an amorphous form of a hydrophobic compound, as shown in FIG. 4.

In some embodiments, less than about 5%-30% (including, e.g., about 5%, about 10%, about 15%, about 20%, about 25%, about 30% of the hydrophobic compound is released in the subject after 2 days under physiological conditions and/or less than about 40-90% (e.g., about 40%, about 50%, about 60%, about 70%, about 80% or about 90%) of the hydrophobic compound is released after 60 days under physiological conditions. In some embodiments, less than about 80% of the hydrophobic compound is released after about 180 days under physiological conditions. In some embodiments, less than about 90% of the hydrophobic compound is released after about 240 days under physiological conditions. In further embodiments, less than about 10% of hydrophobic compound is released after 2 days under physiological conditions and/or less than about 90% of the hydrophobic compound is released after 60 days under physiological conditions.

Formulation Processes

In various embodiments, the present invention also provides a process for preparing a uniform population of free, single crystals of a hydrophobic compound. In general, the process comprises the steps of (a) providing a solution consisting essentially of the hydrophobic compound in a solvent, (b) forming a mixture by adding to the solution an anti-solvent in an amount sufficient to induce formation of the free, single crystals and not exceeding the amount of anti-solvent that causes the compound to precipitate from the solvent, and (c) harvesting the free, single crystals. In one embodiment, the mixture in (b) is incubated for a period of time ranging from about 1 hour to about 6 hours prior to harvesting in (c). In a different embodiment, the mixture in (b) is incubated for a period of time less than about 6 hours prior to harvesting in (c). In a further embodiment, the mixture in (b) is incubated for a period of time less than about 4 hours prior to harvesting in (c). In some embodiments step (b) is carried out at a temperature ranging from about 0° C. to about 60° C. In a particular embodiment, step (b) is carried out at a constant temperature of about 25° C.

The term "solution" refers to a substantially homogeneous mixture of a solute (e.g., solid) in a solvent (e.g., a liquid). In one embodiment, the solution in (a) is a solution wherein the hydrophobic compound is dissolved in a solvent. As used herein, the term "dissolve" refers to the solubilization of a solid into a solvent as it passes into solution.

The term "solvent", as used herein, refers to a liquid in which a particular hydrophobic compound is soluble. Solvents include, but are not limited to, organic solvents. Non-limiting examples of a solvent include Dimethyl sulfoxide (DMSO), acetone, ether, n-Hexane, butanone, anisole, chloroform, dichloromethane, methyl acetate, ethyl acetate, acetyl acetate, Tetrahydrofuran (THF), methanol, ethanol, ethanol+THF, isopropanol. In some embodiments, the organic solvent is one that is volatile. As used herein, the term "volatile" refers to a property of a solvent that can be readily evaporated at ambient temperature and pressure.

An "anti-solvent", as used herein, refers to a liquid in which the hydrophobic compound is insoluble or substantially insoluble such that one part of solute of the hydrophobic compound required greater than or equal to 30 parts of anti-solvent to dissolve the solute. Anti-solvents include, but are not limited to, organic solvents. Non-limiting examples of an anti-solvent include water, anisole, chloroform, dichloromethane, acetonitrile, methanol, isopropanol, acetone, ether, methyl acetate, ethyl acetate, acetyl acetate, Xylene, Hexane, Heptane, Heptane+water. In some embodiments, the organic solvent is one that is volatile. The solvent and anti-solvent used in the process can be selected by a skilled person based on characteristics of the hydrophobic compound being crystallized. Typically, the solvent and anti-solvent are readily miscible in the proportions employed. Suitable combinations of solvent:anti-solvent include but are not limited to, DMSO:Water, Acetone:Water, Acetone:Heptane, Butanone:Heptane, Butanone:Water, Ethyl acetate:Hexane, Ethanol:Ethyl acetate, Butanone:Heptane+Water, Ethanol+THF:Water, Ethanol: Xylene, Ethanol: Acetonitrile, anisole/hexane, Ethyl acetate:Heptane, Ethanol:Water, Methyl acetate:Hexane, Methanol:Water and reciprocal pairs.

The term "harvesting", as used herein, refers to a process of collecting crystals. Methods of collecting crystals are well known and include without limitations, for example, manual harvesting from the crystal growth plates, automated harvesting using a laser based device.

In another embodiment, the invention provides a process for preparing a pharmaceutical composition or medical device comprising a uniform population of free, single crystals of a hydrophobic compound, which process comprises (a) providing a solution consisting essentially of the hydrophobic compound in a solvent, (b) forming a mixture by adding to the solution an anti-solvent in an amount sufficient to induce formation of the free, single crystals and not exceeding the amount of anti-solvent that causes the compound to precipitate from the solvent, (c) harvesting the free, single crystals, and (d) formulating the free, single crystals into a pharmaceutical composition or medical device comprising a uniform population of a free, single crystals of the hydrophobic agent. In some embodiments, step (d) includes mixing the population with other substances. Examples of other substances include a hydrophobic compound, a polymer, a metal, a pharmaceutically acceptable carrier or excipient.

In another embodiment, the invention provides a composition comprising a uniform population of free, single crystals of a hydrophobic compound, produced according to a process described herein. In one embodiment, the process comprises the steps of: (a) providing a solution consisting essentially of the hydrophobic compound in a solvent, (b) adding to the saturated solution an anti-solvent in an amount sufficient to induce formation of the free, single crystals and not exceeding the amount of anti-solvent that causes the compound to precipitate from the solvent; and (c) harvesting the free, single crystals. The term "saturated solution", as used herein refers to a solution in which no more of the solute (e.g., hydrophobic compounds of Formulae I-X) can be dissolved in a solvent. It is understood that saturation of the solution has been achieved when any additional solute that is added results in a solid precipitate or is let off as a gas. The terms "unsaturated solution" or "undersaturated solution", as used herein refers to a solution in which the solute (e.g., hydrophobic compounds of Formulae I-X) completely dissolves in the solvent such that additional solute can still be dissolved leaving no remaining substances. The term "super saturated solution", as used herein refers to a solution which contains more of the solute (e.g., hydrophobic compounds of Formulae I-X) than a saturated solution because of its tendency to crystallize and precipitate.

Read more at http://examples.yourdictionary.com/examples-of-saturated-solution.html#VRU1DV8vgfuYyRIb.99 mean "including but not limited to".

The terms "comprises", "comprising", "includes", "including", "having" and their conjugates mean "including but not limited to". The term "consisting of" means "including and limited to". The term "consisting essentially of" means that the composition, method or process may include additional ingredients, steps and/or features, but only if the additional ingredients, steps and/or features do not materially alter the basic and novel characteristics of the claimed composition, method or process.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an absolute limitation on the scope of the invention. Accordingly, the description of a range should be considered to have specifically disclosed all the possible subranges as well as individual numerical values within that range. For example, description of a range such as from 1 to 4 should be considered to have specifically disclosed subranges such as from 1 to 2, from 1 to 3, from 1 to 4, from 2 to 3, from 2 to 4, from 3 to 4 etc., as well as individual numbers within that range, for example, 1, 2, 3, and 4. This applies regardless of the breadth of the range. As used herein, the term "about" refers to ±10%. Whenever a numerical range is indicated herein, it is meant to include any cited numeral (fractional or integral) within the indicated range.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

EXEMPLIFICATION

Amorphous and crystalline forms of a wide range of hydrophobic drugs were screened for potential efficacy in the prevention and treatment of inflammation, fibrosis and host rejection of transplanted materials. It was hypothesized that the localized, controlled release of drugs utilizing drug crystals having a lower dissolution rate than amorphous drug would be able to better prevent and/or treat inflammation, fibrosis and host rejection of transplanted materials. A formulation that can release the drug in a gradual manner and ensure long term anti-fibrotic effects for months was envisioned.

Figure 2:
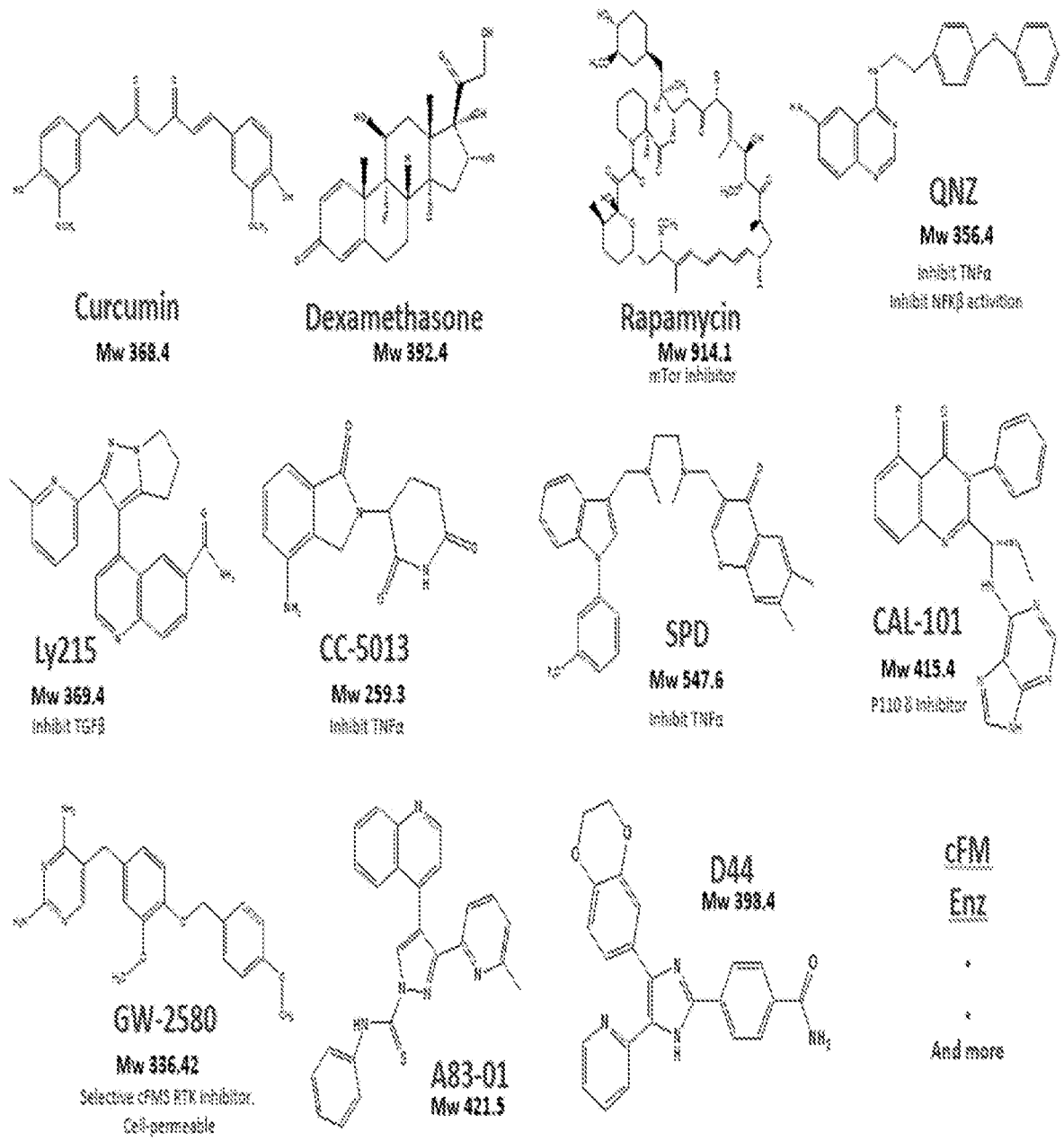
FIG. 2. Chemical structures of numerous screened hydrophobic drug candidates. These include classical broad-spectrum anti-inflammatory agents (e.g., dexamethasone, rapamycin, and curcumin), as well as macrophage-targeted agents (e.g., QNZ, a TNFalpha inhibitor; Ly215799, a TGFbeta inhibitor; and GW2580 (GW), a CSF1R inhibitor).

Specifically, a set of small molecules was screened to test the usefulness of novel amorphous and/or crystalline drug formulations for the prevention and/or treatment of inflammation, fibrosis and host rejection of transplanted materials. An agent screen was utilized that included specific immunomodulatory/inhibitory agents targeted to essential macrophage biology pathways. However, instead of selecting agents that completely remove an entire population of immune cells (i.e., macrophages), which has a number of potential negative side effects, several selective and targeted agents capable of macrophage inhibition and/or modulation were identified (see FIG. 2). Broad-spectrum anti-inflammatory agents dexamethasone, rapamycin, and curcumin were also tested (FIG. 2).

Figure 3:
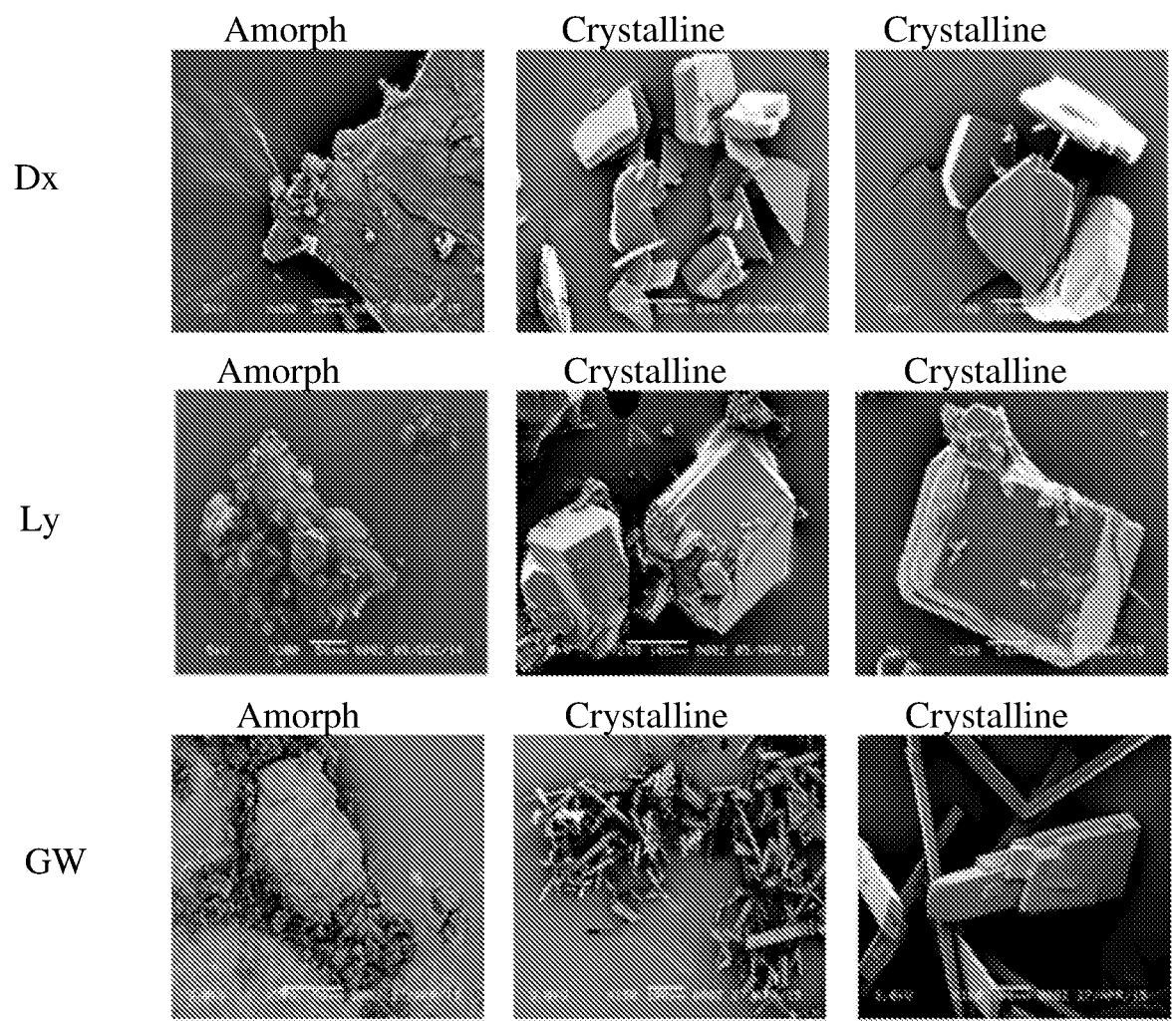
FIG. 3. Representative scanning electron microscopy (SEM) images of one classical broad-spectrum anti-inflammatory agent dexamethasone (Dx), as well as two targeted agents (Ly215799, Ly, a TGFbeta inhibitor; and GW2580, a CSF1R inhibitor) prepared as fine amorphous (left column), small crystals (middle column), or large crystals (right column). Depending on the drug and formulation, crystals ranged in size from 1 μm to 3 mm (also shown in FIG. 25).

Results:
Preparation and Comparison of Amorphous and Crystalline Hydrophobic Drug Formulations FIG. 3 shows representative scanning electron micrograph (SEM) images of dexamethasone (Dx), Ly215 (Ly), or GW2580 (GW) (also shown in FIG. 20B) crystals prepared according to the process of the invention described herein in comparison to amorphous powder formulations of each drug. Crystals of different sizes were designed and achieved (see FIG. 3, FIG. 20B).

Figure 5:
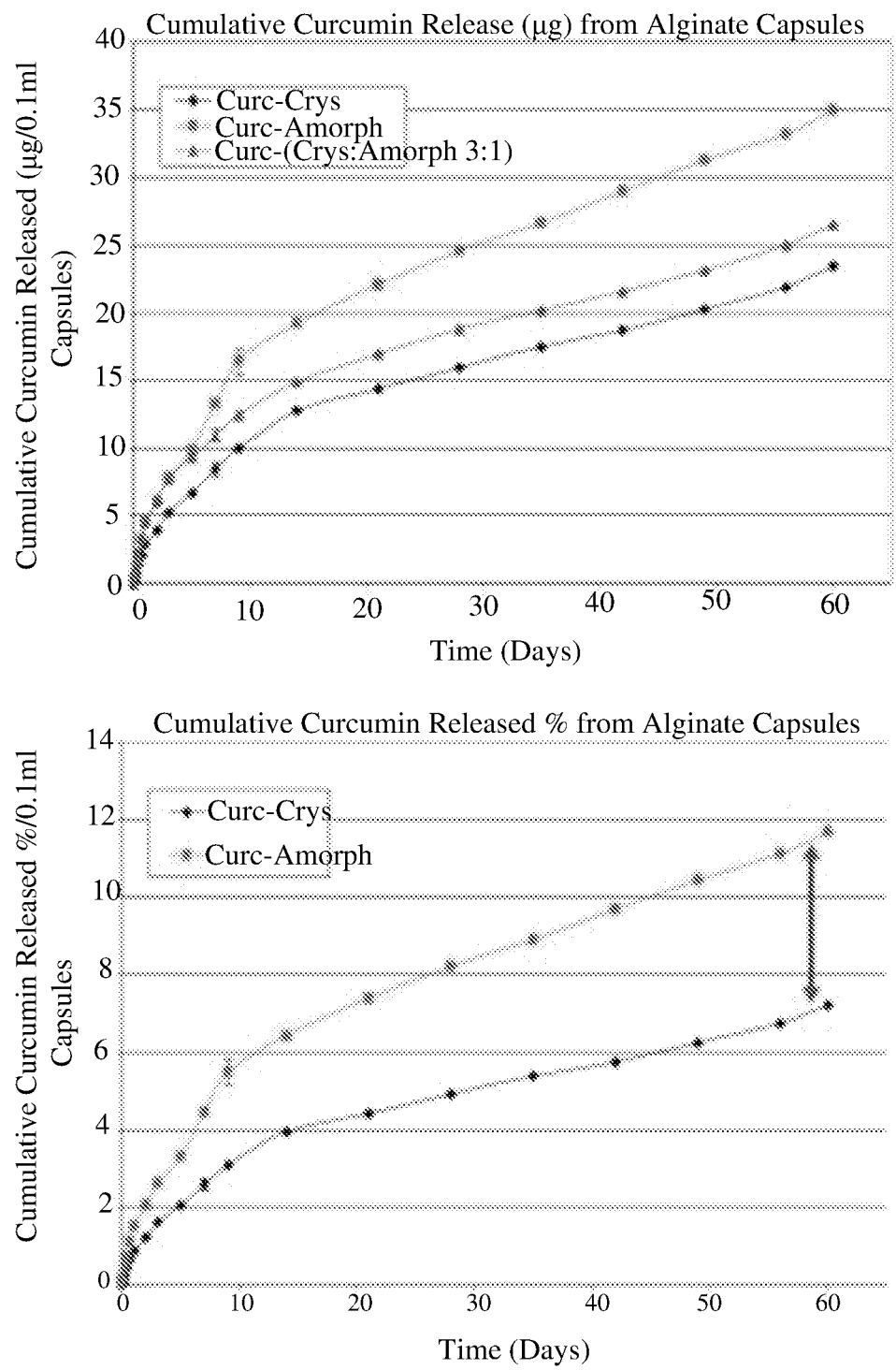
FIG. 5. Example of tunable rate of release for curcumin, encapsulated within alginate hydrogel capsules. Higher release is achieved with amorphous (squares) while pure crystalline curcumin (diamonds) releases more slowly initially, but can be maintained for much longer periods of time. The difference between the two profiles has been found to be variable depending on several parameters among them crystals size and crystallinity degree. A mixed-ratio (triangles) of both crystalline and amorphous formulations (in this case, at 3:1 respectively) has shown higher cumulative release amount of drugs followed by extended release. Mass balance analysis has confirmed the results.

Both crystalline and amorphous formulations of curcumin were encapsulated in alginate either separately or as a mixture of the two forms at different ratios (FIG. 4). These formulations have been traced in vitro for cumulative release for up to 2 months. FIG. 5 shows comparative release profiles for curcumin in crystalline and amorphous forms, as well as a mixture in a 3:1 ratio, respectively. It was found that a quicker drug release was achieved with amorphous curcumin, while crystalline curcumin releases more slowly initially, but can be maintained for much longer periods of time. The difference between the two profiles has been found to be variable depending on several parameters, among them crystal size and the degree of crystallinity. A mixed-ratio of both crystalline and amorphous formulations (in this case, at 3:1, respectively) exhibited both quick and extended release of curcumin. Both encapsulated formulations were followed microscopically and crystalline materials were found to exhibit surface release layer by layer which likely contributes to its long release profile (FIG. 5). Also it was found that drug release is dependent on crystal size, and smaller crystals release the drug faster than larger crystals due to surface area differences per crystal volume (FIG. 6).

Efficacy of Amorphous Hydrophobic Drug Formulations in the Prevention of Fibrosis For screening of anti-fibrotic drug activity, amorphous drug formulations were encapsulated inside 500 μm alginate capsules. Broad-spectrum anti-inflammatory agents curcumin, dexamethasone, and rapamycin have been used for preventing fibrosis of various biomaterials, such as polymer PLGA and hydrogel alginate. A panel of lead drug candidates (e.g., compounds of Formulae I-X) including the traditional broad-spectrum anti-inflammatories as well as agents targeted to essential macrophage biology pathways (e.g., TNFα, NFκB, p110δ/PI3K, TGFβ, and CSF1R) were selected. Ba+-cross-linked SLG20 alginate hydrogel spheres with these lead drug candidates were prepared as amorphous formulations to investigate the effect of macrophage immunomodulation on foreign body response. Drugs were encapsulated in amorphous form prepared by first dissolving in an organic solvent (e.g., vehicle in FIGS. 7, 9) then by mixing with alginate aqueous solution. Efficacy in preventing fibrosis was assessed in C57BL/6 mice at 2-weeks post implantation into the intraperitoneal (IP) cavity. Drug-containing spheres (500 µl/animal) were then implanted into the intraperitoneal space of C57BL/6 mice for 14 days. After this period, spheres were harvested and studied for cellular deposition and fibrosis. Based on earlier data, 2 weeks was found to be a sufficient time for fibrous capsule formation, and was sufficient for the vast majority of the drug to release from its amorphous formulations into the capsules.

Figure 7:
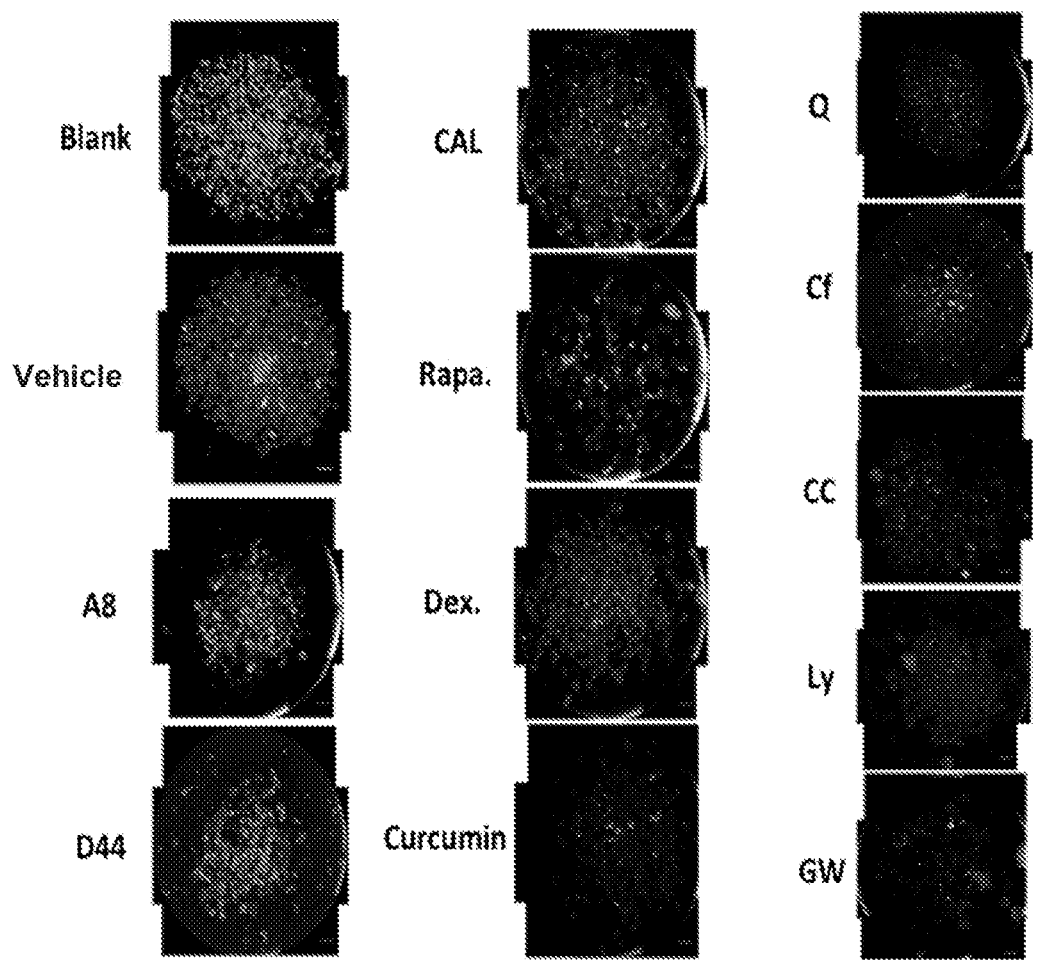
FIG. 7. Phase contrast images showing host foreign body responses (immune cell adhesion and fibrosis), observed as white plaque on the otherwise translucent alginate microspheres. Importantly, a number of these anti-inflammatory agents and more targeted small molecule inhibitors showed improved efficacy to prevent fibrosis after a 2-week implantation into the intraperitoneal (IP) space of C57BL/6 mice.
Figure 8:
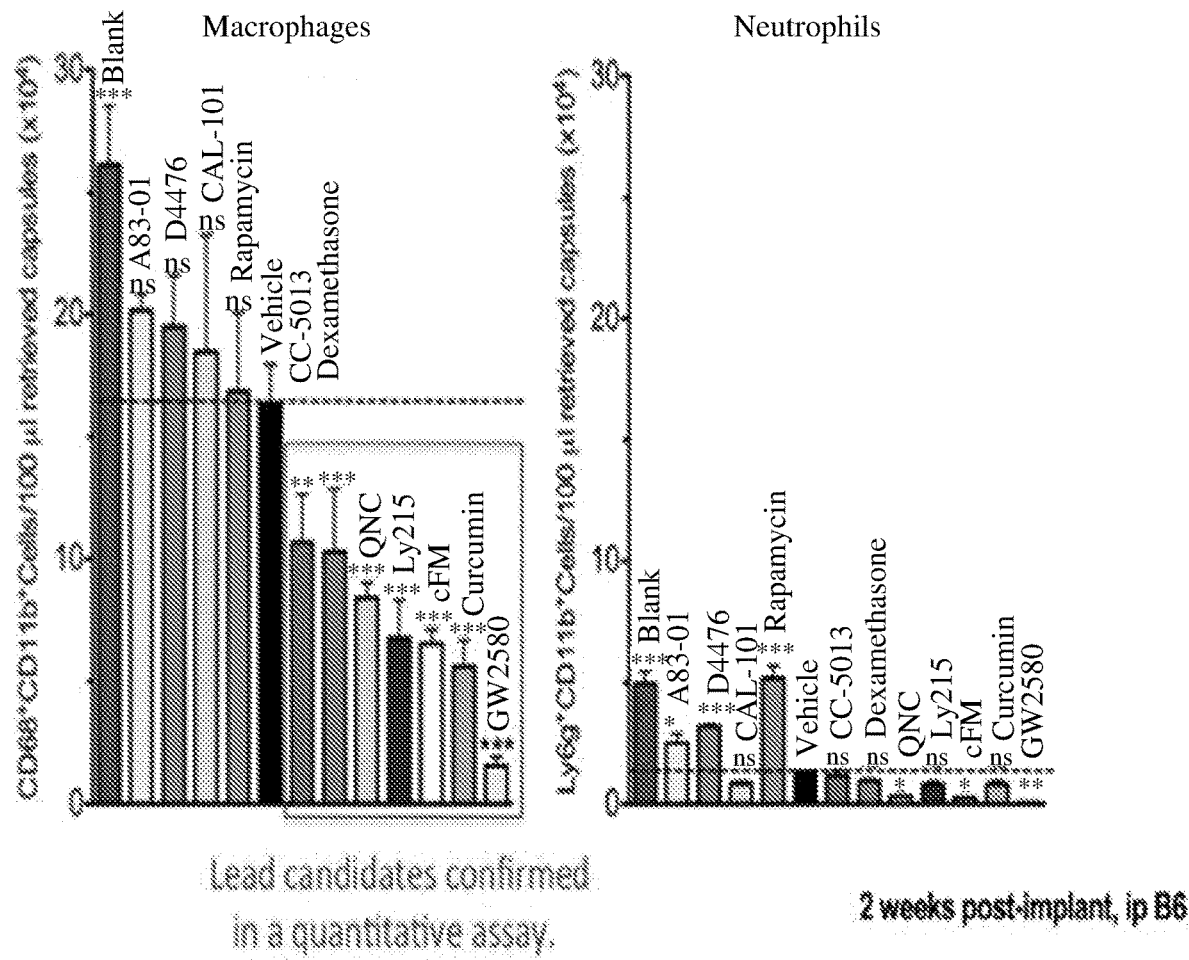
FIG. 8. Quantitative FACS analysis performed on cells dissociated directly off of alginate spheres, retrieved after the same 2-week implantation study reported in FIG. 7. Corroborating reduced plaque adhesion and fibrosis, the same lead candidates, encapsulated as amorphous formulations, are shown to reduce macrophage presence (left), and in most cases, also that of neutrophils (right). Data: mean±SEM, n=5. Statistical analysis: one-way ANOVA with Bonferroni multiple comparison correction *: $p<0.05$; : $p<0.001$, and *: $p<0.0001$; ns=not significantly different. Experiments repeated at least 2 times.
Figure 9:
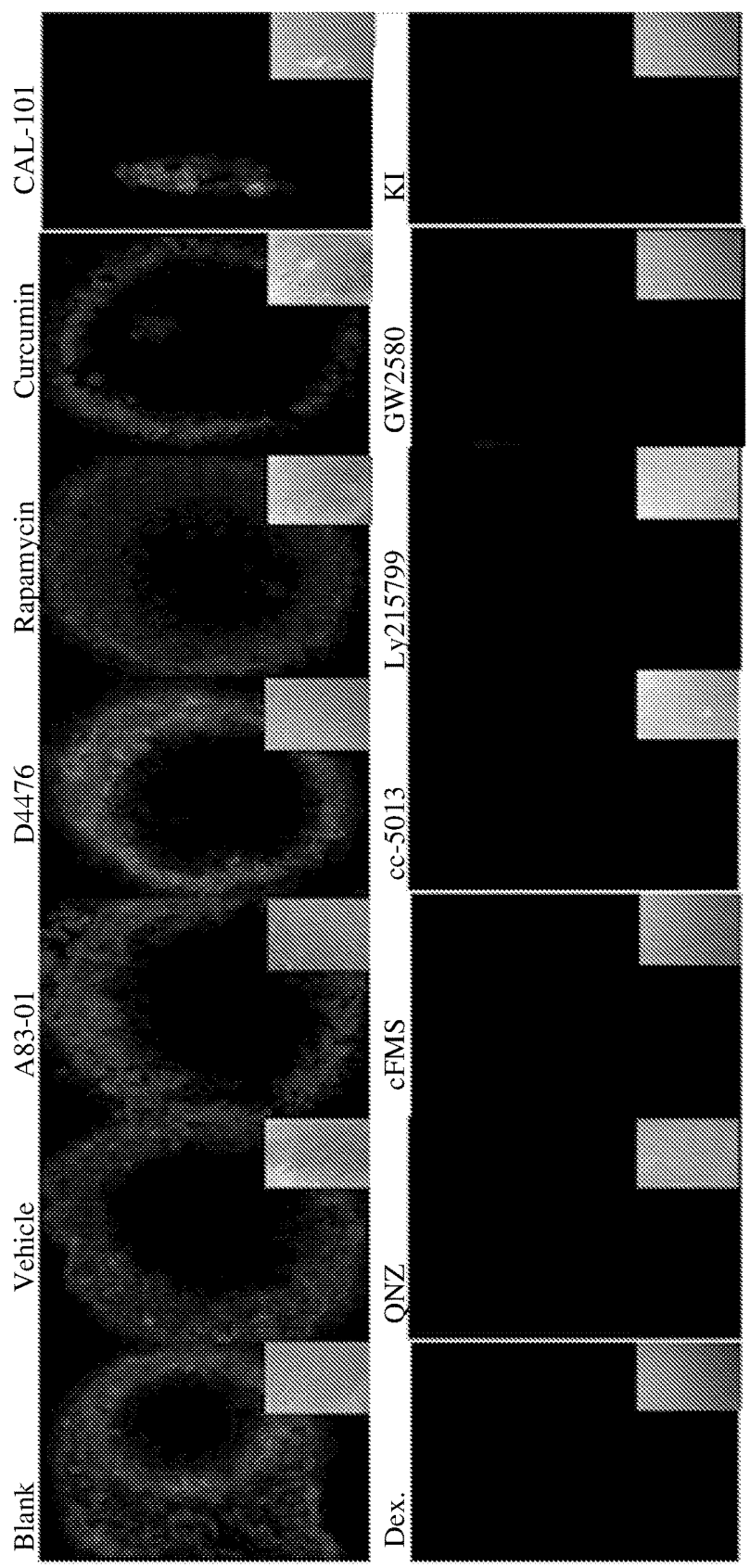
FIG. 9. Confocal microscopy images showing reduced or no fibrotic overgrowth on alginate microcapsules loaded with amorphous drug and retrieved after 2 weeks in the IP space of C57BL/6 mice. The alginate microcapsules were stained with a blue DAPI nuclear stain, a green dye marker for Macrophage CD68 and a red fibrosis marker for alpha smooth muscle actin. Insets represent brightfield images with the same fields of view as shown in the main confocal panel.

Post implantation, capsules were retrieved and analyzed by dark field phase contrast and confocal microscopy as well as quantitative FACS analysis (FIGS. 7-9). Phase contrast images for the control samples (Blank and vehicle) showed host foreign body response (immune cell adhesion and fibrosis), observed as white plaque on the otherwise translucent alginate microspheres, while the drug-loaded capsules showed less fibrosis formation (FIG. 7). Lead candidates were identified as those with almost no fibrosis at all (FIG. 7). Cellular deposition on spheres was examined using confocal imaging using DAPI (nucleus marker), F-actin (cellular cytoskeleton marker) or macrophage marker CD68, and alpha-smooth muscle actin ($\alpha$-SMA, myofibroblast marker) (FIG. 9). For the lead candidates, confocal microscopy images showed reduced or no fibrotic overgrowth on alginate microcapsules loaded with amorphous drug, and retrieved after 2 weeks in the IP space of C57BL/6 mice (FIG. 9).

Figure 10:
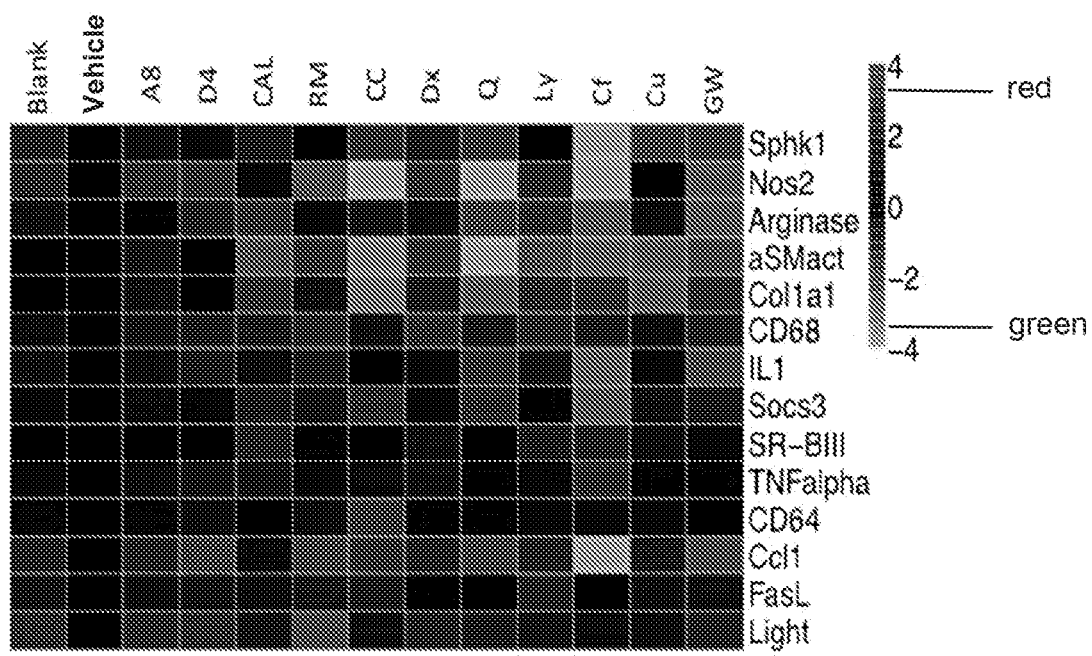
FIG. 10. Multiplexed NanoString gene expression analysis of Blank (no drug), drug vehicle (for amorphous formulations), and amorphous drug loaded microsphere capsules, following 2 week implantation in C57BL/6 mice.

These observed data were found to correlate with quantitative FACS analysis performed on cells dissociated directly off of alginate spheres and retrieved after the same 2-week implantation study. In addition to reduced plaque adhesion and fibrosis, the same lead candidates, encapsulated as amorphous formulations, were shown to reduce macrophage presence (FIG. 8, left graph), and in most cases, also that of neutrophils (FIG. 8, right graph). These capsules included Blank and vehicle controls (no drug) and amorphous drug-loaded microsphere capsules. Drug extraction from retrieved capsules indicated less than 5% of loaded drug was found attributing the observed activity to the payload release. Capsules were analyzed for gene expression responses to profile host-mediated innate immune recognition following a 2-week implantation in C57BL/6 mice using Nanostring multiplexed gene expression analysis (FIG. 10). Fibrosis-associated macrophage phenotypes and corresponding fibrotic response correlated as numerous drugs inhibited host response to varying degrees (FIG. 10, green represented as the lighter shade in the gray scale drawing), as compared to levels induced by no drug (blank) and vehicle-loaded controls. Inhibitors with similar targets induced similar phenotypes (e.g., A8 and D4; CAL, CC, and QNZ), and most showed significant inhibition of inflammatory macrophage markers Sphingosine Kinase 1 (Sphk1), Tumor Necrosis Factor $\alpha$ (TNF$\alpha$), Arginase 1 (Arg1), and Interleukin 1 (IL1). Interestingly, both cFM and GW (GW2580) targeting CSF1R also exhibited almost identical gene expression responses. Activated myofibroblast (alpha-smooth muscle actin, $\alpha$SMact) and additional fibrosis marker (Collagen 1a1, Col1a1) were also decreased on the surface of numerous drug-encapsulating hydrogel implants, in a similar fashion, as compared to fibrosed controls.

Figure 11A:
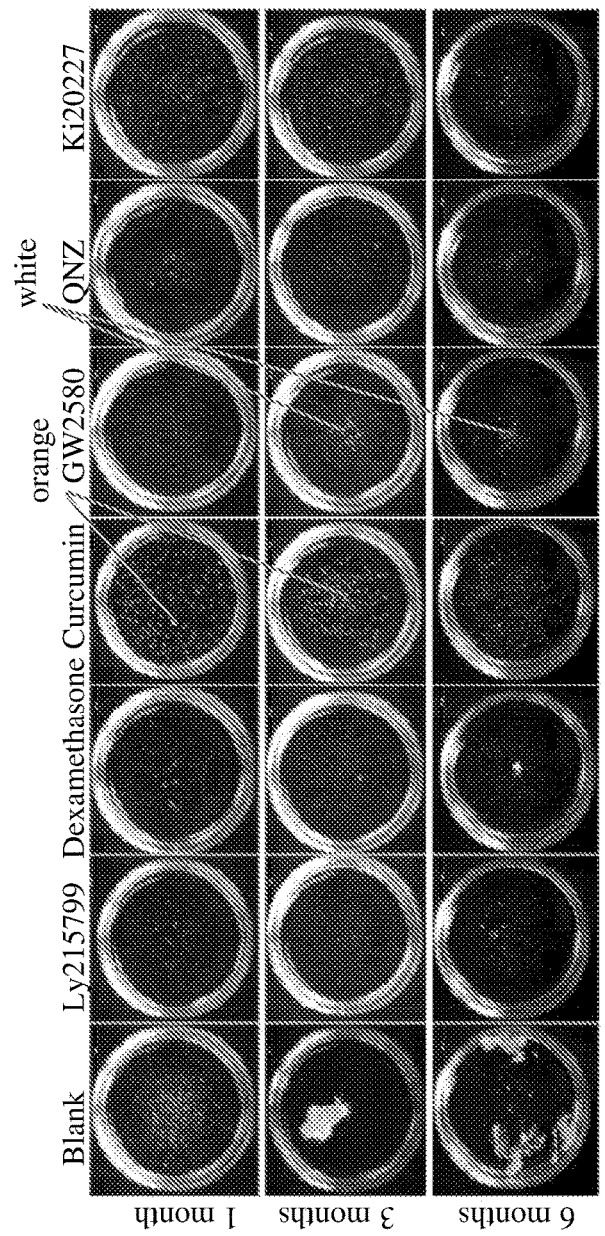
FIG. 11A. Phase contrast images showing host foreign body response (immune cell adhesion and fibrosis), observed as yellowish-white plaque on the otherwise translucent alginate microspheres. Importantly, a number of these anti-inflammatory agents and more targeted small molecule inhibitors showed improved efficacy to prevent fibrosis after 1, 3 and 6 months of being implanted in the intraperitoneal (IP) space in a C57BL/6 mice. Note: drug crystals have a colored appearance, making the crystalline drug loaded-alginate capsules more opaque in appearance (e.g., orange for Curcumin, white for GW).
Figure 11B:
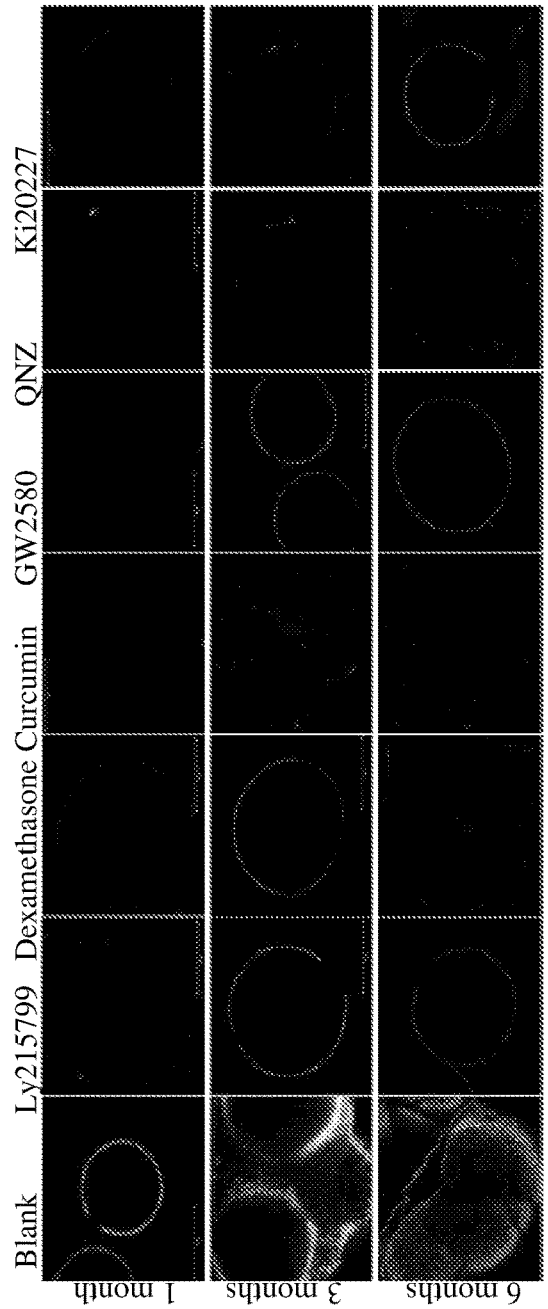
FIG. 11B. Confocal microscopy images showing reduced or no fibrotic overgrowth on numerous crystalline-formulated drugs encapsulated in implanted alginate microspheres (Blue, DAPI nuclear stain; Green, Macrophage CD68; and Red, Fibrosis marker α-smooth muscle actin). Insets: brightfield images of the same fields of view in the main confocal panel.
Figure 13B:
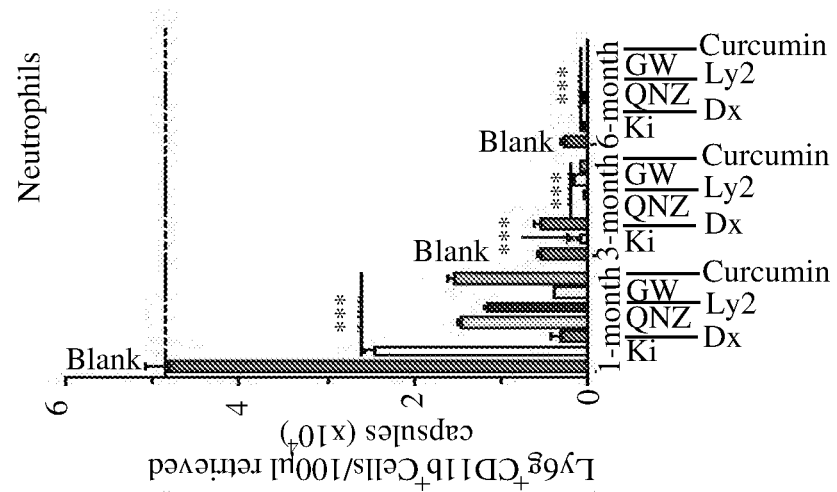
FIG. 13B. Quantitative FACS analysis performed on cells dissociated directly off of alginate spheres, retrieved after various implantation times. Corroborating reduced plaque adhesion and fibrosis, the lead candidates are shown to reduce neutrophil presence.
Figure 13A:
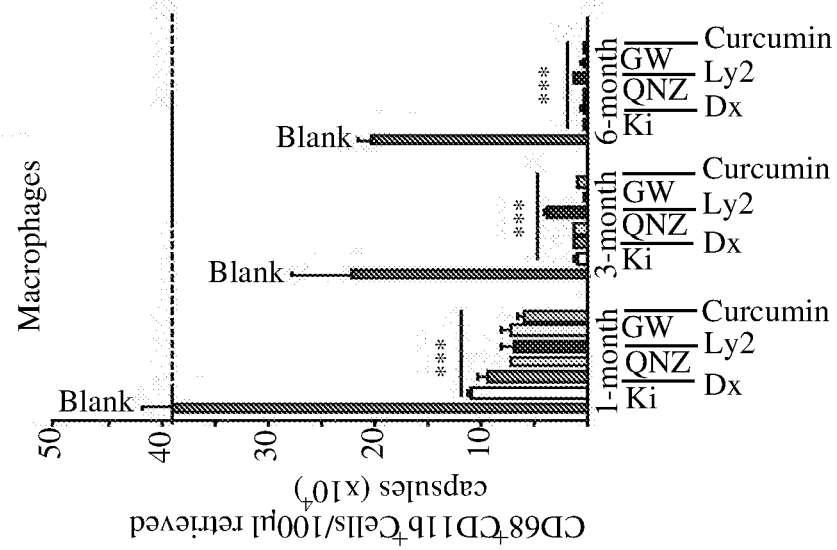
FIG. 13A. Quantitative FACS analysis performed on cells dissociated directly off of alginate spheres, retrieved after various implantation times. Corroborating reduced plaque adhesion and fibrosis, the lead candidates are shown to reduce macrophage presence.
Figure 22A:
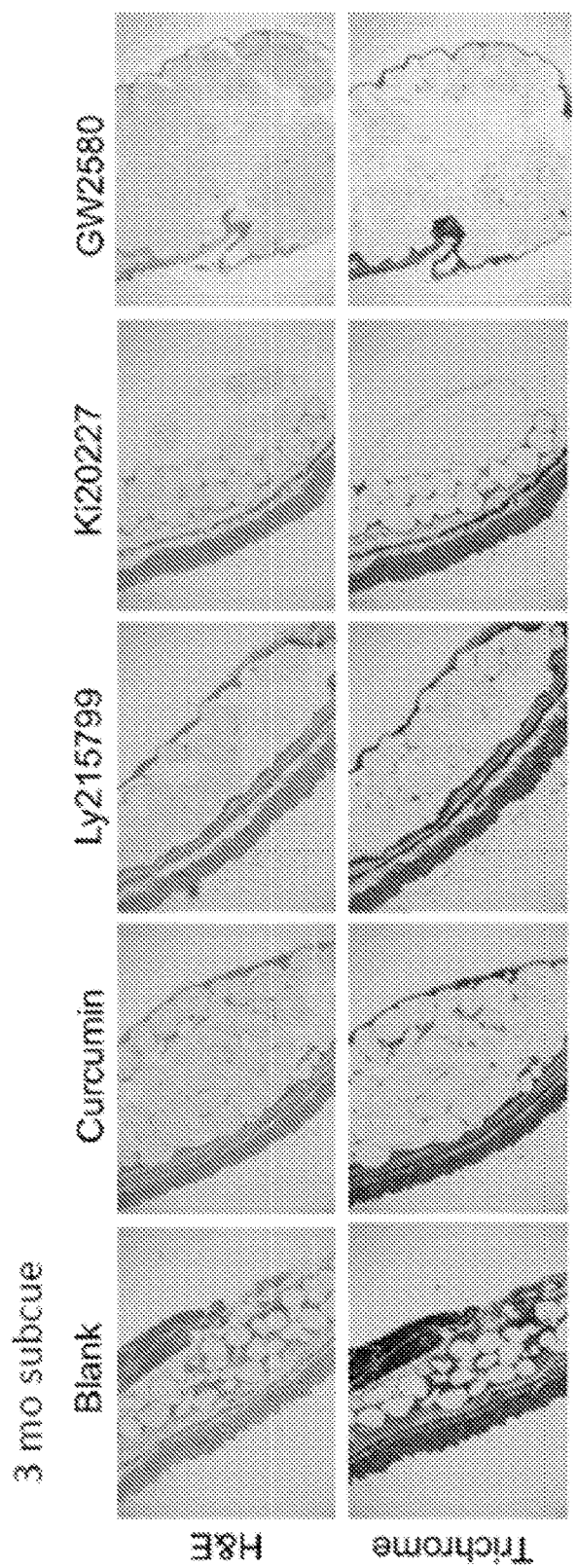
FIG. 22A. H&E and Masson's Trichrome stained histological sections of excised subcutaneous (SC) tissue 3 months post-implant showing reduced fibrosis in various crystalline drug groups, compared to blank (no drug) control spheres (Scale bar=1000 µm; 4×).
Figure 22B:
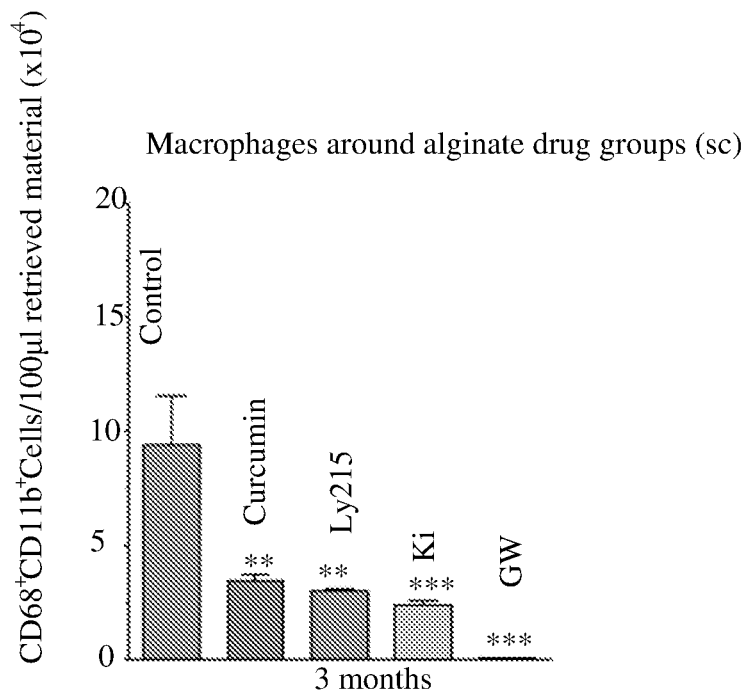
FIG. 22B. FACS analysis for responding macrophages dissociated from spheres shown in FIG. 22A (100 µl material in all cases) 3 months post-SC implantation.

Efficacy of Crystalline Hydrophobic Drug Formulations in the Prevention of Fibrosis Lead compounds identified by screening the amorphous formulations (e.g., compounds of Formulae I-X, particularly LY215799, Dx, Curcumin, GW2580, QNZ and Ki20227) were studied for long-term release and prevention of fibrosis following encapsulation in crystalline form and implantation into the intraperitoneal (IP) space of C57BL/6 mice for long term testing. Drug-eluting capsules that contained the lead compounds in crystalline form were subsequently retrieved after 1, 3, and 6 months from the IP space of C57BL/6 mice, and were determined to be fibrosis free by phase contrast imaging (FIG. 11A) and confocal microscopy (FIG. 11B), as compared to Blank (no crystal) control hydrogel spheres, which exhibited individual fibrosis at 1 month and extensive clumping at 3 and 6 months post-implant (FIGS. 11A and 11B, left columns). FIG. 11A shows representative phase-contrast images showing host foreign body response (immune cell adhesion and fibrosis), observed as yellowish-white plaque on the otherwise translucent alginate microspheres. Importantly, a number of the anti-inflammatory agents and more selective small molecule inhibitors showed improved efficacy in prevention of fibrosis 1, 3 and 6 months after being implanted into the IP space in C57BL/6 mice. Data collected at the 6-month time point also showed prevention of fibrosis, as well as intact crystals still remaining in significant quantities inside retrieved capsules. In addition, FACS analysis (FIGS. 13A and 13B) showed significantly reduced presence of innate immune cell (macrophages, left panel; and neutrophils, right panel) on the surfaces of retrieved crystalline drug-loaded capsule groups, even after 6 months post-implantation. Histological staining (H&E and Masson's Trichrome) determined that numerous crystalline drug-eluting capsule treatment groups (with different drug candidates identified in FIGS. 7-9), showed significantly reduced cellular infiltration and fibrotic (collagen) deposition following 3-month subcutaneous (SC) implantations (FIG. 22A). FACS analysis of cells taken from retrieved and dissociated SC tissues and capsules showed significantly reduced macrophage levels on the surface and around implanted DECs (FIG. 22B). To determine whether fibrosis-free capsules were due to local or global immunomodulation, plasma drug concentrations were monitored throughout the study by LC-MS and the observed levels were not only below the reported $IC_{50}$ (0.5-10 ng/ml) values of the corresponding drugs (FIGS. 22C and 22E) but also non-detectable within 1 to 2 weeks post-implantation, depending on whether capsules were placed into the IP or SC sites, respectively, indicating that observed long-term anti-fibrotic effects are likely due to localized as opposed to systemic immunosuppression. Drug extraction analysis by HPLC also determined that notable percentages (e.g., more than 50%) of the loaded drug remained within the retrieved capsules (FIG. 22D), particularly in the subcutaneous implanted samples. These results suggest that fibrosis prevention could continue for a significantly longer period of time. In contrast, capsules retrieved from the IP space 6 months post-implantation were identified with only 2-40% of the loaded drug remaining within the retrieved capsules.

Figure 12:
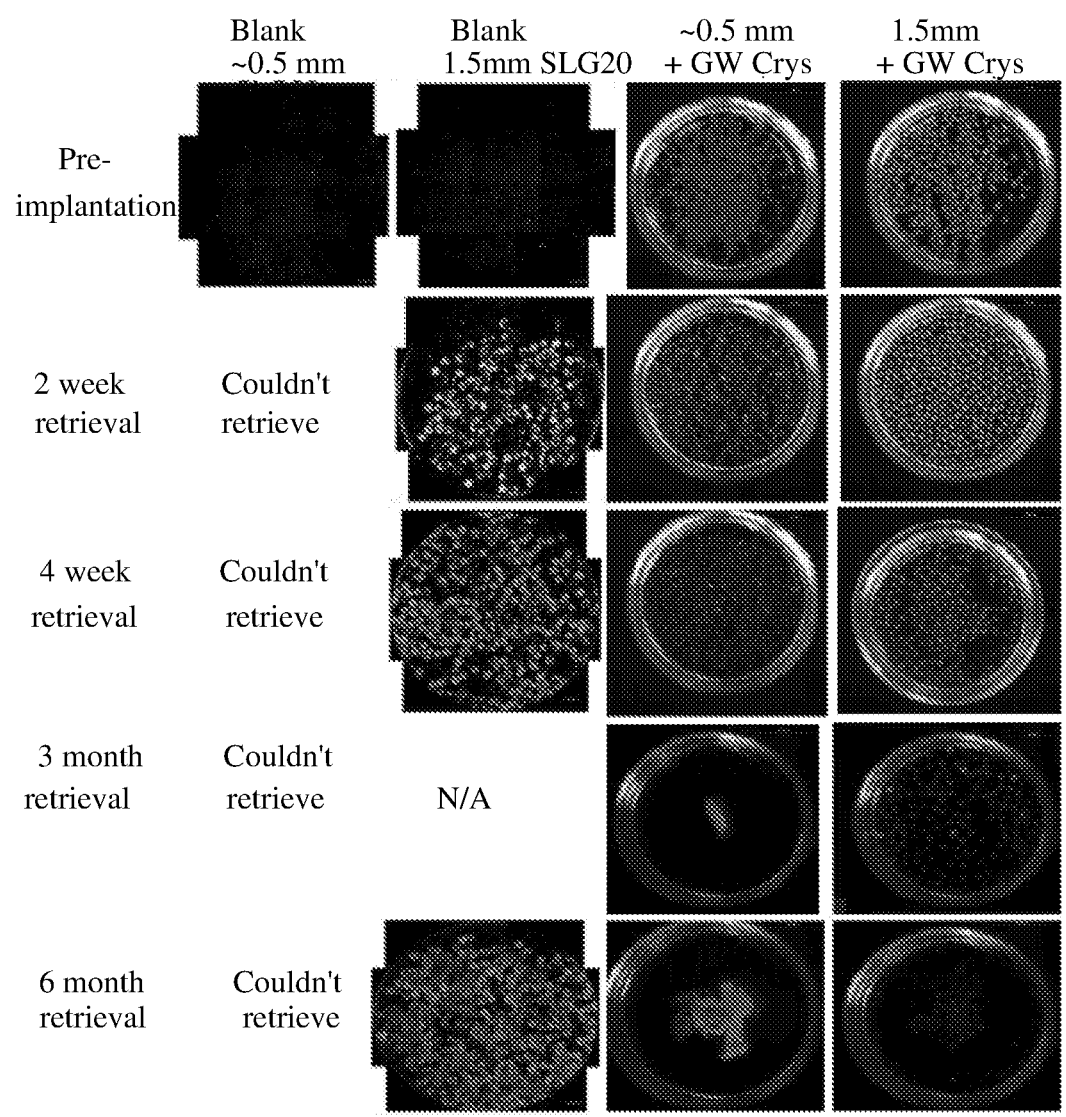
FIG. 12. Phase contrast images showing host foreign body response (immune cell adhesion and fibrosis) against 0.5 and 1.5 mm diameter alginate spheres encapsulating crystalline CSF1R inhibitor GW2580, after 2 to 4 weeks, and 3 to 6 months after implantation into the intraperitoneal (IP) space in non-human primates (NHP); N=2/group. Note: drug crystals have a colored appearance, making the crystalline drug loaded-alginate capsules more opaque in appearance (white for GW2580).
Figure 13C:
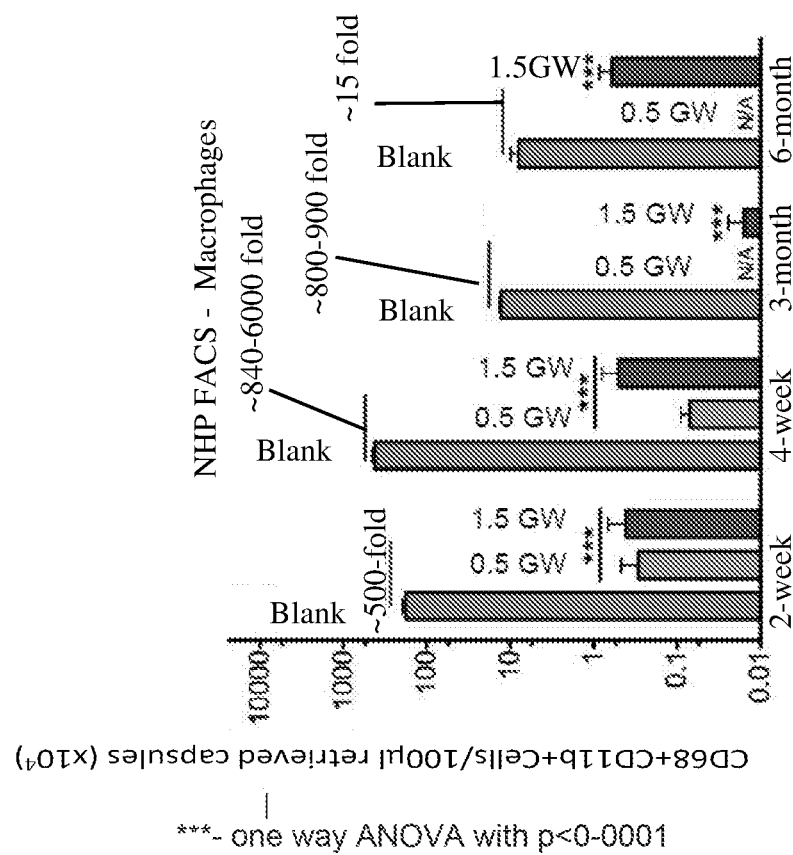
FIG. 13C. Quantitative FACS analysis performed on cells dissociated directly off of alginate spheres of 0.5 mm and 1.5 mm GW crystal data points described in FIG. 12 retrieved after various implantation times. Corroborating reduced plaque adhesion and fibrosis, macrophage presence is reduced multiple orders of magnitude, as compared to empty (control) spheres (log base 10 scale).

Lead candidates identified in these studies, like GW2580, were subsequently tested in a non-human primate (NHP) model in which capsules (0.5 and 1.5 mm) were implanted in both the intraperitoneal (IP) and subcutaneous (SC) spaces (FIGS. 12 and 13C). Phase contrast images of controls revealed massive host foreign body response (immune cell adhesion and fibrosis), and 0.5 mm control capsules were irretrievable as they completely fibrosed and stacked in the IP space. In contrast, both sizes of capsules loaded with crystalline GW2580 showed a significantly high efficacy and prevented fibrosis development after 2- and 4-weeks in both IP and SC spaces (FIG. 12). Remaining drug was extracted from retrieved capsules and quantified by HPLC, showing additional stores in 1.5 mm capsules in both the IP and SC sites for up to 6 months, while 0.5 mm capsules only had remaining drug in the SC site at 6 months but little to no drug at 3 months in the IP space (FIG. 23A). These results correlated with the extent of observed foreign body response in each case, and furthermore suggesting a faster release in the IP compartment relative to the SC site. IP space (lavage) drug concentrations were traced by LCMS fort each capsule type following retrieval time points, and found to drop from only 2-3 ng/ml at 4 weeks post-implantation to below detectable limit (0.5 ng/ml) beyond. Plasma sample analysis at the termination of the study also indicated concentrations below detection limits, attributable to slow release and localized delivery. Any cells present on retrieved capsules were dissociated, stained, and analyzed by FACS, which showed significant inhibition of macrophage responses in all cases of remaining drug (FIG. 13C). Excised tissue obtained from the implant sites of drug-loaded alginate 0.5 and 1.5 mm capsules were examined through histological analysis (H&E and Masson's Trichrome staining), demonstrating the lack of sphere embedding and collagen deposition over the same timeframes (FIGS. 23B-23C). And while 0.5 mm drug-loaded capsules became clumped at 3 months, they were not extensively embedded into surrounding omental tissue until 6 months (FIGS. 12, 23B and 23C). These results show promise for clinical translation of such crystalline drug release strategies for long-term delivery and fibrosis prevention.

Figure 14:
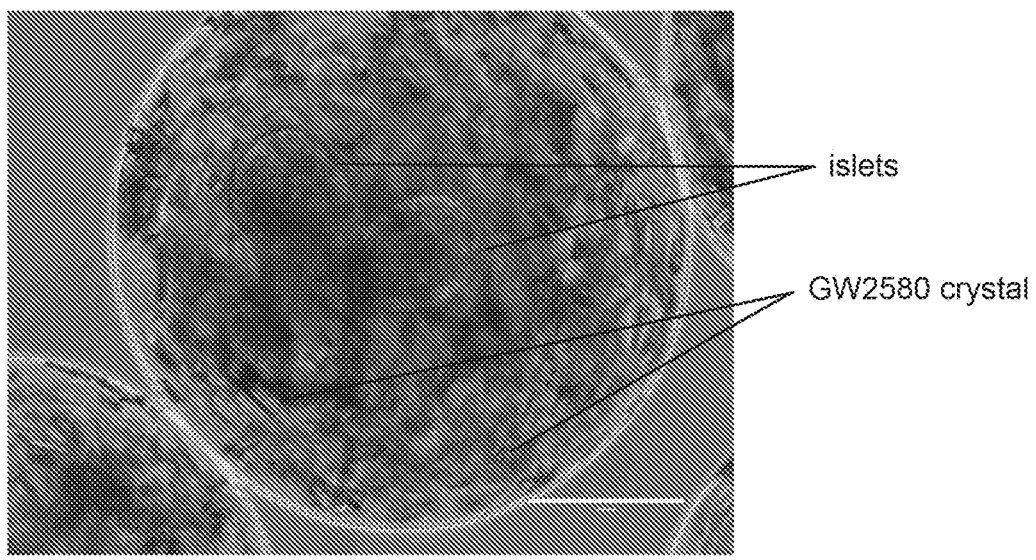
FIG. 14. Representative microscope image of co-encapsulated islets (yellow, round cell cluster) and crystalline drug (GW2580) in alginate microspheres.
Figure 15:
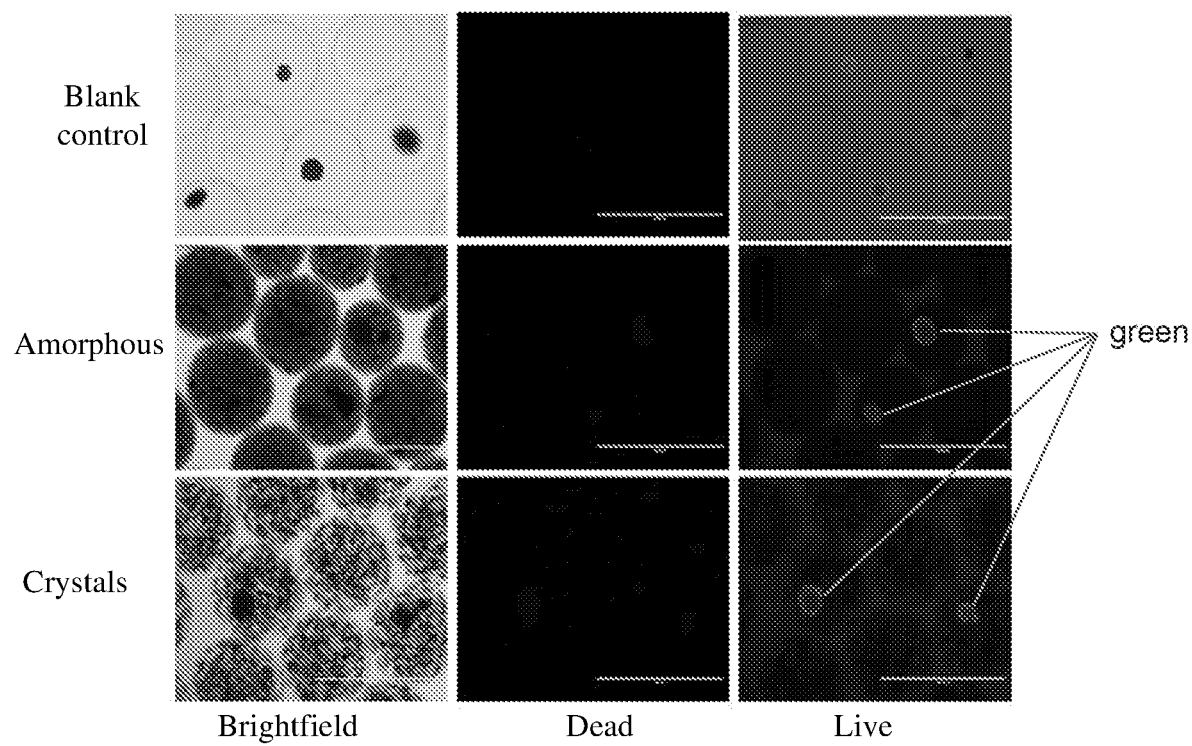
FIG. 15. Representative images of islet-encapsulating blank (no drug) (top), amorphous (middle), or crystal-loaded (bottom) alginate microspheres (islets visible as dark black circles in the left brightfield images). Neither amorphous nor crystalline formulated GW2580-loaded microspheres exhibited islet cell toxicity, as shown by the lack of red stain (middle column), and presence of viability green stain (indicated by the arrows in the right column), in the same position as the islet clusters observed in the (left) brightfield images. For each treatment, all three images are of the same field of view, focus and magnification.
Figure 16:
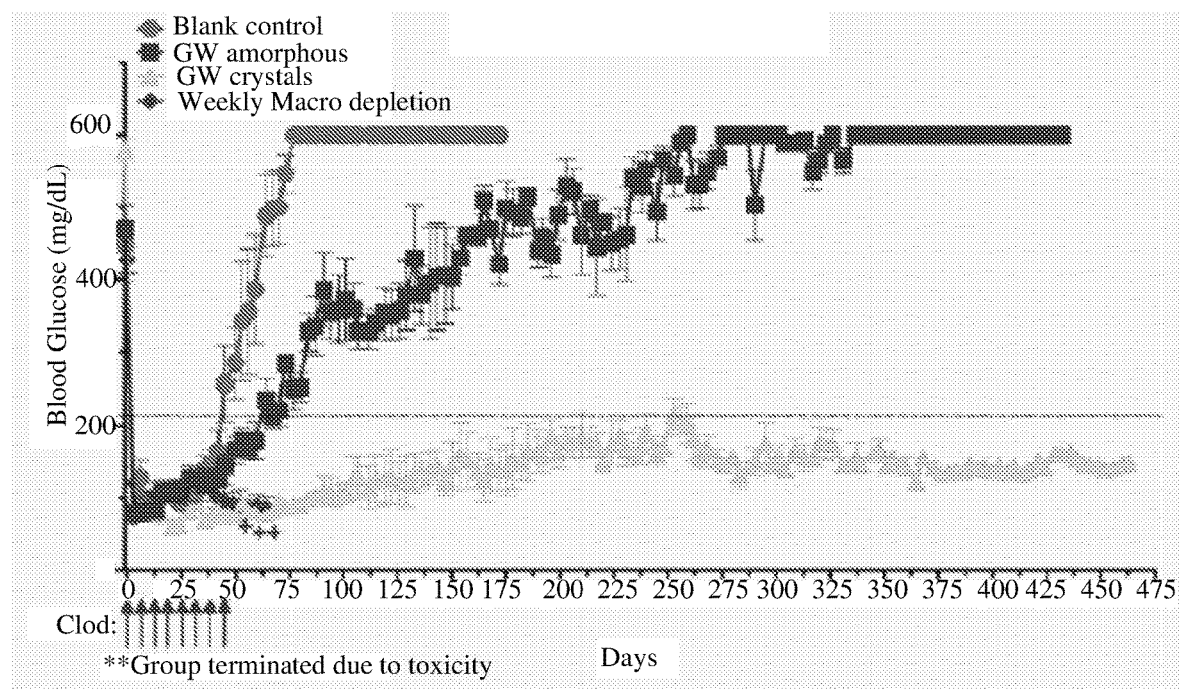
FIG. 16. Blood glucose curves showing prolonged normoglycemia with crystalline GW2580 alginate capsules. Approximately 500-600 μm-diameter alginate microspheres, co-encapsulating 500 IE (islet equivalents) islets with or without drug formulations (no drug, solid circle; amorphous fine powder drug, solid square; or crystal drug, solid triangle). Control (no drug) capsules failed after approximately 40 days in STZ-induced diabetic C57BL/6 mice, due to accumulating fibrosis resulting in loss of islet viability and treatment efficacy. In contrast, amorphous drug-loaded capsules showed a delayed loss of normal blood glucose (below 200 mg/dL) maintenance after almost 70 days, while slow, long-term release crystalline drug formulation-loaded capsules preserved cures in diabetic mice for over 15 months (experiment terminated to analyze samples). Illustrating that macrophage modulation/inhibition is just as good and sufficient as elimination/depletion, crystalline drug treatment (solid triangle) is just as effective as macrophage-depleting clodrosomes (Clodro, liposomal clodronate), administered weekly as required (arrows).
Figure 24:
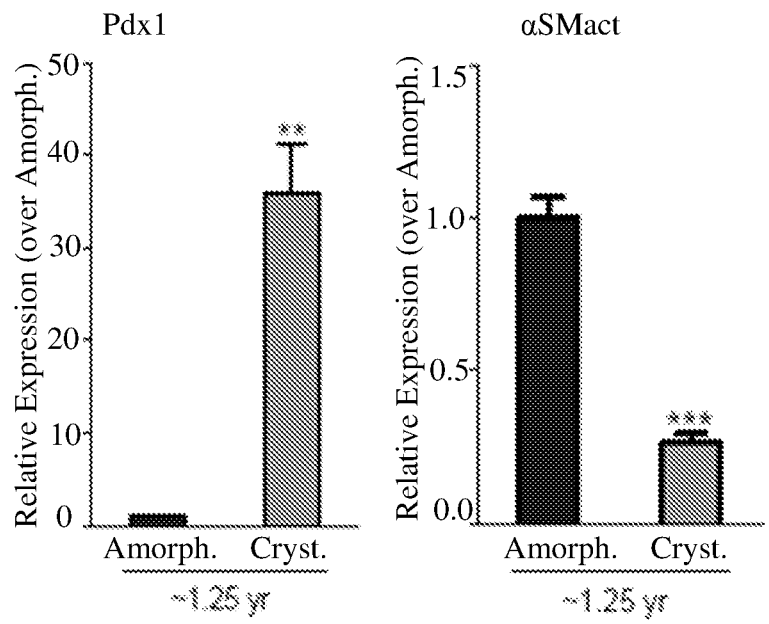
FIG. 24. Rat PDX-1 and host alpha smooth muscle actin expression from capsules retrieved from STZ treated mice at approximately 400 or 460 days (about 1.3 years) post-transplant, respectively for amorphous and crystalline GW2580 (GW) groups. Error bars, mean±SEM. n=5 mice per treatment. All experiments were performed at least two or three times. Statistical analysis: one-way ANOVA with Bonferroni multiple comparison correction : $p<0.001$, and *: $p<0.0001$.

Crystalline and amorphous formulations of GW2580, identified as the lead drug candidate, were encapsulated with β-cells (FIG. 14) and introduced into STZ-induced diabetic C57BL/6 mice to evaluate rat islet survival within conventionally-sized 0.5 mm microcapsules, without drug, compared to those with co-encapsulated crystalline or amorphous GW2580. Dead/live imaging analysis of capsules loaded with crystals and cells, was performed (FIG. 15). Results show that GW2580, in two forms—amorphous and crystalline, is non-toxic to co-encapsulated rat islets, despite a visually significant drug load. Furthermore, both drug formulations were capable of preventing loss of glucose correction for dramatically extended periods of time (FIG. 16). Approximately 500 µm-diameter alginate microspheres, co-encapsulating islets of about 500 IE (islet equivalents) with or without drug formulations (macrophage-targeted, CSF1R inhibitor GW2580), were used in the experiment. In addition, blood glucose was monitored during the study for more than 200 days (Controls, FIG. 16, solid circle) failed, on average, by approximately 35 days post-transplant, while amorphous (FIG. 16, solid square) and crystalline (FIG. 16, solid triangle) formulated capsules maintained normoglycemia for either over 70 days (2-fold improvement) or, much more significantly, over 15 months or 460 days (approximately 13-fold improvement), at which time mice were terminated to analyze remaining capsules. Furthermore, while macrophage depletion by clodrosome (positive control) was initially just as good at maintaining normoglycemia, prolonged weekly delivery eventually caused significant toxicity by approximately 50-60 days post-transplantation (FIG. 16, solid diamond). Cures were elongated from only approximately 4-6 months with previous 1.5 mm capsule studies to over 15 months using instead conventionally sized 0.5 mm capsules that are loaded with drug, suggesting the improved utility of crystal formulated GW2580 in preventing fibrosis and maintaining islet viability. A significantly larger amount of GW2580 remained in the retrieved capsules after 460 days as compared to those earlier taken at 6 months (180 days), suggesting that dramatically longer drug release in the case of cell co-encapsulation resulted due to secretion of globular proteins from biological islets, changing local pH or other microenvironment chemistry to slow dissolution of crystalline GW2580. Explanted long-term amorphous and crystalline drug-containing capsules were analyzed for rat islet function/viability marker Pdx1 and host (mouse) alpha smooth muscle actin (αSMact) expression at approximately 430 or 460 (approximately 1.25 years) days post-transplant, respectively for amorphous and crystalline GW2580 (GW) groups (FIG. 24). Crystal GW2580 capsules had significantly higher islet viability, as indicated by approximately 30-fold higher Pdx1 expression, and lower myofibroblast and fibrosis response, as indicated by 74% lower αSMact expression (FIG. 24). These data illustrate that macrophage modulation/inhibition is as effective as macrophage elimination/depletion, and that crystalline drug treatment is as effective as macrophage-depleting clodrosomes (Clodro, liposomal clodronate) administered weekly.

A long-term anti-fibrosis effect also was achieved with naked (non-encapsulated, stand-alone injectable for therapeutic administration) drug crystals of GW2580. Naked crystals of GW2580 or saline-only (no drug control) were delivered intraperitoneally along with 500 µm alginate spheres for 2 weeks to C57BL/6 mice. Phase contrast imaging of retrieved capsules only showed fibrosis-free, transparent alginate microspheres with daily amorphous drug (3 mg/day for a total of 45 mg over 2 weeks) or much smaller weight amount of drug crystals (4.5 mg, once per week, for 9 mg total) (FIG. 17A). Weekly amorphous drug was not effective, suggesting that the fine powder, capable of achieving burst release, did not provide a similar reservoir of remaining drug for extended anti-fibrotic activity. Furthermore, differential interference contrast imaging of IP lavage liquid rinsed from mice 2 weeks after material implantation, and 1 week since the second and the last crystal injection, showed that many crystals remained within the IP space (FIG. 17 B), indicating that polymer encapsulation is not a requirement for long-term drug release from crystalline drug. Brightfield and fluorescence imaging was used to emphasize the respective presence or lack of fibrotic overgrowth on retrieved alginate spheres from either saline (control) or crystalline GW2580 treatment groups (FIG. 17C). FACS confirmed significant reductions in macrophage levels on non-fibrotic microspheres (FIG. 17D). GW2580 crystal testing (at doses of 0.5 and 5 mg/SC site) was also extended into the SC implant space with other immunogenic materials, ceramic glass (GL) and polymer polystyrene (PS). H&E and Masson's Trichrome staining confirmed significant anti-fibrotic effects of crystalline GW2580 with PS in SC tissues at 2 weeks post-implantation (FIG. 17E). While anti-fibrotic effects were also observed with GL, histological assessment could not be carried out due to not being able to section through ceramic glass. FACS analysis, however, was used to confirm significant reductions in responding macrophages to SC-implanted PS and GL 0.5 mm spheres 2 weeks post-implant (FIG. 17F). Drug extraction of nearby tissue also confirmed large quantities of remaining drug for all implant groups attributable once again to the slowly releasing crystals (FIG. 17G).

Figure 18A:
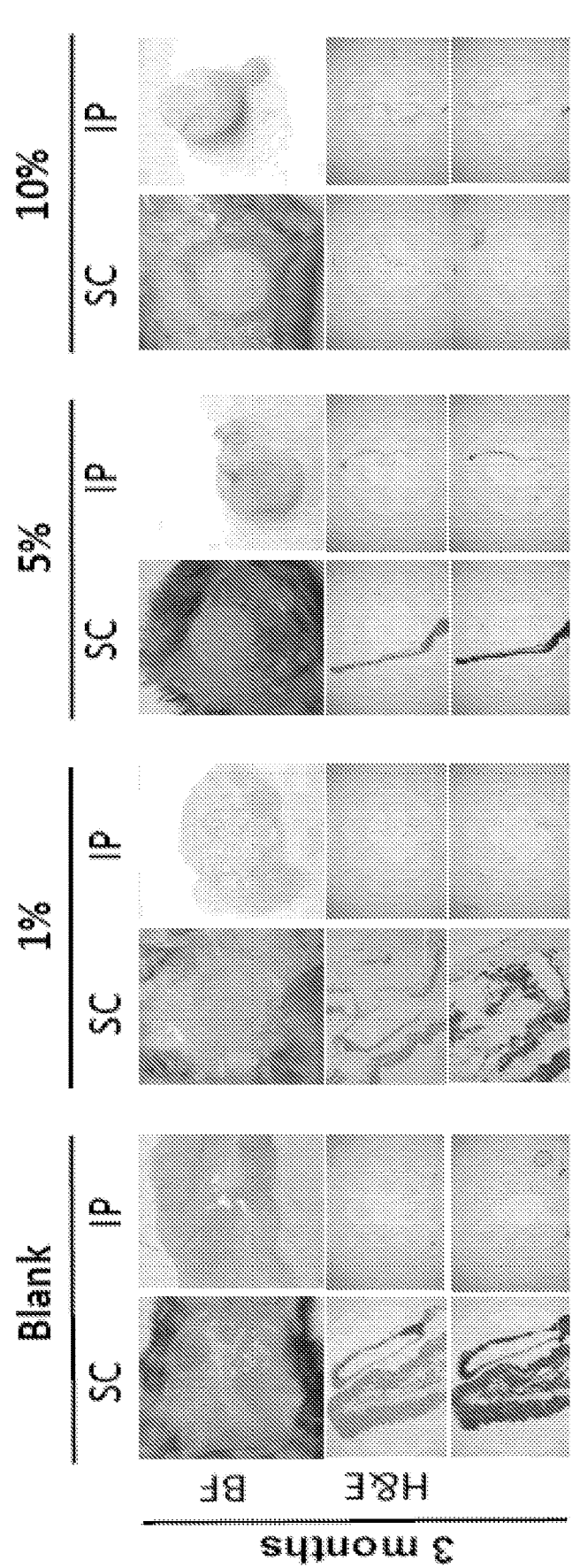
FIG. 18A. Photos (upper panel represented by the label BF) showing host foreign body response (immune cell adhesion and fibrosis), observed as yellowish-white plaque on cured PDMS discs, loaded with 0 (Blank), 1%, 5%, or 10% crystalline GW2580, and retrieved after 3 months following implantation into either the subcutaneous (SC) or intraperitoneal (IP) space in C57BL/6 mice. H&E (middle panel represented by the label H&E) and Masson's Trichrome (lower panel) stained histological sections of excised SC and IP tissue 3 months post-implant showing reduced fibrosis in various crystalline drug groups, as compared to blank (no drug) control discs (Scale bar=1000 μm; 4×).
Figure 18B:
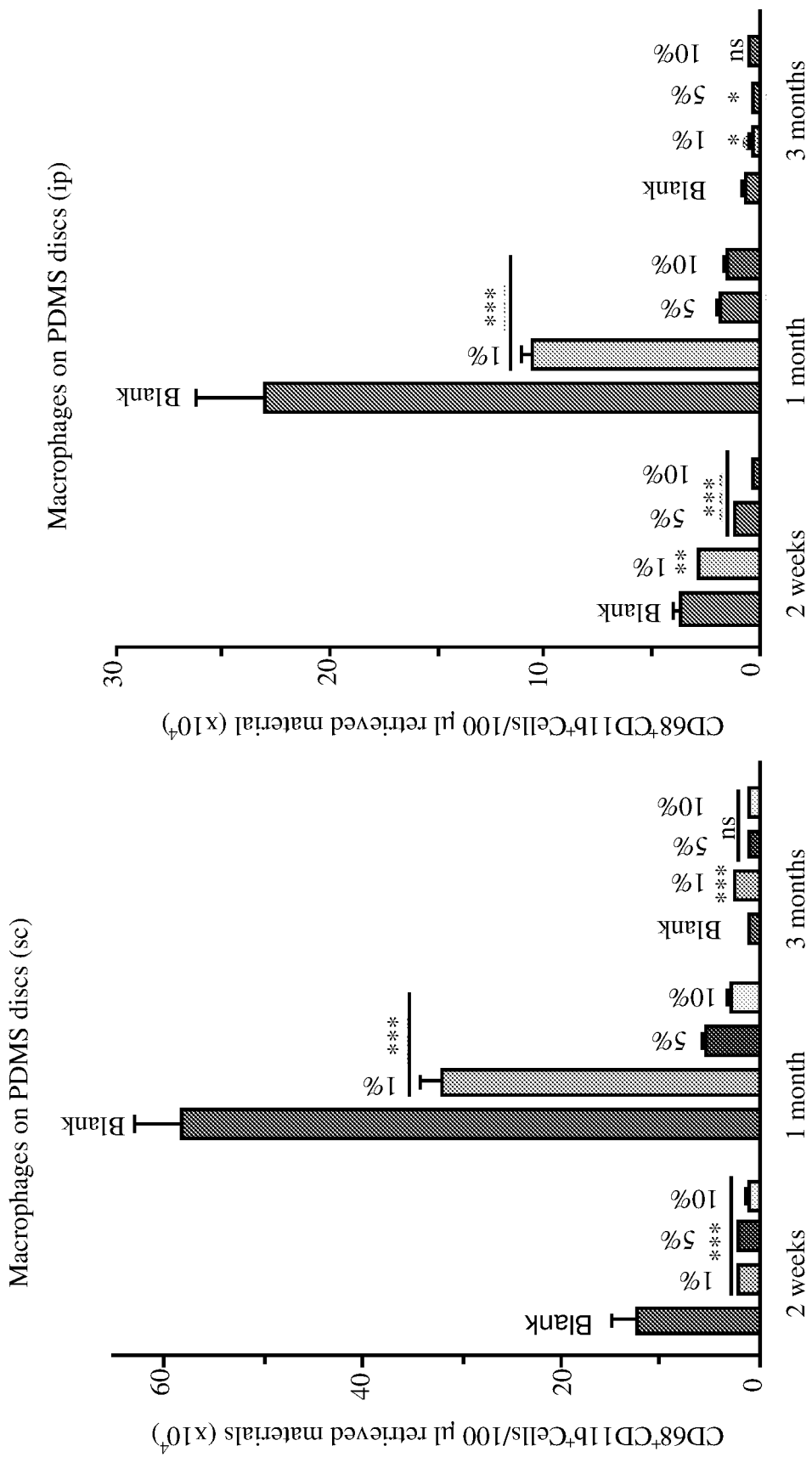
FIG. 18B. FACS analysis of macrophages dissociated from discs (1/site/mouse) 3 months post-SC and IP implantation.
Figure 18C:
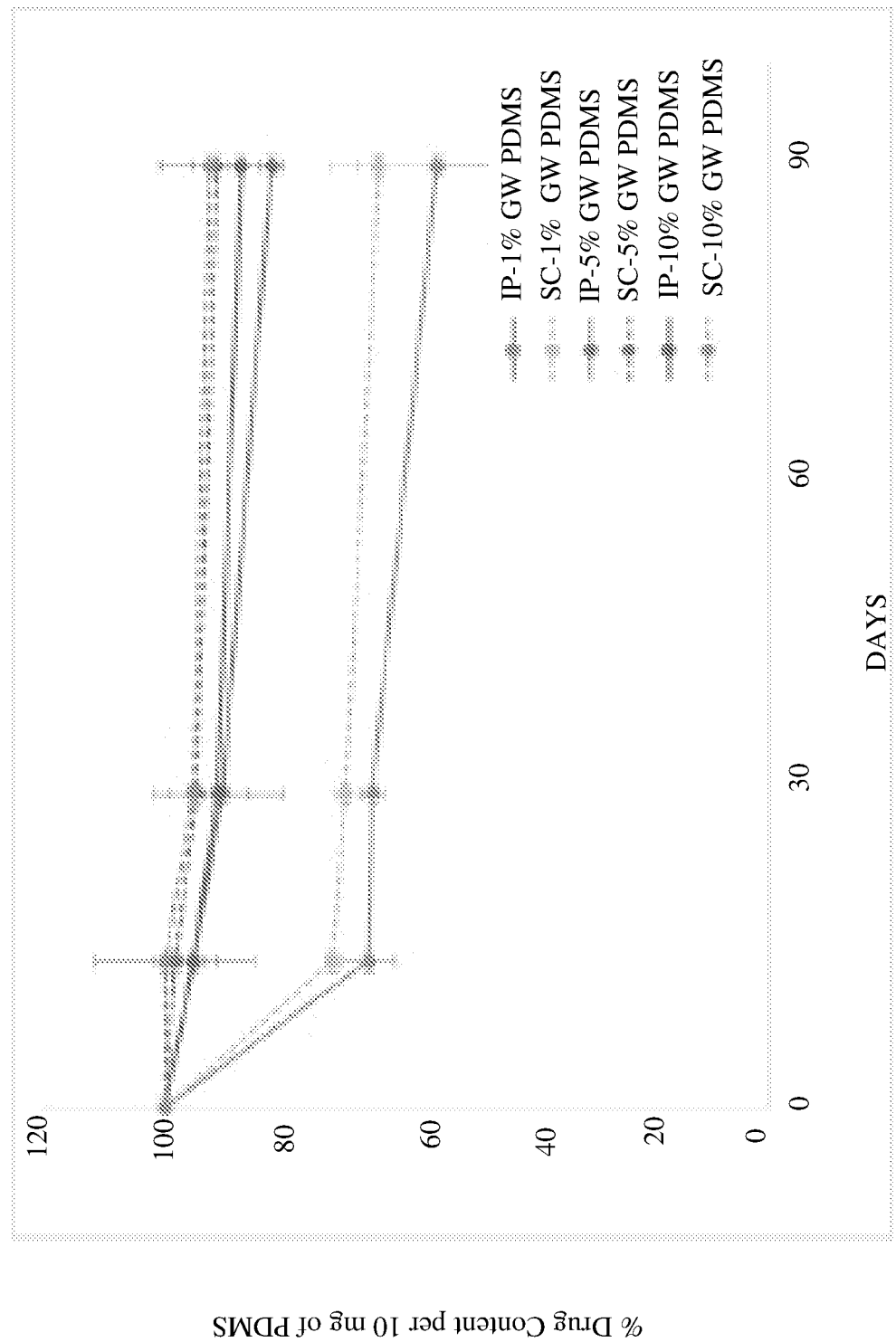
FIG. 18C. HPLC determination of remaining drug levels (% loading) following either SC (1% drug loaded-●, 5% drug loaded-■, 10% drug loaded-▲) or IP (1% drug loaded-○, 5% drug loaded-□, 10% drug loaded-△) 3-month implantation. Data: mean±SEM, n=5. Statistical analysis: one-way ANOVA with Bonferroni multiple comparison correction *: $p<0.05$; : $p<0.001$, and *: $p<0.0001$; ns=not significantly different. Experiment repeated at least 2 times.
Figure 22C:
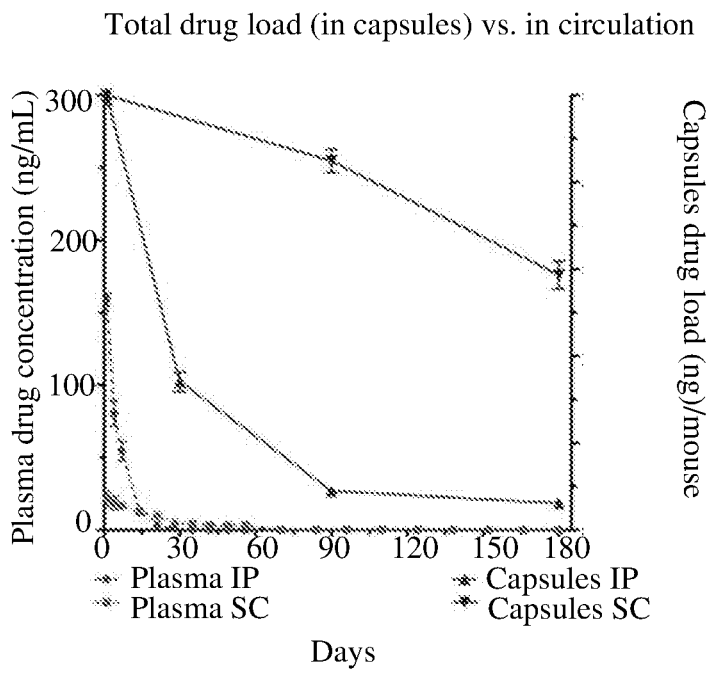
FIG. 22C. LCMS determination of plasma drug levels (Left y-axis) vs. capsule drug levels (Right y-axis) following either SC or IP implantation (Drug used: GW2580).
Figure 22D:
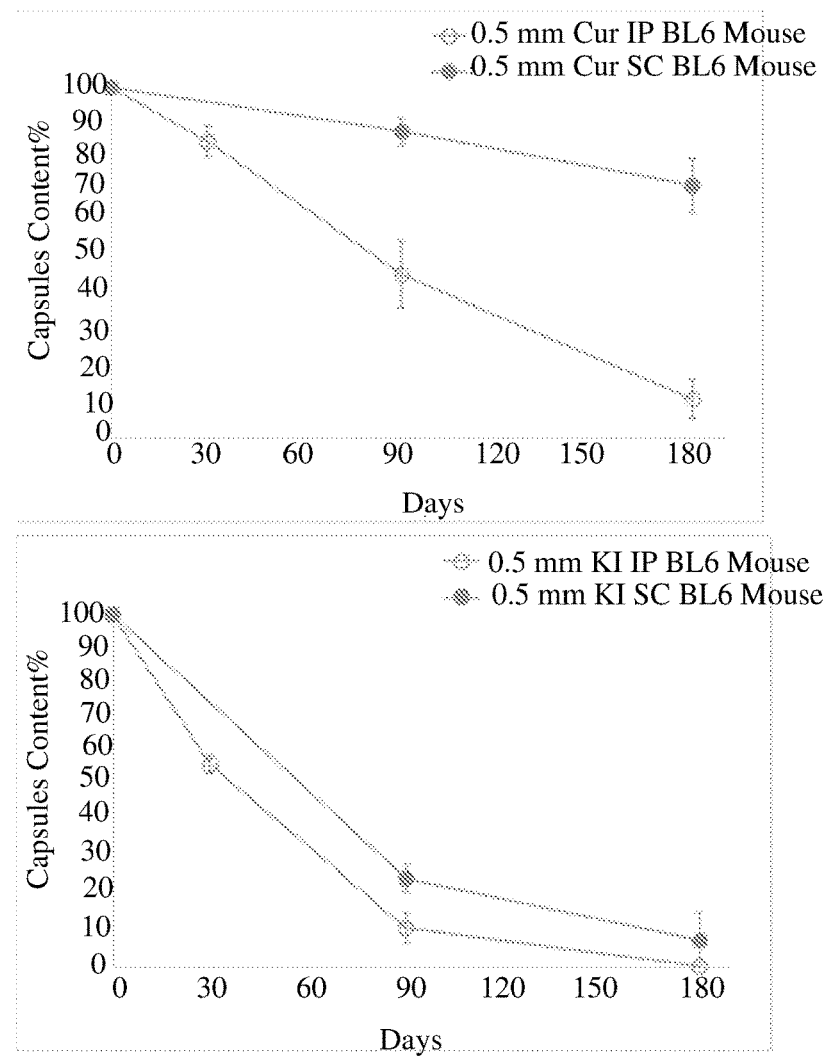
FIG. 22D. Capsule drug content after retrievals and drug extractions over 1, 3, and 6 months (SC-● & IP-○) for crystalline Curcumin (top) and crystalline Ki20227 (bottom).
Figure 22E:
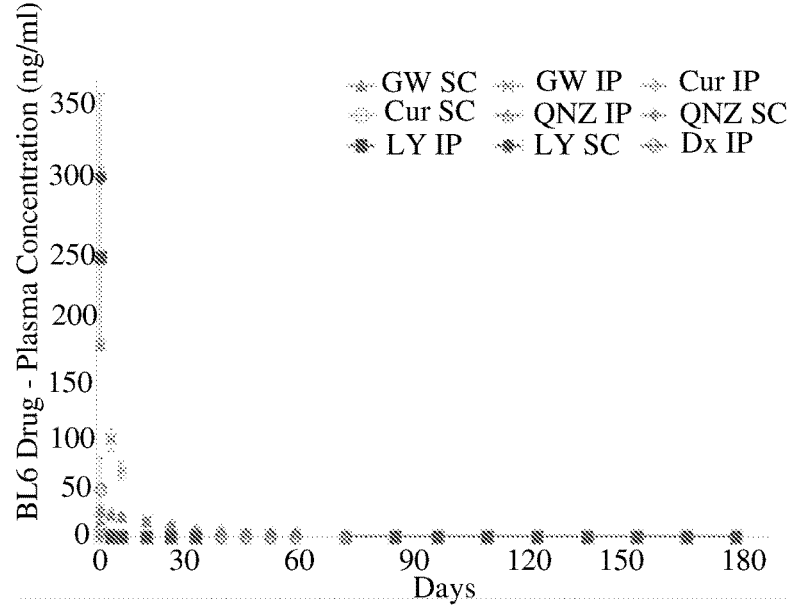
FIG. 22E. Plasma drug concentrations from numerous crystalline-drug formulations (implanted SC-▲ GW profile, □ Curcumin profile, ◆ QNZ profile, ● LY profile or IP-x, GW profile, ◇ Curcumin profile, △ QNZ profile, ■ LY profile, ○ Dx profile as specified) showing no detectable drug in many cases by 4-7 days. Experiments repeated at least 2-3 times.

Another study was done by mixing GW2580 crystals at different ratios of 1, 5 and 10% w/w with PDMS to form disks of 2.2 mm thickness and 5 mm diameter prepared at ratio 9:1 (PDMS: curing reagent) and were solidified overnight at 45° C. These disks were implanted into SC and IP spaces in C57BL/6 mice and then retrieved and analyzed at 2 weeks, 4 weeks, and 3 months post implantation in C57BL/6 mice (1 disc/site/mouse). Foreign body response, observed as yellowish-white plaque on retrieved PDMS discs, was reduced in a dose-dependent fashion by all drug concentrations at 2 and 4 weeks as well as 3 months. The implanted disks exhibited significant reduction in the development of fibrosis (FIG. 18A). H&E and Masson's Trichrome histological staining of excised SC and IP tissues confirmed significantly reduced immune cell infiltration and fibrosis, as compared to blank (no drug) control discs (FIG. 18A middle and bottom panels). FACS analysis for responding macrophages dissociated from retrieved discs showed significantly reduced cell numbers at all time points, for both IP and SC implantations (FIG. 18B). Determination of remaining drug levels (% loading) done by HPLC following either SC or IP implantation for 2 weeks, 4 weeks, or 3-months confirmed that release was slower in the SC space (FIG. 18C). In addition, drug retention was much higher in polymer PDMS, as compared to porous hydrogel alginate over the same incubation times (FIG. 18A vs. FIG. 22C).

Figure 19B:
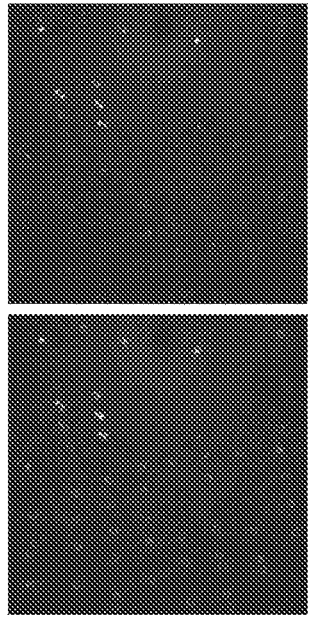
FIG. 19B. Diffraction pattern of images of crystals prepared by solvent evaporation obtained by Single crystal X-ray diffraction (SXRD) shows evidence of crystal twinning.
Figure 19C:
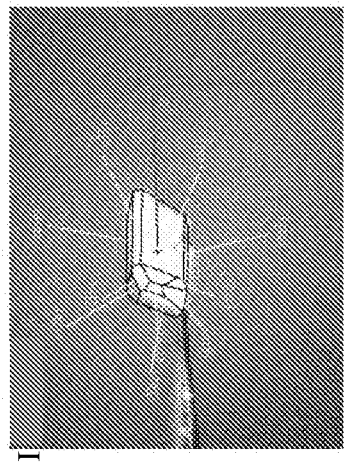
FIG. 19C. Projection image of crystal prepared by the method of the current invention using a solvent:antisolvent mixture (Method II) showing the crystal mounted in SXRD with different surface indexing, and points on the surface (001 or 00-1).
Figure 19D:
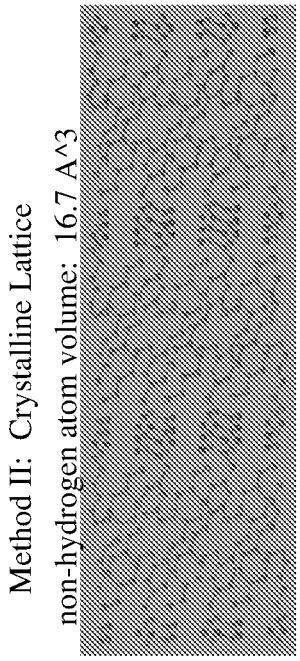
FIG. 19D. Representative image of the GW2580 crystal packing determined by SXRD. Image shows the compact structure of the crystal (higher packing density), which is also quantified and indicated by the low non-hydrogen atom volume.
Figure 19A:
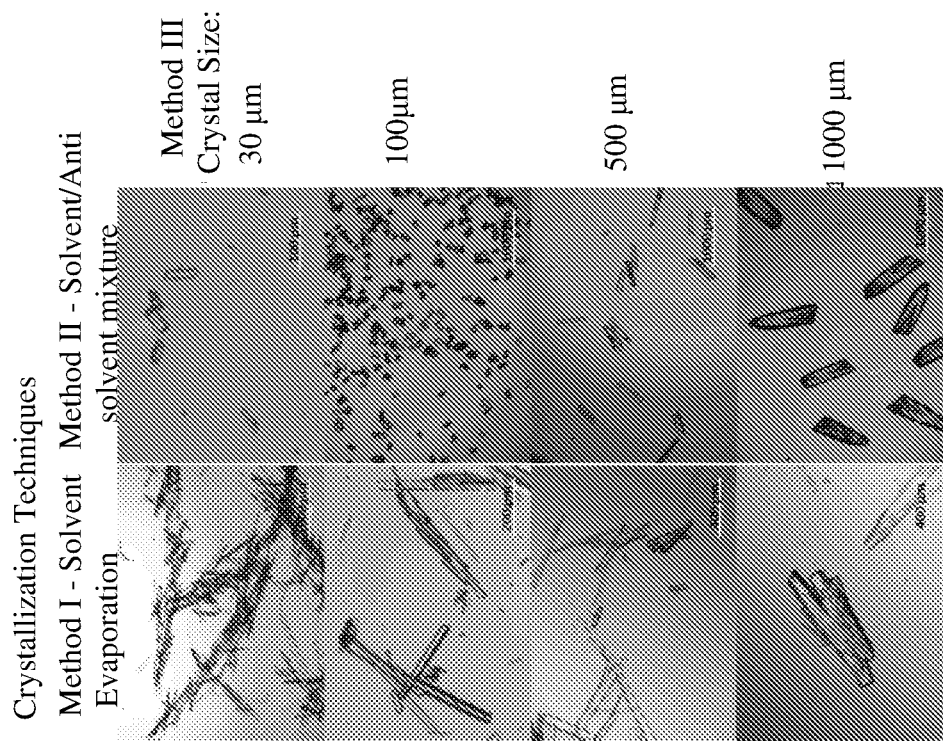
FIG. 19A. Representative images of the crystals obtained by the well-known solvent evaporation method (left, Method I) and the crystals obtained by the method of the invention using a solvent:antisolvent mixture (right, Method II).
Figure 20A:
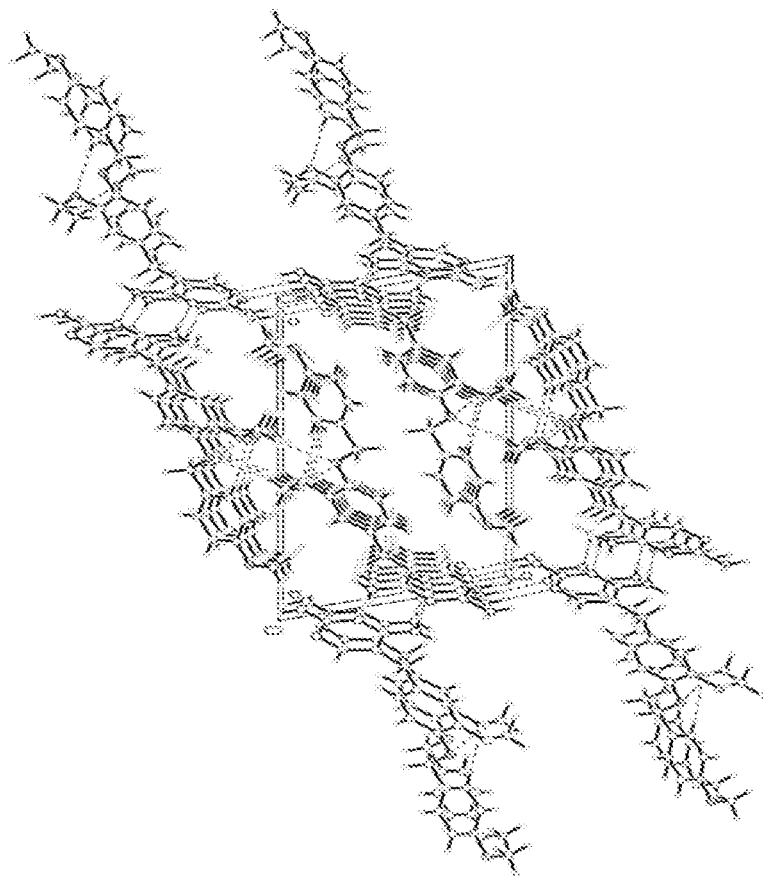
FIG. 20A. Representative image of the crystalline lattice and associated unit cell of the polymorph characterized by single crystal X-ray diffraction (SXRD) of the GW2580 (compound of Formula I) and prepared by the method of the current invention using a solvent:antisolvent mixture (Method II). The crystal packing demonstrates interaction (e.g., hydrophobic, hydrogen bonds) between the different chemical groups within crystalline unit cell and hydrogen bond bridges (semi-crosslinkers) between the different repeating units. This observation correlates with the non-hydrogen atom volume of 16.7 $A^3$ (as shown in table on the right with the data on crystal statistics) for the GW2580 crystal, a value indicating a compact structure with tight packing.
Figure 21A:
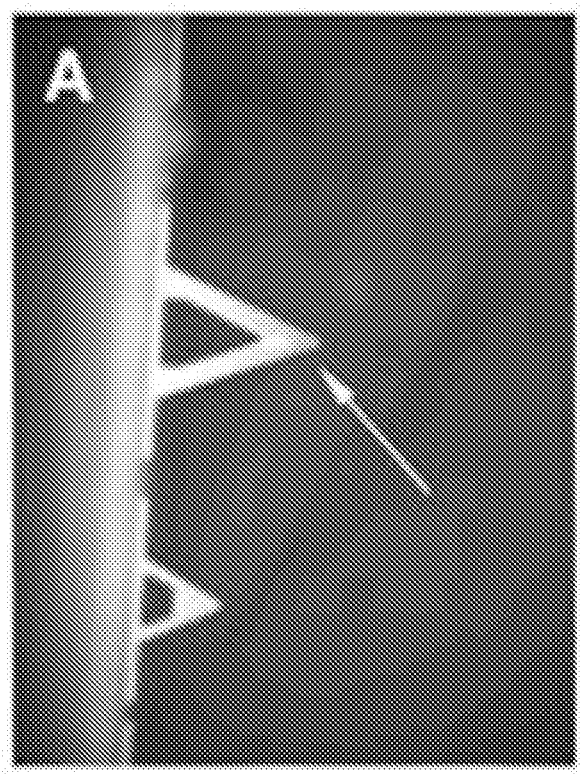
FIG. 21A. Representative image of the cantilever in the atomic force microscope (AFM) that was used for data collection on the specific GW2580 crystal pointing on surface (001) shown in FIG. 19C.
Figure 21B:
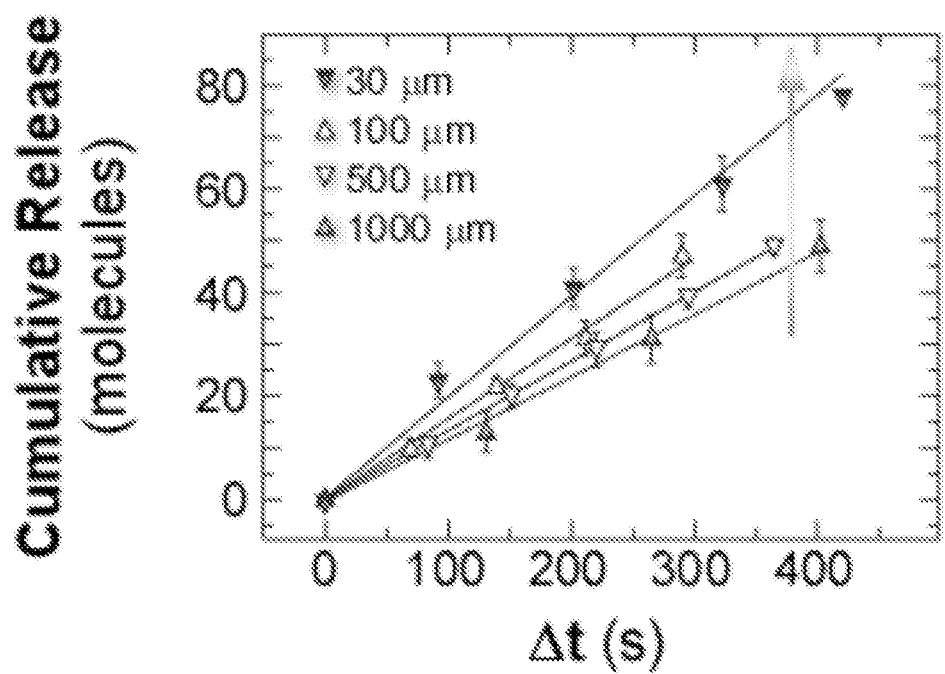
FIG. 21B. A profile illustrating the slow drug release kinetics of defined crystal sizes of GW2580 crystals prepared by the method of the current invention using a solvent:antisolvent mixture (Method II). Drug release by these crystals were monitored by time-resolved in situ atomic force microscopy (AFM) and rates of release were quantified in an undersaturated phosphate buffer (PBS) solution at 37° C.
Figure 21C:
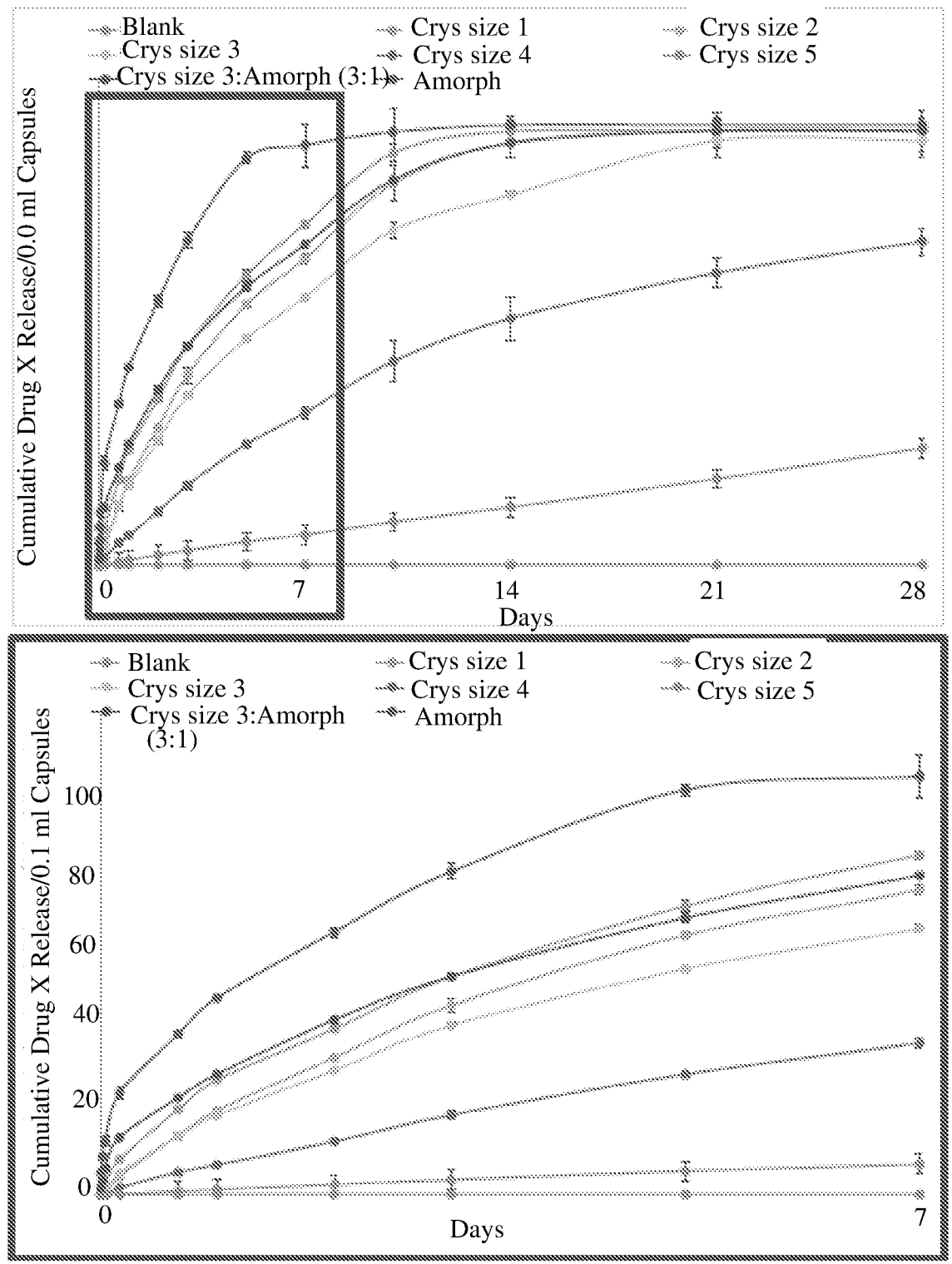
FIG. 21C. In vitro study of GW2580 crystals (prepared by the method of the current invention using a solvent:antisolvent mixture (Method II)) in accelerated release conditions (+ SDS) exhibiting a tunable rate of drug release i.e. for GW2580, encapsulated within 2000 µm alginate capsules. Higher drug release was achieved with encapsulated amorphous form (●brown profile), while pure crystalline formulations (titered into different crystal size ranges, e.g., crystal size 2: 1-20 µm and crystal size 5: 1500-2000 µm) released the drug more slowly initially, but continued releasing drugs for a much longer period of time. The difference between the two profiles was found to be tunable depending on several parameters including crystal size and degree of crystallinity (determined by the presence of at different ratios of amorphous and crystalline material within the encapsulated alginate capsule). Mean+/−SD. Upper panel shows a full time course of accelerated release for 4 weeks while the lower panel shows the release profile over a period of the first 7 days (data within the boxed area of the upper panel).
Figure 21D:
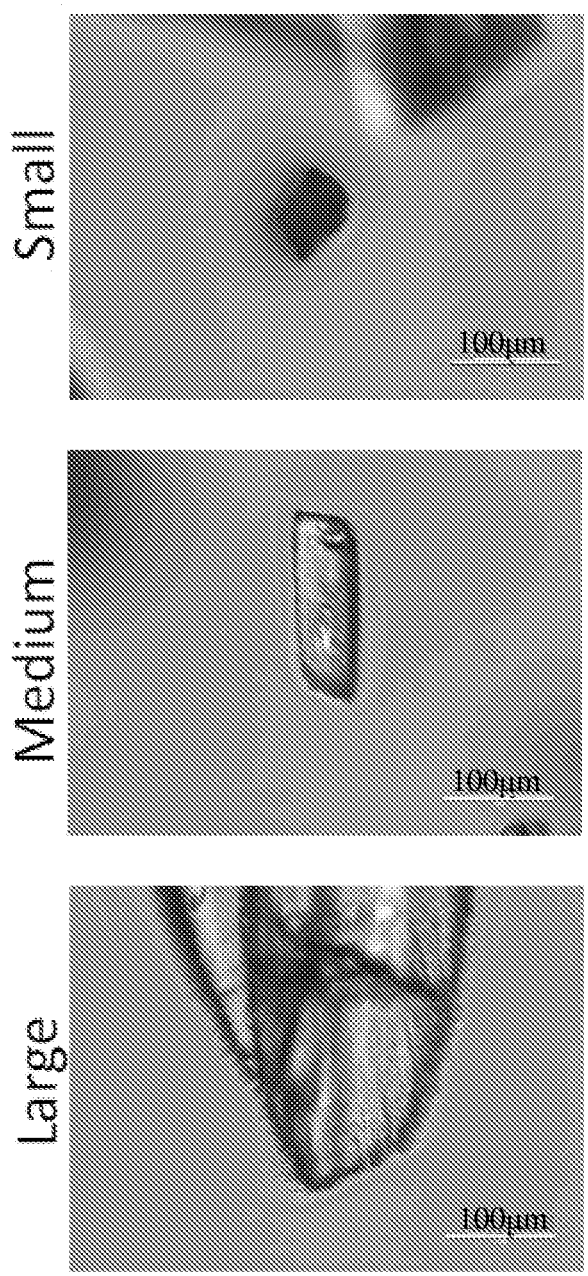
FIG. 21D. Representative images showing slow surface erosion and long-term release of the drug from different sizes GW2580 crystals (top: small, middle: medium, and bottom: large crystals, respectively) loaded into alginate capsules. Smaller crystals, after complete surface erosion, leave behind empty spaces within the 3D alginate, whereas larger crystals remain longer, both exhibiting controlled surface release/erosion.
Figure 21E:
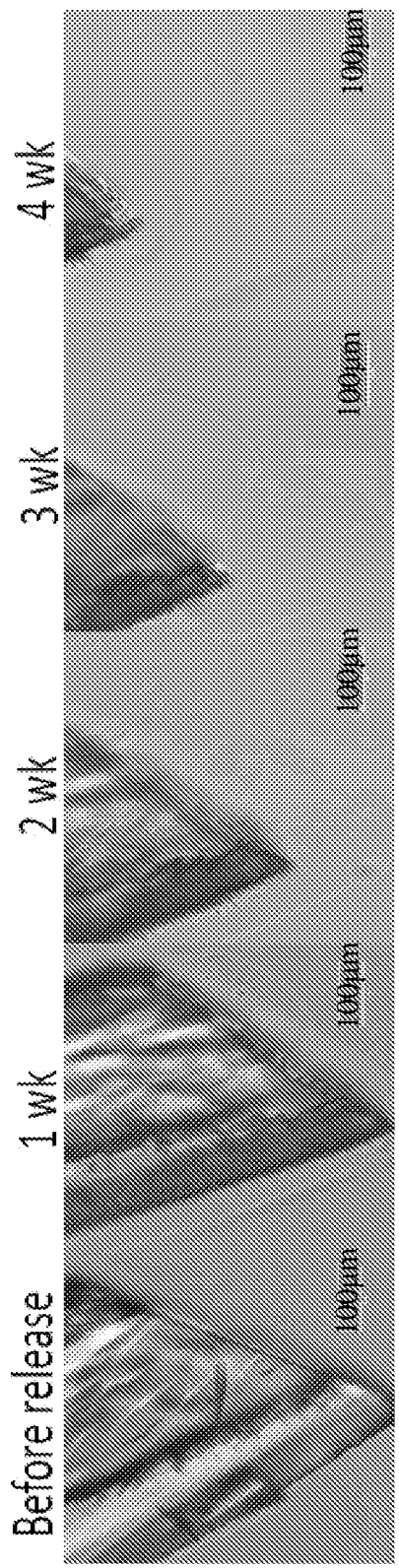
FIG. 21E. Representative images showing slow surface erosion and long-term release of the drug from GW2580 crystals loaded into alginate capsules. The surface erosion in these crystals were monitored for multiple weeks (e.g., 1, 2, 3, and 4 weeks). Experiments were repeated at least 2-3 times.

Crystals of therapeutic agents were required to meet several physical and chemical specifications; therefore, the crystallization process must be carried out under strict environmental control. Characterized properties of crystals include bioavailability, chirality (related to compound molecular structure), morphology, size distribution, and polymorphism. In another study, all drug crystals were prepared using a controlled method-based solvent:antisolvent destabilization technique (referred herein as Method II), and no additives were included during the process, resulting in completely pure crystalline materials. These highly compact, pure crystals had a non-hydrogen atom volume values ranging from about 15 to about 18 $A^3$, as compared to about 18 to about 21 $A^3$ for most already known pharmaceutical crystal formulations. Furthermore, these crystals are utilizable for long-term release and exhibit a layer-by-layer drug release mechanism. FIG. 19A shows representative images of GW2580 crystals obtained using the method described in the current invention (method II, right panel) as well as those obtained by the well-known crystallization method of solvent evaporation (method I, left panel). Solvent evaporation was difficult to control, having low reproducibility, often resulting in random crystal shapes and sizes. A large fraction of crystals obtained by this method (method I) were twinned (FIG. 19B). In contrast, method II using the solvent/anti-solvent mixture, produced highly compact crystals with almost uniform shapes and size ranges (GW2580, right panel). By controlling different parameters such as drug concentration, solvent/anti-solvents mixtures, processing time, temperature, and thermodynamic balance, pure drug formulations, without additives were prepared. Method II also produced highly ordered uniform crystals of variously dimensions (e.g., small, big). Crystal projection using SXRD analysis (FIG. 19C) illustrated a high compact (high packing density) GW2580 crystalline structure with non-hydrogen atom volume of 16.7 $A^3$ (FIG. 19D). Data reduction was carried out with the program SAINT and semi-empirical absorption correction based on equivalents was performed with the program SADABS. The structure was solved with dual-space methods using the program SHELXT and refined against F2 on all data with SHELXL using established refinement techniques (See Methods section). The crystalline lattices for all compounds (e.g., compounds of Formula I-X) obtained by method II showed tight packing due hydrophobic interactions between the drug molecules, inter and intra hydrogen bonds, as well as hydrophobic interphases (e.g., hydrophobic channels seen in GW2580 crystalline lattice shown in FIG. 20A left image). Scanning electron microscope (SEM) images confirmed the difference between amorphous materials and the crystals prepared by method II with uniform crystal fractions (FIG. 20 B). Single, unique polymorphs were identified for each compound (e.g., compounds of Formula I-X), as compared to simulated powder pattern by PXRD (FIG. 20 B).

Mechanisms of drug release for the crystals produced by method II were studied by time-resolved in situ atomic force microscopy (AFM). The real time release of drug molecules from the crystal surfaces was monitored in a physiologically relevant environment. The sequential images of the crystal surfaces were compared to identify the mechanisms of molecule release and quantify the rates of release. The crystals were placed in an undersaturated phosphate buffer (PBS) solution at 37° C. (FIG. 21 A). The crystals produced by method II exhibit a dominant layer-by-layer drug release mechanism. The overall number of drug molecules released from crystals was dependent on the crystal size. For example, lager crystals exhibited a slower release relative to the smaller crystals (FIG. 21 B). The AFM results correlate with the slow rates of drug release observed on a macroscopic level because of the crystals retaining their integrity during exposure to undersaturated solutions, even under accelerated release conditions and/or encapsulated in alginate (FIG. 21 C). Compared to short-term burst release formulations (amorphous drug), crystalline drug allows for highly tunable long-term slow release kinetics, possibly due to compact structure and also tuned size (higher surface area:volume ratio) ranges. Accelerated release was used to yield significantly detectable cumulative release with numerously tuned formulations in vitro over the course of a few weeks (FIG. 21 C) or even months (extrapolation based on remaining drug extraction results.) Release rates can further be modified by incorporating either crystalline drug alone or as a mixed formulation in combination with an amorphous fraction. Crystalline materials not only have the advantage of slow, extended and long-term release but also improved long-term chemical stability. The slow drug release via surface erosion (layer-by-layer) was observed for small, medium, and large crystal sizes (FIG. 21 D), and accelerated release conditions were required to observe this visually in a timely fashion, especially for larger crystals (FIG. 21 E).

CONCLUSIONS

In the screen, it was determined that several agents targeted to TNFα, TGFβ, and CSF1R possess anti-fibrotic efficacy. A lead compound set, targeting the CSF1 receptor, and including compounds GW2580 (LC Labs), Ki20227 (Tocris), and cFMS "Receptor Inhibitor III" (EMD Millipore) demonstrated efficacy in inhibiting fibrosis of implanted biomaterial alginate hydrogel, ceramic, glass, PDMS and polystyrene beads.

In addition to identifying pharmacological agents with anti-fibrotic efficacy, new chemical compound formulation strategies were developed to improve controlled release kinetics, either for short-term burst (as amorphous drug) or long-term slow release (as crystalline formulations), or as a hybrid of the two. By incorporating the same drug loaded either inside a device/carrier, as a surface coating or as a naked injection, therapeutic agent release rates can be controlled, modulated and extended by controlling several parameters, including but not limited to, crystalline degree, crystal size and morphology, etc. Efficacy of localized drug depot of particular agents was demonstrated for injection of naked (non-encapsulated) crystals or encapsulated crystals (both alone and in combination with co-delivered islets). Such formulation strategies allow for extended drug release from days/weeks (e.g., 1-2 weeks with amorphous formulations) to many weeks and/or months (e.g., 240 days with crystalline formulations).

Data described herein demonstrated that varying and optimizing crystalline anti-fibrotic drug formulations (e.g., crystalline degree and compositions, polymorphism, crystal size and morphology etc.) for achieving slow extended release in conjunction with biomaterial and/or medical device implantation, can inhibit host recognition and propagation of foreign body reactions (e.g., fibrosis). The crystals produced by the method described herein (e.g., GW2580 crystals) can be utilized for slow extended release over many months-years in vitro and in vivo. The mechanism of release (e.g., surface erosion) studied by in situ AFM showed that the highly compact crystals (e.g., high packing density) due to the extensive overlapping between the hydrophobic moieties within the crystal and the inter/intra hydrogen bonds (as determined by XRD) likely makes it difficult for water molecules overcoming all of the aforementioned interactions to achieve drug release. Accordingly, numerous drugs, when prepared and formulated in the manner described herein, were capable of sustained and/or delayed release over long periods (e.g., many months) to prevent fibrosis in both the IP and SC implant sites. Sustained and/or delayed release over long periods was also verified in both rodents and non-human primates. Furthermore, crystalline GW2580 (CSF1R small molecule inhibitor) in alginate microspheres of 0.5 mm size demonstrated a significant ability to prevent foreign body (e.g., fibrosis formation) response and maintain viable co-encapsulated islets and normoglycemia in diabetic mice for over 1.25 years. Modulating macrophage response for such extended periods of time with crystalline drug provided significant anti-fibrotic effects for multiple materials encompassing hydrogel alginate, ceramic glass, and plastic polystyrene and PDMS. Localized drug depot efficacy both in a stand-alone naked crystal injection was demonstrated. Such formulation strategies allow to greatly extend drug release from days/weeks (e.g., 1-2 with amorphous) up to many months and/or years for crystalline forms described herein.

Materials and Methods
Materials/Reagents

All in vitro reagents were obtained from Life Technologies (Carlsbad, Calif.), unless otherwise noted. Antibodies: Alexa Fluor-conjugated anti-mouse CD68, Ly-6G/Ly-6C (Gr-1), and CD11b (described below) were purchased from BioLegend Inc. (San Diego, Calif.). For primate immunostaining, anti-human CD68 Alexa Fluor-conjugated antibody was purchased from Santa Cruz (Dallas, Tex.). The same CD11b (anti-mouse/human) antibody (BioLegend) was used for both primate and mouse staining. Cy3-conjugated anti-mouse alpha smooth muscle actin antibody and glass spheres (acid washed) of medium (about 500 μm) size were purchased from Sigma Aldrich (St. Louis, Mo.). Polystyrene spheres of medium (about 400-about 500 μm) size were purchased from Phosphorex (Hopkinton, Mass.). A sampling of materials used in this study were submitted for endotoxin testing by a commercial vendor (Charles River, Wilmington, Mass.) and the results showed that spheres contained <0.05 EU/ml of endotoxin levels (below detectable limits). All the solvents were analytical grade purchased from Sigma Aldrich, USA. Sodium dodecyl sulfate (SDS) was also purchased from Sigma Aldrich, USA. Drugs were purchased from various vendors: rapamycin and dexamethasone (Sigma aldrich), GW2580 (LC Laboratories), LY2157299 and QNZ (Cayman chemical company), curcumin (Enzo), KI20227, A83-01 and D4476 (Tocris), JNJ-28312141 (SYNKINASE), A83-01 and D4476 (Tocris), Lenalidomide (CC-5013, Selleckchem), cFMS Receptor Inhibitor III (Calbiochem), CAL-101 and Lenalidomide/CC-5013 (Selleck Chem) and cFMS Receptor Inhibitor III (EMD Millipore).

Preparation of Crystals

All crystals grown by solvent evaporation induced crystallization technique (e.g., by method I in FIG. 19A), well known to a person of skill in the art, were solubilized in solvents (e.g., acetone, methanol, ethanol, methyl acetate, ethyl acetate, THF, Butanone, dichloromethane and chloroform) and then the solvent was allowed to evaporate at a constant temperature of about 0° C. to about 40° C. (e.g., about 0° C., about 20° C., about 25° C., about 30° C., about 40° C.), resulting in crystal formation. Crystals were then harvested and analyzed with conventional techniques (e.g., macroscopic, single crystal and powder diffraction techniques).

Figure 25:
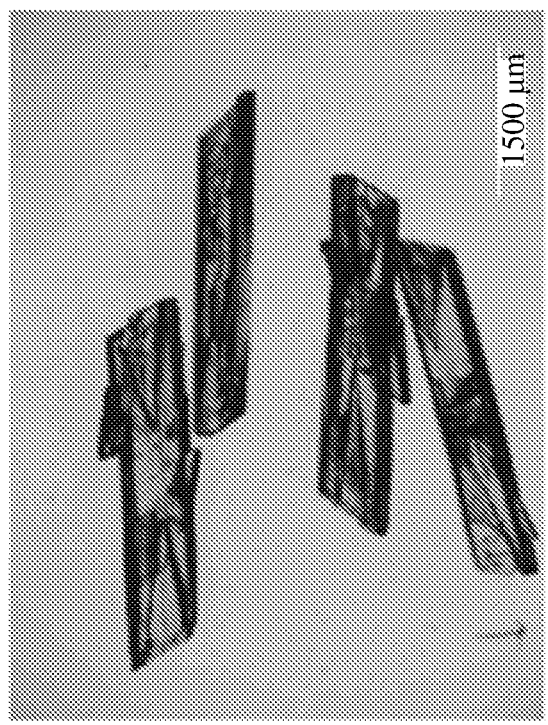
FIG. 25. Representative image of the GW2580 crystals obtained by the method of the invention using a solvent:antisolvent mixture (e.g., method II) with crystals size of about 3 mm.

All crystals grown using solvent:anti-solvent mixing methods (e.g., by method II in FIGS. 19 A, 19 C, 19 D and 20 B) were grown at a constant temperature (e.g., about 0° C., about 20° C., about 25° C., about 30° C., about 40° C.) with concentrations of the hydrophobic compounds ranging from 0.001 mg/mL to 5000 mg/mL. Various solvents (e.g., DMSO, Acetone, Butanone, anisole, Methyl acetate, Ethyl acetate, Acetylptimized acetate, THF, Methanol, Ethanol, Ethanol+THF) and anti-solvents (e.g., Water, Acetonitrile, Methyl acetate, Ethyl acetate, Acetyl acetate, Xylene, Hexane, Heptane, Heptane+Water) mixtures can be used for the crystallization experiments In a particular embodiment, Ethyl acetate was used as a solvent while Hexane was used as an anti-solvent. In several embodiments, Hydrophobic compounds of varying concentrations, for example, 100 mg of Curcumin, 100 mg of dexamethasone, 100 mg of Ly215799, 100 mg of GW2580 and 100 mg of QNZ, were each initially dissolved in 5-150 ml (e.g., 10 ml, 30 ml, 80 ml, 130 ml) of solvent (e.g., ethyl acetate). In some crystallization experiments, solvent solutions were sonicated 0-15 minutes (e.g., about 0 minutes, about 1 minutes, about 10 minutes) and/or pre-heated in a range of about 20 to 80° C. (e.g., about 25° C., about 40° C., about 75° C.) to facilitate solubility. To each of these solutions, anti-solvent (e.g., Hexane) was added in sub portions totaling about 0 to 160 ml per 100 mg of dissolved hydrophobic compound (e.g., about 20 ml, about 30 ml, about 100 ml) depending on the drug and desired final mean crystal size. The process was optimized for minutes hours (e.g., about 1 minute, about 5 minutes, about 10 minutes, about 30 minutes, about 45 minutes) to hours (e.g., about 1 hour, about 2 hours, about 4 hours, about 6 hours, about 24 hour) depending on molecular structure of the compound. The final resulting crystals were analyzed by microscopy methods including SEM analysis for at least 3 sample images per preparation, with 10 random size measurements being taken in each case. Crystalline samples were also analyzed by XRD. Controlling crystal size depends on various conditions that need to be optimized, i.e., drug concentration, solvent:anti solvent ratio, scale, process-time, etc. FIGS. 3 and 20B show representative single crystals of Dexamethasone, Ly215799 and GW2580 respectively, prepared by the method described herein (method II). Crystal sizes ranged from 20 μm up to 3 mm (FIG. 25) and characterized by FIG. 4 shows representative single crystals of curcumin prepared by this method.

Amorphous Materials Preparation

Amorphous Form Prepared for the Drugs in this Study by 2 Methods

No cells encapsulation process: The amorphous material was prepared inside the polymer solution (hydrogel) by dissolving first the drug in an organic solvent (e.g., vehicle) depending on drug solubility (e.g. Ethanol, Methanol, Acetone, DMSO). The drug solution was then added into the hydrogel aqueous solution in once to fit a final desired drug concentration per ml of mixture (the vast majority of the mixture volume, >=70% by volume, it is aqueous). By mixing, the two solvents interferes uniformly pushing the drug very fast out of the vehicle (e.g., DMSO) to be trapped inside the aqueous solution/hydrogel/polymer matrix in amorphous form, in fine dispersed inside this mixture. The amorphous % yield is >=90% (due to self crystallization in some cases). This suspension/mixture was further encapsulated to make capsule releasing drug in burst manner (days to few weeks durations). Amorphous based formulations are prepared fresh before implantation to avoid self-crystallization due to limited stability.

This method can be applied to any homogeneously able to be mixed solvents mixture were the first solvent is drug solvent and the second is anti-solvent (where the polymer is dissolved, or blank anti-solvent, the anti-solvent % is the major in the final mixture >=70%). FIG. 4 shows representative amorphous form of curcumin prepared in situ by this method inside the hydrogels.

With encapsulation process: To a glass vail fixed onto hot plate (40-50° C.) flushed with N2 or Ar continuously, a saturated drug solution (drug+minimum volume of solvent) was added in droplet manner. By first contact between the drug solution and hot glass surface the solvent immediately evaporates and results with the drug in amorphous form. The fast produced amorphous drug in white powder form was immediately collected and proceed with for encapsulation or administration alone or encapsulated with cells or alone encapsulated (similar to method 1 just drug and hydrogel) or with device. The amorphous % yield is >=70% (due to self crystallization in some cases and how fast is the evaporation depending on the solvent). Amorphous based formulations are prepared fresh before implantation to avoid auto-crystallization due to limited stability.

Fabrication of Alginate Hydrogel Spheres/Alginate Loaded Drugs, Crystalline or Amorphous Alginate hydrogel spheres were made with an in-house customized electro-jetting system: voltage generator, vertical syringe pump (Harvard Apparatus), and a gelation bath basin. Voltage was coupled to the syringe needle dispensing the alginate and grounded to the gelling bath vessel. Spheres were made with a 2.0% solution of commercially available sterile alginate (PRONOVA SLG20, NovaMatrix, Sandvika, Norway) dissolved in 0.9% saline (pH≈7.4, Osmotic pressure 290 mOsm). For the drug formulation loaded capsule drugs crystals or amorphous form (both amorphous methods) were added to the dissolved alginate and mixed well, alginate with or without drug following the first step is crosslinked with 250 mL of sterile $BaCl_2$ gelling solution (20 mM $BaCl_2$, 250 mM D-Mannitol, 25 mM HEPES, pH≈7.4, Osmotic pressure 290 mOsm)[1]. Alginate hydrogel 500 µm diameter microspheres were generated with a 25G blunt needle, a voltage of 5 kV and a 200 µl/min flow rate. Immediately after gelation, alginate spheres were washed with HEPES buffer (25 mM HEPES, 1.2 mM $MgCl_2\times6H2O$, 4.7 mM KCl, 132 mM $NaCl_2$, pH≈7.4, ≈290 mOsm) 4 times and stored overnight at 4° C. Immediately prior to implantation, spheres were washed an additional 2 times with 0.9% saline. A sampling of the fabricated hydrogels was submitted for endotoxin testing by a commercial vendor (Charles River, Wilmington, Mass.) and the results showed that SLG20 hydrogels contained <0.05 EU/ml of endotoxin levels (below detectable limits).

In Vitro Drugs Release from the Capsules Loaded Crystalline or Amorphous Formulations:

Release study was carried out in 3 different media, a normal saline-Isopropyl alcohol (10%) mixture, a phosphate buffer (pH 7.4), or for accelerated condition with phosphate buffered saline (pH 7.4) either with 0.1% w/v or 03% w/v SDS. Release study at NS+10% IPA was carried out in 2 ml medium at 37° C. Sampling was carried out by replacement of 1.5 ml of release medium by total replacement of release medium with fresh medium. Sampling point were 6 h, 1, 3, 5, 7, and then weekly, until completion of a 60-day period. For release in accelerated condition (PBS+SDS), the same time points were followed while 20 µl of drug loaded capsules were incubated in 2 ml release medium to achieve sink conditions. Drug concentration in samples was measured by reverse phase HPLC on C-18 column with a mobile phase or using UV calibrated system. An isocratic mode was set at a flow rate of 0.5-2 ml/min and a different wave-length of nm and 20-50 µl of samples was injected into an HPLC system (Waters, LC-Module-I) or UV analyzed. Calibration curves were prepared in concentration range of 0.05-10 µg/ml. Using prepared calibration curves, drugs concentration in different release samples were calculated.

Rat Islet Isolation, Purification, and Encapsulation

Male Sprague-Dawley rats from Jackson Laboratories (Bar Harbor, Me.) weighing approximately 300 grams were used for harvesting islets. All rats were anesthetized by a 1:20 xylazine (10 mg/kg) to ketamine (150 mg/kg) injection given intraperitoneally, and the total volume of each injection was 0.4 ml-0.5 ml depending on the weight of rat. Isolation surgeries were performed as described by Lacy and Kostianovsky[2]. Briefly, the bile duct was cannulated and the pancreas was distended by an in vivo injection of 0.15% Liberase (Research Grade, Roche) in RPMI 1640 media solution. Rats were sacrificed by cutting the descending aorta and the distended pancreatic organs were removed and held in 50 ml conical tubes on ice until the completion of all surgeries. All tubes were placed in a 37° C. water bath for a 30 min digestion, which was stopped by adding 10-15 ml of cold M199 media with 10% heat-inactivated fetal bovine serum (HIFBS) and lightly shaking. Digested pancreases were washed twice in the same aforementioned M199 media, filtered through a 450 µm sieve, and then suspended in a Histopaque 1077 (Sigma)/M199 media gradient and centrifuged at 1,700 RCF at 4° C. Depending on the thickness of the islet layer that was formed within the gradient, this step was repeated for higher purity islets. Finally, the islets were collected from the gradient and further isolated by a series of six gravity sedimentations, in which each supernatant was discarded after four minutes of settling. Purified islets were hand-counted by aliquot under a light microscope and then washed three times in sterile ix phosphate-buffered saline. Islets were then washed once in RPMI 1640 media with 10% HIFBS and 1% penicillin/streptomycin, and cultured in this media overnight for further use.

Immediately prior to encapsulation, the cultured islets were centrifuged at 1,400 rpm for 1 minute and washed with Ca-free Krebs-Henseleit (KH) Buffer (4.7 mM KCl, 25 mM HEPES, 1.2 mM $KH_2PO_4$, 1.2 mM $MgSO_4\times7H_2O$, 135 mM NaCl, pH≈7.4, ≈290 mOsm). After washing, islets were centrifuged again and all supernatant was aspirated. The islet pellet was then re-suspended in a 2.0% solution of SLG20 alginate dissolved in 0.9% NaCl solution at an islet density of 1,000 islets per 1.0 ml alginate solution. Spheres were crosslinked using a $BaCl_2$ gelling solution and their sizes were controlled using similar procedures as the empty spheres (described above). Immediately after crosslinking, the encapsulated islets were washed 4 times with HEPES buffer and 2 times with RPMI Medium 1640 with 10% HIFBS and cultured overnight at 37° C. for transplantation. As the islets had variable sizes (50-400 μm) and there was an inevitable loss of islets during the encapsulation process, the total number of encapsulated islets were recounted and converted into islet equivalents (IE, normalized to 150 μm size) based on a previously published method (Ricordi, C. et al. Islet isolation assessment in man and large animals. Acta 18 Diabetol. Lat. 27, 185195 (1990)) prior to transplantation.

Implantation/Transplantation Surgeries

All animal protocols were approved by the MIT Committee on Animal Care, and all surgical procedures and post-operative care was supervised by MIT Division of Comparative Medicine veterinary staff. Immune-competent male non-diabetic or STZ-induced diabetic C57BL/6 mice (Jackson Laboratory, Bar Harbor, Me.) were anesthetized with 3% isoflurane in oxygen and had their abdomens shaved and sterilized using betadine and isopropanol. Pre-operatively, all mice also received a 0.05 mg/kg dose of buprenorphine subcutaneously as a pre-surgical analgesic, along with 0.3 mL of 0.9% saline subcutaneously to prevent dehydration. A 0.5 mm incision was made along the midline of the abdomen and the peritoneal lining was exposed using blunt dissection. The peritoneal wall was then grasped with forceps and a 0.5-1 mm incision was made along the linea alba. A desired volume of spheres (all materials without islets, as well as SLG20 spheres encapsulating rat islets) were then loaded into a sterile pipette and implanted into the peritoneal cavity through the incision. The incision was then closed using 5-0 taper-tipped polydioxanone (PDS II) absorbable sutures. The skin was then closed over the incision using a wound clip and tissue glue.

For non-human primate (NHP) procedures, buprenorphine (0.01-0.03 mg/kg) was administered as a pre-operative analgesic. NHPs were then sedated using an intramuscular (IM) injection of ketamine (10 mg/kg) with an addition of midazolam as dictated by DCM vet staff if needed for additional sedation. Animals were maintained on a circulating warm water blanket and covered with a towel during the procedure to maintain body temperature. Either 0.5 or 1.5 mm diameter (drug-loaded) SLG20 spheres were implanted by minimally invasive laparoscopic surgery, and injected into the dorsal (back) regions of 4 non-human primates (cynomolgus macaques) using 18 and 12 gauge custom-manufactured (Harvard Apparatus) sterile stainless steel needles, with slip tip syringes in order to prevent shearing of our biomaterial upon injection. Needles were inserted tangentially to the backs of the NHPs, and were slid (tunneled) approximately 1-2 cm away from the initial injection point, in order to try to separate the injection from that of the site of eventual material response. Spheres (0.5 and 1.5 mm diameter) were injected into 4 total spots on the flank of 4 of our non-human primates: two spots on the left flank and two on the right, for 0.5 mm and 1.5 mm diameter sphere implants, respectively.

Blood Glucose Monitoring

To create insulin-dependent diabetic mice, healthy C57BL/6 mice were treated with Streptozotocin (STZ) by the vendor (Jackson Laboratory, Bar Harbor, Me.) prior to shipment to MIT. The blood glucose levels of all the mice were retested prior to transplantation. Only mice whose non-fasted blood glucose levels were above 300 mg/dL for two consecutive days were considered diabetic and underwent transplantation.

Blood glucose levels were monitored three times a week following transplantation of islet-containing alginate capsules. A small drop of blood was collected from the tail vein using a lancet and tested using a commercial glucometer (Clarity One, Clarity Diagnostic Test Group, Boca Raton, Fla.). Mice with unfasted blood glucose levels below 200 mg/dL were considered normoglycemic. Monitoring continued until all mice had returned to a hyperglycemic state at which point they were euthanized and the spheres were retrieved.

Retrieval of Cells, Tissues, and Materials

At desired time points post-implantation or transplantation (with encapsulated islets), as specified in figures, mice were euthanized by $CO_2$ administration, followed by cervical dislocation. In certain instances, 5 ml of ice cold PBS was first injected in order perform an intraperitoneal lavage to rinse out and collect free-floating intraperitoneal immune cells. An incision was then made using the forceps and scissors along the abdomen skin and peritoneal wall, and intraperitoneal lavage volumes were pipetted out into fresh 15 ml falcon tubes (each prepared with 5 ml of RPMI cell culture media). Next, a wash bottle tip was inserted into the abdominal cavity. KREBS buffer was then used to wash out all material spheres from the abdomen and into petri dishes for collection. After ensuring all the spheres were washed out or manually retrieved (if fibrosed directly to intraperitoneal tissues), they were transferred into 50 mL conical tubes for downstream processing and imaging. After intraperitoneal lavage and sphere retrieval, remaining fibrosed intraperitoneal tissues were also excised for downstream FACS and expression analyses.

For non-human primate intraperitoneal and subcutaneous retrievals, similar to when material was implanted, NHPs were once again given buprenorphine (0.01-0.03 mg/kg) as a pre-operative analgesic, and sedated using an IM injection of ketamine (10 mg/kg), with midazolam as dictated by DCM vet staff if needed for additional sedation. Animals were once again maintained on a circulating warm water blanket and covered with a towel during the procedure to maintain body temperature. 8 mm diameter biopsy punches were then used to sample the entire skin and subcutaneous space at 2 and later at 4 weeks post-implantation. Following biopsy punches, the retrieval site was closed with 3-0 nylon in a simple-interrupted pattern and VetBond (tissue glue). For IP retrievals, minimally invasive laparoscopic surgery was also used (similar to implant procedures).

Imaging of the Retrieved Material Spheres

For phase contrast imaging, retrieved materials were gently washed using Krebs buffer and transferred into 35 mm petri dishes for phase contrast microscopy using an Evos X1 microscope (Advanced Microscopy Group).

For bright-field imaging of retrieved materials, samples were gently washed using Krebs buffer and transferred into 35 mm petri dishes for bright-field imaging using a Leica Stereoscopic microscope.

Live/Dead Islet Staining

LIVE/DEAD® Viability/Cytotoxicity Kit (Life technologies, Carlsbad Calif.; CA #L-3224) was used according to the manufacturer's instructions to assess the viability of islets post-encapsulation with and without co-encapsulated drug formulations.

Confocal Immunofluorescence

Immunofluorescence imaging was used to determine immune populations attached to spheres. Materials were retrieved from mice and fixed overnight using 4% paraformaldehyde at 4° C. Samples where then washed twice with KREBS buffer, permeabilized for 30 min using a 0.1% Triton X100 solution, and subsequently blocked for 1 hour using a 1% bovine serum albumin (BSA) solution. Next, the spheres were incubated for 1 hour in an immunostaining cocktail solution consisting of DAPI (500 nM), specific marker probes (1:200 dilution) in BSA. After staining, spheres were washed three times with a 0.1% Tween 20 solution and maintained in a 50% glycerol solution. Spheres were then transferred to glass bottom dishes and imaged using an LSM 700 point scanning confocal microscope (Carl Zeiss Microscopy, Jena Germany) equipped with 5 and 10× objectives. Obtained images where adjusted linearly for presentation using Photoshop (Adobe Inc. Seattle, Wash.).

Histological Processing for H&E and Masson's Trichrome Staining

Retrieved materials where fixed overnight using 4% paraformaldehyde at 4° C. After fixation, alginate sphere or retrieved tissue samples were washed using 70% alcohol. The materials where then mixed with 4 degrees calcium-cooled Histogel (VWR, CA #60872-486). After the molds hardened, the blocks were processed for paraffin embedding, sectioning and staining according to standard histological methods.

FACS Analysis

Single-cell suspensions of freshly excised tissues were prepared using a gentle MACS Dissociator (Miltenyi Biotec, Auburn, Calif.) according to the manufacturer's protocol. Single-cell suspensions were prepared in a passive PEB dissociation buffer (1×PBS, pH 7.2, 0.5% BSA, and 2 mM EDTA) and suspensions were passed through 70 μm filters (Cat. #22363548, Fisher Scientific, Pittsburgh, Pa.). This process removed the majority of cells adhered to the surface (>90%). All tissue and material sample-derived, single-cell populations were then subjected to red blood cell lysis with 5 ml of 1×RBC lysis buffer (Cat. #00-4333, eBioscience, San Diego, Calif., USA) for 5 min at 4° C. The reaction was terminated by the addition of 20 ml of sterile 1×PBS. The cells remaining were centrifuged at 300-400 g at 4° C. and resuspended in a minimal volume (~50 μl) of eBioscience Staining Buffer (cat. #00-4222) for antibody incubation. All samples were then co-stained in the dark for 25 min at 4° C. with two of the fluorescently tagged monoclonal antibodies specific for the cell markers CD68 (1 μl (0.5 μg) per sample; CD68-Alexa647, Clone FA-11, Cat. #11-5931, BioLegend), Ly-6G (Gr-1) (1 μl (0.5 μg) per sample; Ly-6G-Alexa-647, Clone RB6-8C5, Cat. #108418, BioLegend), CD11b (1 μl (0.2 μg) per sample; or CD11b-Alexa-488, Clone M1/70, Cat. #101217, BioLegend). For alpha smooth muscle actin (fibrosis) analysis, additional cell aliquots were also fixed in 1% paraformaldehyde and permeabilized with 0.1% triton X-100 before being stained with Cy3-conjugated anti-mouse αSM actin antibody (1:100) (Sigma Aldrich, St. Louis, Mo.). Two ml of eBioscience Flow Cytometry Staining Buffer (cat. #00-4222, eBioscience) was then added, and the samples were centrifuged at 400-500 g for 5 min at 4° C. Supernatants were removed by aspiration, and this wash step was repeated two more times with staining buffer. Following the third wash, each sample was resuspended in 500 μl of Flow Cytometry Staining Buffer and run through a 40 μm filter (Cat. #22363547, Fisher Scientific) for eventual FACS analysis using a BD FACSCalibur (cat. #342975), BD Biosciences, San Jose, Calif., USA). For proper background and laser intensity settings, unstained, single antibody, and IgG (labeled with either Alexa-488 or Alexa-647, BioLegend) controls were also run. For primate cell staining, anti-human CD68 Alexa Fluor-647-conjugated antibody (Clone KP1, Cat. #sc-20060, Santa Cruz, Dallas, Tex.) was used in conjunction with the above BioLegend (anti-mouse/human) CD11b-AF488 antibody.

NanoString Analysis

RNAs for mock-implanted (mock) controls, or for various drug-loaded 0.5 mm diameter alginate sphere-bearing mice (n=4/group) were isolated from tissue samples taken at various time points after implantation, as described. Respective RNAs were quantified, diluted to the appropriate concentration (100 ng/μl), and then 500 ng of each sample was processed according to NanoString manufacturer protocols for expression analysis via our customized multiplexed gene mouse macrophage subtyping panel. RNA levels (absolute copy numbers) were obtained following nCounter (NanoString Technologies Inc., Seattle, Wash.) quantification, and group samples were analyzed using nSolver analysis software (NanoString Technologies Inc., Seattle, Wash.).

Statistical Analysis

Data are expressed as mean±SEM, and N=5 mice per time point and per treatment group. For Rat studies N=3 per treatment. These sample sizes where chosen based on previous literature. All animals were included in analyses except in instances of unforeseen sickness or morbidity. Animal cohorts where randomly selected. Investigators where not blind to performed experiments. For qPCR or FACS, data were analyzed for statistical significance either by unpaired, two-tailed t-test, or one-way ANOVA with Bonferroni multiple comparison correction, unless indicated otherwise, as implemented in GraphPad Prism 5; *: $p<0.05$, : $p<0.001$, and *: $p<0.0001$. High throughput NanoString based gene expression analysis data was divided into sets based on macrophage subtype and compartment. Data was normalized using the geometric means of the NanoString positive controls and background levels were established using the means of the negative controls. Housekeeping genes Tubb5, Hprt1, Bact, and Cltc were used to normalize between samples. Data was then log-transformed. For each subtype, time, and compartment group, a two-way ANOVA for the effect of size blocking on genes was performed. P-values were computed from pairwise comparisons performed using Tukey's Honest Significant Difference test and the Bonferroni correction was used to control the overall error rate.

qPCR Analysis

Total RNA was isolated from fibrosed spheres (with adhered tissue and immune overgrowth, if present), liquid nitrogen snap-frozen immediately following excision, using TRIzol (Invitrogen, Carlsbad, Calif.) according to the manufacturer's instructions. In addition, to help ensure complete tissue disruption, we also employed strong mechanical disruption with a Polytron homogenizer. Thus, gene expression signatures shown throughout are proportional and representative of the entire cell population present on and/or around retrieved materials. Before reverse transcription using the High Capacity cDNA Reverse Transcription kit (Cat. #4368814; Applied Biosystems, Foster City, Calif.), all samples were first normalized for comparison by loading the same input 1 μg total RNA in a volume of 20 μl for each sample. cDNA (4.8 μl; 1:20 dilution) in a total volume of 16 μl (including SYBR Green and PCR primers) was amplified by qPCR with the following oligonucleotide primers. Mouse (5'-GAAATCCACCAAAGCTCACG-3' (SEQ. ID. No.:1); reverse: 5'-CGGGTTCCGCTGTGTAAG-3' (SEQ. ID. No.:

2)) and rat (5'-CTCTCGTGCCATGTGAACC-3' (SEQ. ID. No.:3); reverse: 5'-TTCTCTAAATTGGTCCCAGGAA-3' (SEQ. ID. No.:4)) Pdx1 primers were designed using Primer Express software (Applied Biosystems, Carlsbad, Calif., USA) and evaluated using LaserGene software (DNAStar, Madison, Wis., USA) to ensure species rat (encapsulated islet) or mouse (host)-specificity, and normalized to mouse (5'-GCTTCTTTGCAGCTCCTTCGTT-3' (SEQ. ID. No.:5); reverse: 5'-CGGAGCCGTTGTCGACGACC-3' (SEQ. ID. No.:6)) and rat (5'-ACCTTCTTGCAGCTCCTCCGTC-3' (SEQ. ID. No.:7); reverse: 5'-CGGAGCCGTTGTCGAC-GACG-3' (SEQ. ID. No.:8)) Beta-actin, respectively. Samples were incubated at 95° C. for 10 min followed by 40 cycles of 95° C. for 15 sec and 60° C. for 1 min in an ABI PRISM 7900HT Sequence Detection System (Applied Biosystems). Results were analyzed using the comparative $C_T$ ($\Delta\Delta C_T$) method as described by the manufacturer. Results were analyzed using the comparative $C_T$ ($\Delta\Delta C_T$) method and are presented as relative RNA levels, as compared to control cell samples as specified in figure legends after normalization to the β-actin RNA content of each sample. To further ensure proper normalization and sample handling across multiple retrieval time points, RNA for all samples were quantified, reverse transcribed, and analyzed by qPCR in parallel.

LCMS and Plasma Samples

LC pumps used are Agilent 1290 Infinity Binary pumps with CTC Pal Autosampler. MS is a Sciex API6500 triple quad. Sample Storage Conditions: −80° C. Sample Processing Extraction Volume: 10 μL. Extraction Method: Protein Precipitation. For example: GW2580 plasma concentration analysis: Sample Extraction Procedure: 1. 10 μL of calibration standards, quality controls, blanks and samples were aliquoted into a 96-well plate. 2. 60 μL of IS-SS (internal standard) (100 ng/mL QNZ, carbutamide, chrysin, carbamazepine, glafenine, dexamethasone, glyburide, and d4AEA in acetonitrile) were added to all samples except for double blanks. 60 μL of acetonitrile was then added to double blanks. 3. The plate was covered and samples mixed, followed by centrifugation for 5 minutes at 3000 rpm at 4° C. 4. 50 μL of supernatant was then transferred into a clean 96-well plate using a liquid handler. 5. Samples were diluted with 100 μL of MilliQ water, and the plate was once again covered and mixed for about a minute prior to sample injection onto the LC-MS/MS at 1.00-2,500 ng/mL. LC Conditions: Waters BEH C18, 50×2.1 mm, 1.7 μm. Run temperature: 50° C. Mobile Phase A, 95:5:0.1 (v:v:v) Water:Acetonitrile:Formic Acid (1.2 min). Mobile Phase B, 50:50:0.1 (v:v:v) Methanol:Acetonitrile:Formic Acid (1.3 min). Flow: 0.8 mL/min. Injection Volume: 2 μL. MS Conditions: MS/MS: API-6500. Ionization Method: Electrospray. Positive/Negative Ion: Positive. Resolution: Unit. Source Temperature (° C.): 550. Transitions (m/z): Compound ID: GW2580 367.0/245.1 Da. Int Std ID: QNZ 357.0/197.1 Da. Data Analysis: Acceptance Criteria '±20% (±25% at the LLOQ), Regression Type, Linear (1/(x*x)), Accepted Curve Range 1.00-2,500 ng/mL Carryover 0.00%. HPLC Calibration curves were obtained on an Agilent LC 1100 Series (Agilent Technologies, CA, USA) equipped with binary pump (G1312 Å), auto-sampler (G1313 Å), degasser and photodiode detector (DAD, G1315 Å). Chemstation was used for system control, data processing and data acquisition for LC. Chromatographic separation was achieved by an analytical Waters Atlantis T3 C18 column (5 μm, 4.6×250 mm). The temperature of column and auto-sampler were kept at 20° C.

Stock solution of GW2580 was prepared in dimethyl sulfoxide (DMSO) at a target concentration of 10 mg/ml and appropriate dilutions were made in DMSO to prepare standards (0.25-2500 μg/ml) for calibration curve of GW2580. 10 μl of standard solution was injected and the analytes were eluted by gradient mode using (A) acetonitrile and (B) 0.1% formic acid in water at a constant flow rate of 1 ml/min. The gradient conditions of mobile phase were as follows: 0 min 10% A, 10 min 95% A, 14 min 95% A, 16 min 10% A, 20 min 10% A.

Stock solution of curcumin was prepared in dimethyl sulfoxide (DMSO) at a target concentration of 10 mg/ml and appropriate dilutions were made in DMSO to prepare standards (0.05-500 μg/ml) for calibration curve of curcumin. 10 μl of standard solution was injected and the analytes were eluted by gradient mode using (A) acetonitrile and (B) 0.1% formic acid in water at a constant flow rate of 1 ml/min. The gradient conditions of mobile phase were as follows: 0 min 70% A, 4 min 95% A, 10 min 95% A, 12 min 70% A, 17 min 10% A.

Stock solution of QNZ was prepared in dimethyl sulfoxide (DMSO) at a target concentration of 10 mg/ml and appropriate dilutions were made in DMSO to prepare standards (0.06-125 μg/ml) for calibration curve of QNZ. 50 μl of standard solution was injected and the analytes were eluted by gradient mode using (A) acetonitrile and (B) 0.1% formic acid in water at a constant flow rate of 1 ml/min. The gradient conditions of mobile phase were as follows: 0 min 20% A, 8 min 95% A, 12 min 95% A, 13 min 20% A, 17 min 20% A.

Stock solution of LY2157299 was prepared in dimethyl sulfoxide (DMSO) at a target concentration of 10 mg/ml and appropriate dilutions were made in DMSO to prepare standards (0.06-250 μg/ml) for calibration curve of LY2157299. 50 μl of standard solution was injected and the analytes were eluted by gradient mode using (A) acetonitrile and (B) 0.1% formic acid in water at a constant flow rate of 1 ml/min. The gradient conditions of mobile phase were as follows: 0 min 10% A, 7 min 60% A, 8 min 95% A, 12 min 95% A, 13 min 10% A, 17 min 10% A.

Stock solution of KI20227 was prepared in dimethyl sulfoxide (DMSO) at a target concentration of 10 mg/ml and appropriate dilutions were made in DMSO to prepare standards (0.06-500 μg/ml) for calibration curve of KI120227. 50 μl of standard solution was injected and the analytes were eluted by gradient mode using (A) acetonitrile and (B) 0.1% formic acid in water at a constant flow rate of 1 ml/min. The gradient conditions of mobile phase were as follows: 0 min 20% A, 7 min 75% A, 8 min 95% A, 12 min 95% A, 13 min 20% A, 17 min 20% A.

Stock solution of dexamethasone was prepared in ethanol at a target concentration of 10 mg/ml and appropriate dilutions were made in ethanol to prepare standards (0.06-500 μg/ml) for calibration curve of dexamethasone. 50 μl of standard solution was injected and the analytes were eluted by gradient mode using (A) acetonitrile and (B) 0.1% formic acid in water at a constant flow rate of 1 ml/min. The gradient conditions of mobile phase were as follows: 0 min 50% A, 7 min 80% A, 8 min 95% A, 12 min 95% A, 13 min 50% A, 17 min 50% A Single-Crystal and Powder X-Ray Diffraction (SXRD and PXRD)

SXRD—Diffraction data (φ- and ω-scans) were collected at 100K on a Bruker-AXS X8 Kappa diffractometer coupled to a Bruker APEX2 CCD detector using Cu Kα radiation (lambda=1.54178 Å) or Mo Kα radiation (lambda=1 0.71073 Å) from an IμS microsource. Data reduction was carried out with the program SAINT [Bruker (2011). SAINT, Bruker-AXS Inc., Madison, Wis., USA] and semi-empirical absorption correction based on equivalents was performed with the program SADABS [Krause, L., Herbst-Irmer, R., Sheldrick, G. M. & Stalke, D., J. Appl. Cryst. 2015, 48, 3-10.]. The structure was solved with dual-space methods using the program SHELXT [Sheldrick, G. M., Acta Cryst. 2015, A71, 3-8] and refined against F2 on all data with SHELXL [Sheldrick, G. M., Acta Cryst. 2015, A71, 3-8.] using established refinement techniques [Müller, P., Crystallography Reviews 2009, 15, 57-83]. All non-hydrogen atoms were refined anisotropically. All carbon-bound hydrogen atoms were placed in geometrically calculated positions and refined using a riding model while constraining their Uiso to 1.2 times the Ueq of the atoms to which they bind (1.5 times for methyl groups). Coordinates for hydrogen atoms bound to nitrogen or oxygen were taken from the difference Fourier synthesis and those hydrogen atoms were subsequently refined semi-freely with the help of distance restraints (target values 0.84(2) Å for O—H and 0.91(2) for N—H distances) while constraining their Uiso to 1.2 times the Ueq of nitrogen or 1.5 times the Ueq of oxygen, respectively. Disorders were refined with the help of similarity restraints on 1-2 and 1-3 distances and displacement parameters as well as rigid bond restraints for anisotropic displacement parameters.

PXRD—Powder diffraction data were collected at 100K on a Bruker-AXS X8 Kappa diffractometer coupled to a Bruker APEX2 CCD detector using Cu Kα radiation (lambda=1.54178 Å) from an IμS microsource. The powder sample was held in a polyimide capillary that rotates around its axis during data collection.

Environmental Scanning Electron Microscope (ESEM)

Crystal morphology, topography, and size were studied with ESEM. Samples were placed on a conductive carbon paper and were coated with gold to a thickness of about 10 nm using a sputtering deposition machine (Polarone E5100). Afterwards, they were imaged using scanning electron microscopy (FEI E-SEM Quanta 2000) at an acceleration voltage of 2-15 KV. Three samples with 3 images of each were used for collecting 10 random measurements per image for each studied preparation.

Ex Situ and In Situ Atomic Force Microscopy (AFM)

Time-resolved atomic force microscopy was used to study the mechanism of drug release on the molecular level. Single crystals were prepared for ex situ and in situ observation in air and in solution to identify the dominant mechanisms of drug release and to determine the kinetics between crystal polymorphs. A Cypher ES Environmental AFM from Asylum Research (Santa Barbara, Calif.) was used for all experiments. The sealed liquid cells for the Cypher AFM are specifically designed with materials that are compatible for harsh solvent conditions. This AFM provides the ability to probe samples with environmental control, including precise temperature control with the modular sample stage. In this way we were able to monitor drug release in ambient conditions (T=25° C.) during ex situ measurements prior to in situ wherein we increase and maintain T=37° C. during solution exchange.

Attachment of Crystals for AFMAFM measurements were performed with Polymorph 1 and 2 crystals fixed on an epoxy substrate. Single crystals were attached using a thin film of partially-cured epoxy (MasterBond EP21AOLV) on Ted Pella 15 mm metal disks. The epoxy was partially cured at 60° C. for 30 minutes prior to depositing the crystals using a statically charged pipette tip. All crystals were used for in situ observation within one hour of sample preparation.

In situ AFM Image Collection: AFM images were collected in contact mode using Olympus TR800PSA probes (Silicon nitride probe, Cr/Au coated 5/30, 0.15 N/m spring constant) with tapping frequency of ca. 32 kHz. Image sizes ranged from 1 to 10 μm with scan rates between 2 and 5 Hz with 256 scan lines per image. Height and deflection imaging modes were employed for data analysis and image selection. The height and deflection images were processed by $2^{nd}$ order flattening and image contrast adjustment. No lowpass, median, or 2D fast Fourier transform (FFT) filters were applied to any of the AFM images.

In Situ Monitoring of the Mechanism of Drug Release:

Single crystals were attached to AFM sample pucks using epoxy, as described above, on the same day that we conducted the experiments. The samples were placed on the AFM scanner which was initially at 25° C. Ex situ images were collected of the (001) crystal surfaces at T=25° C. prior to introduction of solution. From these AFM images, the crystal edges were identified in order to determine the crystallographic directions on the upward-facing (001) crystallographic faces for crystals.

AFM fluid cell were loaded the with reagent-grade phosphate buffer solution (PBS) was allowed to thermally equilibrate to ambient temperature prior to being introduced into the AFM liquid cell. The solution was fully undersaturated upon being introduced. Upon introducing the undersaturated PBS, the temperature was set to T=37° C. and was maintained at a constant in situ temperature for the duration of the experiment. The time between introducing the solution, heating until thermally equilibration was achieved, and the AFM cantilever tip engaging with the surface, was recorded which was denoted by $t_0$. AFM images were continuously collected and the undersaturated solution was exchanged to maintain a constant degree of undersaturation. Different regions of each crystal surface was recorded, including the edges and the center of the basal (001) surfaces. Due to inherent drift that occurs with long time in situ AFM measurements, we show well equilibrated images of the surfaces over shorter time frames. These are representative of the full experimental time wherein we monitored the surface evolution for >ten hours, and in some cases exceeding 36 hours which is an extensive time for in situ AFM observations. All images were collected in contact mode; we verified that scanning in contact mode had no influence on the surface dissolution by increasing the scan size at the end of each experiment and observing uniform changes across the entire scanned areas.

The rate of drug release was measured by measuring the negative step velocity v on the (001) surfaces. The displacement between step edges $\Delta x$ were measured between sequential AFM height mode images. The time between images was recorded therefore can be used to quantify the step velocity as in Equation 1, $$v = \frac{\Delta x}{\Delta t} = \frac{x_2 - x_1}{t_2 - t_1} = \left[\frac{nm}{s}\right]. \tag{1}$$

The rate of drug release was quantified as being proportional to the rate of molecules released for crystals. The rate of molecules released is proportional to the integral of the velocity over time, Equation 2, $$n \propto l \int v dt \tag{2}$$

where l=a=0.54 nm for crystal surface, and the rate of molecules n released over time as shown by Equation 3, $$\frac{dn}{dt} = \rho v l = \left(\frac{\text{molecules}}{\text{nm}^2}\right)\left(\frac{\text{nm}}{\text{s}}\right)(\text{nm}). \qquad (3)$$

Greater than 20 independent steps for each crystal size and polymorph were measured. From this, the negative velocities and sub sequentially, the rate at which the molecules released was determined. Error bars were for all number of molecules released for each crystal surface. The calculated rate of molecules released were summed to demonstrate the cumulative rate of drug release as a function of time in an undersaturated PBS solution such that different drug crystals were comparable.

Preparation of a Polymorph of GW2580

The polymorph of GW2580 was prepared using the slow releasing crystals (surface release) method of the present invention: crystals were grown at constant temperature (20-30° C.) using solvent:anti-solvent mixing methods with concentrations of GW2580 ranging from 0.001 mg/mL to 5000 mg/mL, where the anti-solvent is added into portions. Ethyl acetate was used as a solvent while hexane as an anti-solvent. For example, 5 mg of GW2580 was initially dissolved in 2 to 80 ml ethyl acetate (e.g., 3 ml, 35 ml, 70 ml). In some crystallization experiments, solvent solutions were sonicated up to 15 minutes and/or pre-heated in a range from 20 to 80° C. to facilitate solubility. To the solution hexane was added into sub portions to fit a range of 0 to 100 ml per 5 mg of dissolved GW2580 (e.g., about 20 ml, about 30 ml, about 70 ml) depending on the desired final mean crystal size. Resulting mixtures were then incubated at stable temperature i.e. 20-30° C. The resulting crystals were analyzed by microscopy methods including SEM analysis for at least 3 sample images per preparation, with 10 random size measurements being taken in each case. Crystalline samples were also analyzed by XRD SXRD and PXRD of the Polymorph of GW2580

SXRD—Diffraction data (φ- and ω-scans) were collected at 100K on a Bruker-AXS X8 Kappa diffractometer coupled to a Bruker APEX2 CCD detector using Cu Kα radiation (lambda=1.54178 Å) or Mo Kα radiation (lambda=1 0.71073 Å) from an IμS microsource. Data reduction was carried out with the program SAINT (Bruker (2011). SAINT, Bruker-AXS Inc., Madison, Wis., USA) and semi-empirical absorption correction based on equivalents was performed with the program SADABS. The structure was determined with dual-space methods using the program SHELXT and refined against F2 on all data with SHELXL using well established refinement techniques. All non-hydrogen atoms were refined anisotropically. All carbon-bound hydrogen atoms were placed in geometrically calculated positions and refined using a riding model while constraining their Uiso to 1.2 times the Ueq of the atoms to which they bind (1.5 times for methyl groups). Coordinates for hydrogen atoms bound to nitrogen or oxygen were taken from the difference Fourier and those hydrogen atoms were subsequently refined semi-freely with the help of distance restraints (target values 0.84(2) A for O—H and 0.91(2) for N—H distances) while constraining their Uiso to 1.2 times the Ueq of nitrogen or 1.5 times the Ueq of oxygen, respectively. Disorders were refined with the help of similarity restraints on 1-2 and 1-3 distances and displacement parameters as well as rigid bond restraints for anisotropic displacement parameters. The SXRD data and statistics obtained for GW2580 crystal is shown in FIG. 20 A and in the Table 2 below.

TABLE 2

| Empirical formula: | $C_{20}H_{22}N_4O_3$ |
|---|---|
| a: | 5.449 Å |
| b: | 9.686 Å |
| c: | 17.653 Å |
| α (alpha): | 77.11° |
| β (beta): | 87.58° |
| γ (gamma): | 84.08° |
| Volume: | 903.21 Å$^3$ |
| Space group: | P-1 |
| Calculated density: | 1.347 g/cm$^3$ |
| Color: | yellow |
| Z: | 2 |
| Temperature: | −173.0° C. |
| Formula weight: | 366.420 g/mole |
| R (F): | 0.0412 |
| R$_w$ (F$^2$): | 0.1146 |
| Miscellaneous comments: | non-hydrogen atom volume: 16.7 A$^3$ |

PXRD—Powder diffraction data were collected at 100K on a Bruker-AXS X8 Kappa diffractometer coupled to a Bruker APEX2 CCD detector using Cu Kα radiation (lambda=1.54178 Å) from an IμS microsource. The powder sample was held in a polyimide capillary that was rotates around its axis during data collection. The PXRD pattern for GW2580 is shown in FIG. 20 C, and the corresponding peak listing in Table 3 below:

TABLE 3

| Peak | 2-Theta Deg | Intensity |
|---|---|---|
| 1 | 9.4 | 3212.7 |
| 2 | 10.28 | 3911.97 |
| 3 | 11.68 | 2798.57 |
| 4 | 12.32 | 1463.09 |
| 5 | 15.44 | 3815.61 |
| 6 | 16.34 | 1591.75 |
| 7 | 17.24 | 2574.64 |
| 8 | 18.12 | 2880.38 |
| 9 | 18.42 | 7752.29 |
| 10 | 18.86 | 1156.59 |
| 11 | 19.46 | 4442.76 |
| 12 | 19.6 | 3937.45 |
| 13 | 19.88 | 6602.18 |
| 14 | 21.4 | 10000 |
| 15 | 21.64 | 7277.87 |
| 16 | 22.22 | 4353.5 |
| 17 | 23.4 | 3975.46 |
| 18 | 23.82 | 4756.03 |
| 19 | 25.52 | 1807.62 |
| 20 | 25.66 | 3314.78 |
| 21 | 26 | 858.029 |
| 22 | 26.24 | 1781.45 |
| 23 | 28.52 | 3410.98 |
| 24 | 29.34 | 1171.82 |
| 25 | 29.64 | 4055.92 |
| 26 | 31.08 | 4871.21 |
| 27 | 31.22 | 2050.24 |
| 28 | 33.04 | 1041.05 |
| 29 | 34.04 | 1140.83 |

What is claimed is:

1. A uniform population of free, single crystals of a compound having chemical formula (I):

(I)

or a salt thereof, wherein each free, single crystal in the population has a characteristic dimension of at least about 1 micrometer.

2. The uniform population of free, single crystals of claim 1, wherein each free, single crystal exhibits the same polymorph.

3. The uniform population of free, single crystals of claim 1, wherein each free, single crystal has a characteristic dimension of at least about 5 microns.

4. The uniform population of free, single crystals of claim 1, wherein each free, single crystal has a characteristic dimension of at least about 50 microns.

5. The uniform population of free, single crystals of claim 1, wherein each free, single crystal has a characteristic dimension of at least about 500 microns.

6. The uniform population of free, single crystals of claim 1, wherein each free, single crystal has a characteristic dimension of at least about 1 millimeter.

7. A composition comprising a uniform population of free single crystals of claim 1, and amorphous compound having chemical formula (I), or a salt thereof.

8. A composition comprising a uniform population of free single crystals of claim 1, and a pharmaceutically acceptable carrier or excipient.

9. A composition comprising a uniform population of free single crystals of claim 1, wherein the compound having chemical formula (I), or a salt thereof, is encapsulated by a material.

10. A method of delivering to a subject a uniform population of free single crystals of a compound having chemical formula (I):

(I)

or a pharmaceutically acceptable salt thereof, comprising:

administering to the subject a uniform population of free single crystals of a compound having chemical formula (I), or a pharmaceutically acceptable salt thereof, wherein each free, single crystal in the population has a characteristic dimension of at least about 1 micrometer, thereby delivering the uniform population of free single crystals of the compound having chemical formula (I), or a pharmaceutically acceptable salt thereof, to the subject.

11. The method of claim 10, wherein the subject is a human.

12. A method of treating fibrosis in a subject in need thereof, comprising administering an effective amount of a uniform population of free, single crystals of claim 1 to the subject.

13. The method of claim 10, wherein the uniform population of free, single crystals is administered to the subject by injection.

14. The method of claim 10, wherein the uniform population of free, single crystals is administered to the subject by implantation.

15. A polymorph of a compound represented by chemical formula (I):

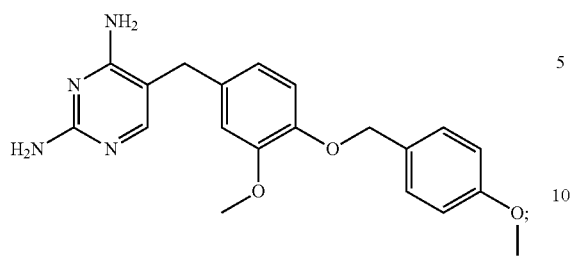

(I)

characterized by at least five major powder x-ray diffraction peaks at 2θ angles selected from 18.42°, 19.46°, 19.88°, 21.4°, 21.64°, 22.22°, 23.82°, 29.64° and 31.08°.

16. The method of claim 12, wherein the uniform population of free, single crystals is administered by injection.

17. The method of claim 12, wherein the uniform population of free, single crystals is administered by implantation.

18. The method of claim 12, wherein the fibrosis is associated with an implanted material.

19. The method of claim 18, wherein the implanted material is a medical device.

20. A method of treating or preventing a foreign body response to an implanted material in a subject in need thereof, comprising administering an effective amount of a uniform population of free, single crystals of claim 1 to the subject.

* * * * *

UNITED STATES PATENT AND TRADEMARK OFFICE
CERTIFICATE OF CORRECTION

| | |
|---|---|
| PATENT NO. | : 10,851,069 B2 |
| APPLICATION NO. | : 16/091330 |
| DATED | : December 1, 2020 |
| INVENTOR(S) | : Farah et al. |

Page 1 of 1

It is certified that error appears in the above-identified patent and that said Letters Patent is hereby corrected as shown below:

In the Specification

In Column 1, Line 13, after paragraph "RELATED APPLICATIONS" insert heading & paragraph:
--GOVERNMENT SUPPORT
This invention was made with government support under W81XWH-14-1-0100 awarded by the Defense Health Agency, Medical Research and Development Branch. The government has certain rights in the invention.--

Signed and Sealed this
Eighteenth Day of November, 2025

John A. Squires
*Director of the United States Patent and Trademark Office*